US010939822B2

(12) United States Patent
Ben-Haim et al.

(10) Patent No.: US 10,939,822 B2
(45) Date of Patent: *Mar. 9, 2021

(54) BODY STRUCTURE IMAGING

(71) Applicant: Tylerton International Holdings Inc., Road Town (VG)

(72) Inventors: Shlomo Ben-Haim, London (GB); Yoel Zilberstien, Herzlia (IL); Nathaniel Roth, Tel-Aviv (IL)

(73) Assignee: Tylerton International Holdings Inc., Road Town (VG)

( * ) Notice: Subject to any disclaimer, the term of this patent is extended or adjusted under 35 U.S.C. 154(b) by 854 days.

This patent is subject to a terminal disclaimer.

(21) Appl. No.: 14/762,879

(22) PCT Filed: Jan. 24, 2014

(86) PCT No.: PCT/IL2014/050088
§ 371 (c)(1),
(2) Date: Jul. 23, 2015

(87) PCT Pub. No.: WO2014/115150
PCT Pub. Date: Jul. 31, 2014

(65) Prior Publication Data
US 2015/0351834 A1 Dec. 10, 2015

Related U.S. Application Data

(60) Provisional application No. 61/875,069, filed on Sep. 8, 2013, provisional application No. 61/875,074, filed (Continued)

(51) Int. Cl.
*A61B 5/00* (2006.01)
*A61B 6/03* (2006.01)
(Continued)

(52) U.S. Cl.
CPC ............ *A61B 5/0035* (2013.01); *A61B 5/004* (2013.01); *A61B 5/0044* (2013.01); *A61B 5/055* (2013.01);
(Continued)

(58) Field of Classification Search
None
See application file for complete search history.

(56) References Cited

U.S. PATENT DOCUMENTS

| 5,077,035 A | 12/1991 | Wieland et al. |
| 5,560,360 A | 10/1996 | Filler et al. |

(Continued)

FOREIGN PATENT DOCUMENTS

| CN | 1981710 | 6/2007 |
| CN | 101005874 | 7/2007 |

(Continued)

OTHER PUBLICATIONS

Travin, M.I. "Cardiac Autonomic Imaging with SPECT Tracers", Journal of Nuclear Cardiology (2013) 20: 128, pp. 128-144, hereafter referred to as "Travin".*
(Continued)

*Primary Examiner* — Pascal M Bui Pho
*Assistant Examiner* — Farouk A Bruce

(57) ABSTRACT

A method of guiding a cardiac treatment using a functional imaging modality, comprising: providing functional imaging modality data from a functional imaging modality which images an intrabody volume of a patient containing a heart, the patient having been injected with an imaging agent having a nervous tissue uptake by an autonomic nervous system (ANS) of the heart, the ANS comprising at least one GP; locating the at least one GP innervating the heart based on the functional imaging modality data; and providing the located at least one GP.

28 Claims, 60 Drawing Sheets
(55 of 60 Drawing Sheet(s) Filed in Color)

Related U.S. Application Data on Sep. 8, 2013, provisional application No. 61/875,070, filed on Sep. 8, 2013, provisional application No. 61/831,664, filed on Jun. 6, 2013, provisional application No. 61/803,611, filed on Mar. 20, 2013, provisional application No. 61/776,599, filed on Mar. 11, 2013, provisional application No. 61/756,112, filed on Jan. 24, 2013.

(51) Int. Cl.

| | | |
|---|---|---|
| A61B 6/00 | (2006.01) | |
| G06T 7/11 | (2017.01) | |
| G06T 7/174 | (2017.01) | |
| A61B 5/055 | (2006.01) | |
| G06T 7/00 | (2017.01) | |
| G06T 11/00 | (2006.01) | |
| G06T 11/60 | (2006.01) | |
| A61B 8/08 | (2006.01) | |
| A61B 18/14 | (2006.01) | |
| A61B 18/00 | (2006.01) | |

(52) U.S. Cl.
CPC .......... *A61B 5/4035* (2013.01); *A61B 5/4041* (2013.01); *A61B 5/72* (2013.01); *A61B 5/7425* (2013.01); *A61B 6/032* (2013.01); *A61B 6/037* (2013.01); *A61B 6/481* (2013.01); *A61B 6/506* (2013.01); *A61B 6/5235* (2013.01); *A61B 6/5247* (2013.01); *A61B 8/085* (2013.01); *A61B 18/1492* (2013.01); *G06T 7/0012* (2013.01); *G06T 7/11* (2017.01); *G06T 7/174* (2017.01); *G06T 11/003* (2013.01); *G06T 11/60* (2013.01); *A61B 5/4893* (2013.01); *A61B 2018/00434* (2013.01); *A61B 2018/00577* (2013.01); *A61B 2018/00642* (2013.01); *G06T 2200/04* (2013.01); *G06T 2207/10076* (2013.01); *G06T 2207/10081* (2013.01); *G06T 2207/10104* (2013.01); *G06T 2207/10136* (2013.01); *G06T 2207/30024* (2013.01); *G06T 2207/30048* (2013.01); *G06T 2211/40* (2013.01)

(56) References Cited

U.S. PATENT DOCUMENTS

| | | | | |
|---|---|---|---|---|
| 5,633,511 A * | 5/1997 | Lee | ......................... | G06T 5/009 250/587 |
| 5,789,420 A | 8/1998 | Efange et al. | | |
| 6,128,415 A | 10/2000 | Hultgren, III et al. | | |
| 6,211,360 B1 | 4/2001 | Glick et al. | | |
| 6,310,967 B1 * | 10/2001 | Heine | ................... | G06T 7/0012 382/128 |
| 6,358,492 B1 | 3/2002 | Kuhar et al. | | |
| 6,490,480 B1 | 12/2002 | Lerner | | |
| 6,511,500 B1 | 1/2003 | Rahme | | |
| 6,845,267 B2 | 1/2005 | Harrison et al. | | |
| 7,363,076 B2 | 4/2008 | Yun et al. | | |
| 8,060,259 B2 | 11/2011 | Budhraja et al. | | |
| 8,359,092 B2 | 1/2013 | Hayam et al. | | |
| 8,364,285 B2 | 1/2013 | Rezai | | |
| 8,440,168 B2 | 5/2013 | Yang et al. | | |
| 8,659,603 B2 * | 2/2014 | Song | ...................... | A61B 6/469 345/440 |
| 2004/0138550 A1 | 7/2004 | Hartlep et al. | | |
| 2005/0004465 A1 | 1/2005 | Abuhamad | | |
| 2005/0008126 A1 | 1/2005 | Juh et al. | | |
| 2005/0080327 A1 | 4/2005 | Jenkins et al. | | |
| 2005/0215889 A1 | 9/2005 | Patterson, II | | |
| 2005/0261672 A1 | 11/2005 | Deem et al. | | |
| 2006/0025673 A1 * | 2/2006 | De Leon | ............... | G06T 7/0012 600/410 |
| 2006/0085049 A1 | 4/2006 | Cory et al. | | |
| 2006/0127309 A1 | 6/2006 | Raffel et al. | | |
| 2006/0287648 A1 | 12/2006 | Schwartz | | |
| 2007/0016028 A1 | 1/2007 | Donaldson et al. | | |
| 2007/0049817 A1 | 3/2007 | Preiss et al. | | |
| 2007/0106337 A1 | 5/2007 | Errico et al. | | |
| 2007/0127793 A1 | 6/2007 | Beckett et al. | | |
| 2008/0031815 A1 | 2/2008 | Chen et al. | | |
| 2008/0042067 A1 * | 2/2008 | Rousso | ................... | G01T 1/161 250/363.04 |
| 2008/0146914 A1 | 6/2008 | Polzin et al. | | |
| 2008/0161803 A1 | 7/2008 | Oral et al. | | |
| 2008/0187094 A1 | 8/2008 | Stodilka et al. | | |
| 2008/0279436 A1 | 11/2008 | Razifar et al. | | |
| 2009/0192393 A1 | 7/2009 | Hayam et al. | | |
| 2009/0192394 A1 | 7/2009 | Guttag et al. | | |
| 2010/0193696 A1 | 8/2010 | Blevis et al. | | |
| 2010/0221182 A1 | 9/2010 | Purohit et al. | | |
| 2010/0268289 A1 | 10/2010 | Chen et al. | | |
| 2010/0312128 A1 | 12/2010 | Karst et al. | | |
| 2011/0087088 A1 | 4/2011 | Korn et al. | | |
| 2011/0144723 A1 | 6/2011 | Streeter et al. | | |
| 2011/0152974 A1 | 6/2011 | Rezai et al. | | |
| 2011/0189096 A1 | 8/2011 | Watanabe et al. | | |
| 2011/0218818 A1 | 9/2011 | Butson et al. | | |
| 2011/0224962 A1 | 9/2011 | Goldberger et al. | | |
| 2011/0230775 A1 * | 9/2011 | Barley | ............... | A61B 5/02007 600/508 |
| 2011/0238128 A1 | 9/2011 | Dobak, III | | |
| 2011/0306846 A1 | 12/2011 | Osorio | | |
| 2012/0033864 A1 | 2/2012 | Wieczorek et al. | | |
| 2012/0065492 A1 | 3/2012 | Gertner et al. | | |
| 2012/0155733 A1 | 6/2012 | Wagenknecht | | |
| 2012/0271171 A1 | 10/2012 | Gertner | | |
| 2012/0321153 A1 * | 12/2012 | Dwivedi | ............. | A61B 6/037 382/128 |
| 2013/0072790 A1 | 3/2013 | Ludwig et al. | | |
| 2013/0116681 A1 | 5/2013 | Zhang | | |
| 2013/0123773 A1 * | 5/2013 | Schwartz | ............. | A61B 5/7285 606/34 |
| 2013/0131746 A1 | 5/2013 | Simon et al. | | |
| 2013/0272961 A1 | 10/2013 | Avory et al. | | |
| 2014/0046179 A1 | 2/2014 | Olcott et al. | | |
| 2015/0327805 A1 | 11/2015 | Ben-Haim | | |
| 2015/0351834 A1 | 12/2015 | Ben-Haim et al. | | |
| 2015/0359430 A1 | 12/2015 | Ben-Haim | | |
| 2015/0366523 A1 | 12/2015 | Ben-Haim | | |
| 2016/0027342 A1 | 1/2016 | Ben Haim | | |
| 2016/0217571 A1 | 7/2016 | Ben-Haim | | |
| 2016/0220835 A1 | 8/2016 | Ben-Haim | | |
| 2016/0331337 A1 | 11/2016 | Ben Haim | | |

FOREIGN PATENT DOCUMENTS

| | | |
|---|---|---|
| CN | 101137326 | 3/2008 |
| CN | 101219058 | 7/2008 |
| CN | 101687780 | 3/2010 |
| CN | 101859641 | 10/2010 |
| CN | 102120039 | 7/2011 |
| CN | 102223838 | 10/2011 |
| CN | 102740769 | 10/2012 |
| EP | 1733692 | 12/2006 |
| EP | 2474526 | 7/2012 |
| EP | 2591722 | 5/2013 |
| JP | 2007-144175 | 6/2007 |
| JP | 2008-149147 | 7/2008 |
| JP | 2008-259696 | 10/2008 |
| JP | 2010-514786 | 5/2010 |
| JP | 2010-178949 | 8/2010 |
| JP | 2012-509701 | 4/2012 |
| JP | 2013-103134 | 5/2013 |
| KR | 20090074399 | 7/2009 |
| WO | WO 01/82978 | 11/2001 |
| WO | WO 02/102238 | 12/2002 |
| WO | WO 2005/053615 | 6/2005 |
| WO | WO 2007/002541 | 1/2007 |
| WO | WO 2008/009021 | 1/2008 |
| WO | WO 2008/083056 | 6/2008 |

(56) References Cited

FOREIGN PATENT DOCUMENTS

| WO | WO 2008/121578 | 10/2008 |
|----|----------------|---------|
| WO | WO 2009/022271 | 2/2009 |
| WO | WO 2010/058372 | 5/2010 |
| WO | WO 2011/046879 | 4/2011 |
| WO | WO 2011/091069 | 6/2011 |
| WO | WO 2011/110959 | 9/2011 |
| WO | WO 2012/011036 | 1/2012 |
| WO | WO 2012/061153 | 5/2012 |
| WO | WO 2012/149552 | 11/2012 |
| WO | WO 2013/036869 | 3/2013 |
| WO | WO 2014/115148 | 7/2014 |
| WO | WO 2014/115150 | 7/2014 |
| WO | WO 2014/115151 | 7/2014 |
| WO | WO 2014/115152 | 7/2014 |
| WO | WO 2014/141247 | 9/2014 |
| WO | WO 2015/033317 | 3/2015 |
| WO | WO 2015/033319 | 3/2015 |
| WO | WO 2015/104672 | 7/2015 |
| WO | WO 2015/181753 | 12/2015 |

OTHER PUBLICATIONS

Rozovsky et al, "Added Value of SPECT/CT for Correlation of MIBG Scintigraphy and Diagnostic CT in Neuroblastoma and Pheochromocytoma", American Journal of Roentgenology. 2008; 190:1085-1090 (Year: 2008).*
Decision to Refuse a European Patent dated Jan. 24, 2018 From the European Patent Office Re. Application No. 14742800.7. (35 Pages).
Summons to Attend Oral Proceedings Pursuant to Rule 115(1) EPC dated May 17, 2017 From the European Patent Office Re. Application No. 14742800.7. (15 Pages).
Laplante "Template", Comprehensive Dictionary of Electrical Engineering, XP055349747, 2nd Ed., p. 684, Jan. 2005.
Lorenzen et al. "Multi-model Image Set Registration and Atlas Formation", Medical Image Analysis, XP005405122, 10(3): 440-451, Available Online May 24, 2005.
Oxford English Dictionary "Mapping", Definition, Oxford English Dictionary, XP055350368, Retrieved From the Internet, Mar. 1, 2017.
Oxford English Dictionary "Normalize", Definition, English Oxford Dictionary, XP055349748, Retrieved From the Internet, Feb. 27, 2017.
Restriction Official Action dated May 1, 2018 From the US Patent and Trademark Office Re. U.S. Appl. No. 14/762,932. (7 pages).
International Preliminary Report on Patentability dated Jul. 21, 2016 From the International Bureau of WIPO Re. Application No. PCT/IB2015/050148.
International Preliminary Report on Patentatibility dated Mar. 17, 2016 From the International Bureau of WIPO Re. Application No. PCT/IB2014/064316.
International Preliminary Report on Patentability dated Mar. 17, 2016 From the International Bureau of WIPO Re. Application No. PCT/IB2014/064319.
Supplementary European Search Report and the European Search Opinion dated Jan. 4, 2016 From the European Patent Office Re. Application No. 14743474.0.
Ernst et al. "Image Guided Ablation of Ganglionated Plexi as an Additional to PV Isolation—Follow-Up Results of the Initial Case Series", Heart Rhythm, XP029240122, 12(5/Suppl.): S434-S435, Poster Session V, # PO05-83, May 2015. p. 434, 435, Abstract PO05-83.
Lemery et al. "Feasibility Study of Endocardial Mapping of Ganglionated Plexuses During Catheter Ablation of Atrial Fibrillation", Heart Rhythm, X024972538, 3(4): 387-396, Apr. 2006. p. 395, Left col., Lines 3-30.
Communication Relating to the Results of the Partial International Search dated Apr. 16, 2015 From the International Searching Authority Re. Application No. PCT/IB2015/050148.
International Preliminary Report on Patentatbility dated Aug. 6, 2015 From the International Bureau of WIPO Re. Application No. PCT/IL2014/050086.
International Preliminary Report on Patentability dated Aug. 6, 2015 From the International Bureau of WIPO Re. Application No. PCT/IL2014/050088.
International Preliminary Report on Patentability dated Aug. 6, 2015 From the International Bureau of WIPO Re. Application No. PCT/IL2014/050089.
International Preliminary Report on Patentability dated Aug. 6, 2015 From the International Bureau of WIPO Re. Application No. PCT/IL2014/050090.
International Preliminary Report on Patentability dated Sep. 24, 2015 From the International Bureau of WIPO Re. Application No. PCT/IL2014/050246.
International Search Report and the Written Opinion dated Oct. 1, 2015 From the International Searching Authority Re. Application No. PCT/IB2015/053984.
International Search Report and the Written Opinion dated Jun. 5, 2014 From the International Searching Authority Re. Application No. PCT/IL2014/050086.
International Search Report and the Written Opinion dated Jun. 9, 2014 From the International Searching Authority Re. Application No. PCT/IL2014/050088.
International Search Report and the Written Opinion dated Jun. 10, 2014 From the International Searching Authority Re. Application No. PCT/IL2014/050089.
International Search Report and the Written Opinion dated May 15, 2014 From the International Searching Authority Re. Application No. PCT/IL2014/050090.
International Search Report and the Written Opinion dated Feb. 20, 2015 From the International Searching Authority Re. Application No. PCT/IB2014/064316.
International Search Report and the Written Opinion dated Feb. 25, 2015 From the International Searching Authority Re. Application No. PCT/1B2014/064319.
International Search Report and the Written Opinion dated Jul. 27, 2015 From the International Searching Authority Re. Application No. PCT/IB2015/050148.
International Search Report and the Written Opinion dated Jul. 28, 2014 From the International Searching Authority Re. Application No. PCT/IL2014/050246.
Invitation to Pay Additional Fees dated Apr. 10, 2014 From the International Searching Authority Re. Application No. PCT/IL2014/050090.
Invitation to Pay Additional Fees dated Dec. 16, 2014 From the International Searching Authority Re. Application No. PCT/IB2014/064319.
Invitation to Pay Additional Fees dated Dec. 23, 2014 From the International Searching Authority Re. Application No. PCT/IB2014/064316.
Arora "Recent Insights Into the Role of the Autonomic Nervous System in the Creation of Substrate for Atrial Fibrillation—Implications for Therapies Targeting the Atrial Autonomic Nervous System", Circulation: Arrhythmia and Electrophysiology, 5(4): 850-859, Aug. 1, 2012.
Arora et al. "Porcine Intrinsic Cardiac Ganglia", The Anatomical Record Part A, 271A: 249-258, 2003.
Biosensors International Group "D-SPECT™ Cardiac Imaging System", Biosensors International Group, Ltd., Product Description, 2 P., 2013.
Burnstock "Autonomic Neurotransmission: 60 Years Since Sir Henry Dale", The Annual Review of Pharmacology and Toxicology, 49: 1-30, 2009.
Esler et al. "Sympathetic Nerve Activity and Neurotransmitter Release in Humans: Translation From Pathophysiology Into Clinical Practice", Acta Physiologica Scandinavica, 177: 275-284, 2003.
Ghosh et al. "Assessment of Myocardial Ischaemia and Viability: Role of Positron Emission Tomography", European Heart Journal, XP055181382, 31(24): 2984-2995, Online Published-Ahead-of-Print Oct. 21, 2010. p. 2986, col. 1, p. 2990-2993, col. 2.
Hirsch et al. "Measuring Activity of the Autonomic Nervous System in Humans", Obesity Research, 11(1): 2-4, Jan. 2003.

(56) References Cited

OTHER PUBLICATIONS

Hu et al. "Dynamic Molecular Imaging of Cardiac Innervation Using a Dual Head Pinhole SPECT System", Lawrence Berkely National Laboratory, University of California, eScholarship, XP055214624, LBNL Report No. LBNL-60008, p. 1-54, May 23, 2008. Abstract, p. 16, Para 3-p. 20, Para 2, Figs.9, 10, Table 2.
IAEA "Technetium-99m Radiopharmaceuticals: Status amd Trends", IAEA, International Atomic Energy Agency Radioisotopes and Radiopharmaceuticals Series, 1: 1-378, 2009.
Knuepfer et al. "Direct Assessment of Organ Specific Sympathetic Nervous System Activity in Normal and Cardiovascular Disease States", Experimental Physiology, 95(1): 32-33, 2010.
Kosa et al. "Principles and Methods of Myocardial Perfusion Imaging", Chap.2: 33-57.
Langer et al. "PET and SPET Tracers for Mapping the Cardiac Nervous System", European Journal of Nuclear Medicine and Molecular Imaging, 29(3): 416-434, Mar. 2002.
Linz et al. "Atrial Autonomic Innervation: A Target for Interventional Antiarrhythmic Therapy?", Journal of the American College of Cardiology, JACC, p. 1-33, 2013.
Malliani et al. "Emerging Excitatory Role of Cardiovascular Sympathetic Afferents in Pathophysiological Conditions", Hypertension, 39: 63-68, Jan. 2002.
Malpas "Sympathetic Nervous System Overactivity and Its Role in the Development of Cardiovascular Disease", Physiology Review, 90: 513-557, 2010.
Matsunari et al. "Iodine-123 Metaiodobenzylguanidinen Imaging and Carbon-11 Hydroxyephedrine Positron Emission Tomography Compared in Patients With Left Ventricular Dysfunction", Circulation Cardiovascular Imaging, 3: 595-603, Sep. 2010.
Mourot et al. "Effects of the Cold Pressor Test on Cardiac Autonomic Control in Normal Subjects", Physiology Research, 58: 83-91, 2009.
Rabinovitch et al. "A Method of Dynamic Analysis of Iodine-123-Metaiodobenzylguanidine Scintigrams in Cardiac Mechanical Overload Hypertrophy and Failure", Journal of Nuclear Medicine, XP055214626, 34(4): 589-600, Apr. 1993. p. 589, col. 1-p. 593, col. 2, p. 598, col. 2-p. 599, col. 1.
Raffel et al. "Quantification of Cardiac Sympathetic Nerve Density With N-11C-Guanyl-Meta-Octopamine and Tracer Kinetic Analysis", The Journal of Nuclear Medicine, XP055214628, 54(9): 1645-1652, Published Online Jul. 25, 2013. p. 145, col. 1-p. 1647, col. 1, Figs.1, 2.
Rispler et al. "Quantitative 123I-MIBG SPECT/CT Assessment of Cardiac Sympathetic Innervation—A New Diagnostic Tool for Heart Failure", International Journal of Cardiology, XP028740607, 168(2): 1556-1558, Jan. 17, 2013, p. 1556, col. 1-p. 1558, col. 1.
Ross et al. "Research Applications of Selected [123]I-Labeled Neuroreceptor SPECT Imaging Ligands", Journal of Nuclear Medicine and Technology, 32(4): 209-214, Dec. 2004.
Sasano et al. "Abnormal Sympathetic Innervation of Viable Myocardium and the Substrate of Ventricular Tachycardia After Myocardial Infarction", Journal of the American College of Cardiology, 51(23): 2266-2275, Jun. 10, 2008.
Sciagra et al. "Rest-Redistribution Thallium-201 SPECT to Detect Myocardial Viability", The Journal of Nuclear Medicine, XP055181381, 39(3): 384-390, Mar. 1998. p .384-p. 389, Abstract/39/3/384, p. 384-p. 389.
Sen "Some Observations of Decapsulation and Denervation of the Kidney", The British Journal of Urology, 8(4): 319-328, 1936.
Singh "Chemistry, Design, and Structure-Activity Relationship of Cocaine Antagonists", Chemical Reviews, 100: 925-1024, 2000.
Sisson et al. "Metaiodobenzylguanidine to Map Scintigraphically the Adrenergic Nervous System in Man", The Journal of Nuclear Medicine, 28(10): 1625-1636, Oct. 1987.
Smith "Extrinsic Inputs to Intrinsic Neurons in the Porcine Heart In Vitro", The American Journal of Physiology, 276(2/Pt.2): R455-R467, Feb. 1999.
Smith et al. "Simulation of Cardiovascular System Diseases by Including the Autonomic Nervous System Into a Mineral Model", Computer Methods and Programs in Biomedicine, 86(2): 153-160, May 2007.
Stefanelli et al. "[123]I-MIBG Scintigraphy as a Powerful Tool to Plan an Implantable Cardioverter Defibrillator and to Assess Cardiac Resynchronization Therapy in Heart Failure Patients", International Journal of Molecular Imaging, XP055214933, 2012: 1-6, Published Online Sep. 26, 2012. Abstract, p. 1, col. 1-p. 2, col. 1.
Tan et al. "Autonomic Nerves in Pulmonary Veins", Heart Rythm, 4(3 Suppl.): S57-S60, Mar. 2007.
Travin "Cardiac Autonomic Imaging With SPECT Tracers", Journal of Nuclear Cardiology, 20(1): 128-143, Feb. 2013.
Troisi et al. "Relation of Obesity and Diet Sympathetic Nervous System Activity", Hypertension, 17(5): 669-677, May 1991.
University of Ottawa View of NCT02071680 on Feb. 25, 2014: Nuclear Imaging Using 123I-mIBG (Adreview™ GE Healthcare) to Visually Identify Atrial Cardiac Innervation, ClinicalTrials.gov Archive, University of Ottawa Heart Insitute, XP0055214861, 4 P., Feb. 25, 2014. p. 1-3.
Vallabhajosula et al. "Radioiodinated Metaiodobenzylguanidine (MIBG): Radiochemistry, Biology, and Pharmacology", Seminars in Nuclear Medicine, 41: 324-333, 2011.
Vissing et al. "Stimulation of Skin Sympathetic Nerve Discharge by Central Command", Circulation Research, 69(1): 228-238, Jul. 1991.
Wong et al. "Pericardial Fat Is Associated With Atrial Fibrillation Severity and Ablation Outcome", Journal of the American College of Cardiology, JACC, 57(17): 1745-1751, 2011.
Zhang et al. "The Celiac Ganglia. Anatomic Study Using MRI in Cadavers", American Journal of Roentgenology, AJR, 186(6): 1520-1523, Jun. 2006.
Notification of Office Action and Search Report dated Dec. 2, 2016 From the State Intellectual Property Office of the People's Republic of China Re. Application No. 201480005617.0 and Its Summary in English.
Supplementary European Search Report and the European Search Opinion dated Feb. 9, 2016 From the European Patent Office Re. Application No. 14743909.5. (9 Pages).
Abi-Jaoudeh et al. "Multimocality Image Fusion-Guided Procedures: Technique, Accuracy, and Applications", Cardiovascular and Interventional Radiology, 35(5): 986-998, Published Online Aug. 1, 2012.
Bercier et al. "Multimodality Image Fusion for Radiosurgery Localisation of Large AVMs", Proceedings of the 22nd Annual International Conference of the IEEE Engineering in Medicine and Biology Society, EMBS, Chicago, IL, USA, Jul. 23-29, 2000, XP002422677, 4: 2689-2692, Jul. 23, 2000.
Gering et al. "An Integrated Visualization System for Surgical Planning and Guidance Using Image Fusion and an Open MR", Journal of Magnetic Resonance Imaging, XP002239881, 13(6): 967-975, Jun. 2001.
Levin et al. "Techniques for Efficient, Real-Time, 3D Visualization of Multi-Modality Cardiac Data Using Consumer Graphics Hardware", Computerized Medical Imaging and Graphics, 29(6): 463-475, Sep. 30, 2005.
Mallouhi et al. "3 T MR Tomography of the Brachial Plexus: Structural and Microstructural Evaluation", European Journal of Radiology, 81(9): 2231-2245, Sep. 30, 2012.
Manssour et al. "Visualizing Inner Structures in Multimodel Volume Data", Proceesings of the 15th Brazilian Symposium on Computer Graphics and Image Processing (SIBGRAPI'02), Oct. 7-10, 2002, p. 51-58, Oct. 7, 2002.
San Mauro et al. "Nerves of the Heart: A Comprehensive Review With a Clinical Point of View", Neuroanatomy, 8: 28-31, 2009.
Restriction Official Action dated Dec. 28, 2017 From the US Patent and Trademark Office Re. U.S. Appl. No. 14/774,202. (6 pages).
Official Action dated Aug. 10, 2017 From the US Patent and Trademark Office Re. U.S. Appl. No. 14/762,933. (47 pages).
Official Action dated Jun. 26, 2017 From the US Patent and Trademark Office Re. U.S. Appl. No. 14/917,285. (35 pages).
Unknown "SPECT CT Fusion Image", Imaging Diagnosis in Nuclear Medicine, 24(1): 52-59, 2009. Partial English Translation.

(56) References Cited

OTHER PUBLICATIONS

Notice of Reason for Rejection dated May 9, 2017 From the Japan Patent Office Re. Application No. 2015-554307 and Its Translation Into English. (16 Pages).
Katafuchi "Cardiac Radionuclide Imaging", Japanese Journal of Radiological Technology, 64(5): 626-637, 2008. & English Abstract.
Klein et al. "Abstract 17871: Assessment of Global Cardiac Innervation Using 1123-Meta-Iodobenzylguanidine Before and After Ventricular Tachycardia Ablation", Circulation, 126(Suppl.21): # 17871, Nov. 20, 2012.
Shoda "Catheter Ablation for Atrial Fibrillation in Patients With Heart Failure", Japanese Journal of Electrocardiology, 31(2): 205-207, 2011.
Sumiyoshi "New Diagnostic Methods and Non Pharmacological Therapies in Cardiac Arrhythmias", Juntendo Medical Journal, 42(4): 450-458, 1997.
Flotats et al. "Proposal for Standardization of 1231-Metaiodobenzylguanidine (MIBG) Cardiac Sympathetic Imaging by the the EANM Cordiovascular Committee and European Council of Cardiology", European Journal of Nuclear Medicine and Molecular Imaging, 37(9): 1802-1812, Aug. 2010.
Wang et al. "Metaiodobenzylguanidine Myocardial Imaging and the Application Thereof", Foreign Medical Sciences, Section of Internal Medicine, 28(5): 081511165-E-1-081511165-E-8, May 2001. & English Translation.
Official Action dated Jan. 6, 2017 From the US Patent and Trademark Office Re. U.S. Appl. No. 14/762,933. (55 pages).
Notice of Rejection dated May 8, 2018 From the Japan Patent Office Re. Application No. 2015-554307 and Its Translation Into English. (12 Pages).
Armour et al. "Gross and Microscopic Anatomy of the Human Intrinsic Cardiac Nervous System", The Anatomical Record, 247(2): 289-298, Feb. 1997.
Restriction Official Action dated May 8, 2018 From the US Patent and Trademark Office Re. U.S. Appl. No. 14/762,838. (8 pages).
International Preliminary Report on Patentability dated Dec. 8, 2016 From the International Bureau of WIPO Re. Application No. PCT/IB2015/053984. (11 Pages).
Decision of Rejection dated Feb. 26, 2018 From the State Intellectual Property Office of the People's Republic of China Re. Application No. 201480005566.1. (8 Pages).
Official Action dated Mar. 28, 2018 From the US Patent and Trademark Office Re. U.S. Appl. No. 14/774,202. (48 pages).
Applicant-Initiated Interview Summary dated Aug. 27, 2018 From the US Patent and Trademark Office Re. U.S. Appl. No. 14/774,202. (4 pages).
Official Action dated Aug. 16, 2018 From the US Patent and Trademark Office Re. U.S. Appl. No. 14/762,838. (75 pages).
Official Action dated Aug. 24, 2018 From the US Patent and Trademark Office Re. U.S. Appl. No. 14/762,932. (70 pages).
Official Action dated Dec. 26, 2018 From the US Patent and Trademark Office Re. U.S. Appl. No. 14/774,202. (22 pages).
Summons to Attend Oral Proceedings Pursuant to Rule 115(1) EPC Dated Jun. 14, 2019 From the European Patent Office Re. Application No. 14763161.8. (6 Pages).
Official Action dated Mar. 14, 2019 From the US Patent and Trademark Office Re. U.S. Appl. No. 14/762,838. (27 pages).
Official Action dated Mar. 14, 2019 From the US Patent and Trademark Office Re. U.S. Appl. No. 14/762,932. (20 pages).
Rozovsky et al. "Added Value of SPECT/CT for Correlation of MIBG Scintigraphy and Diagnostic CT in Neuroblastoma and Pheochromocytoma", American Journal of Roentgenology, 190: 1085-1090, Apr. 2008.
Decision to Refuse a European Patent dated Mar. 16, 2020 From the European Patent Office Re. Application No. 14763161.8. (28 Pages).
Provision of the Minutes in Accordance With Rule 124(4) EPC Dated Mar. 6, 2020 From the European Patent Office Re. Application No. 14763161.8. (4 Pages).
Decision of Rejection dated Sep. 24, 2019 From the China National Intellectual Property Administration Re. Application No. 201480013510.0 and Its Summary in English. (15 Pages).
Official Action dated Oct. 25, 2019 From the US Patent and Trademark Office Re. U.S. Appl. No. 14/762,838. (34 Pages).
Official Action dated Oct. 28, 2019 From the US Patent and Trademark Office Re. U.S. Appl. No. 14/762,932. (16 Pages).
Official Action dated Sep. 30, 2019 From the US Patent and Trademark Office Re. U.S. Appl. No. 14/774,202. (19 pages).
Schwaiger et al. "Noninvasive Evaluation of Sympathetic Nervous System in Human Heart by Positron Emission Tomography", Circulation, 82(2), 457-464, Aug. 1990.
Final Official Action dated May 14, 2020 from the US Patent and Trademark Office Re. U.S. Appl. No. 14/762,838. (34 pages).
Final Official Action dated May 14, 2020 from the US Patent and Trademark Office Re. U.S. Appl. No. 14/762,932. (27 pages).
Final Official Action dated Jun. 18, 2020 from the US Patent and Trademark Office Re. U.S. Appl. No. 14/774,202. (19 pages).
Communication Pursuant to Article 94(3) EPC Dated Oct. 16, 2020 From the European Patent Office Re. Application No. 14743288.4. (5 pages).
Official Action Dated Dec. 11, 2020 from the US Patent and Trademark Office Re. Application No. 14/762,838. (37 pages).
Official Action Dated Nov. 27, 2020 From the US Patent and Trademark Office Re. Application No. 14/762,932. (30 pages).

* cited by examiner

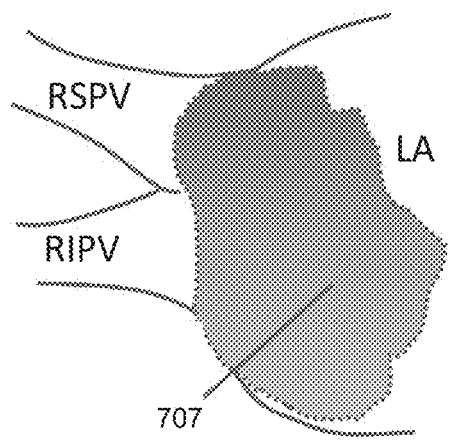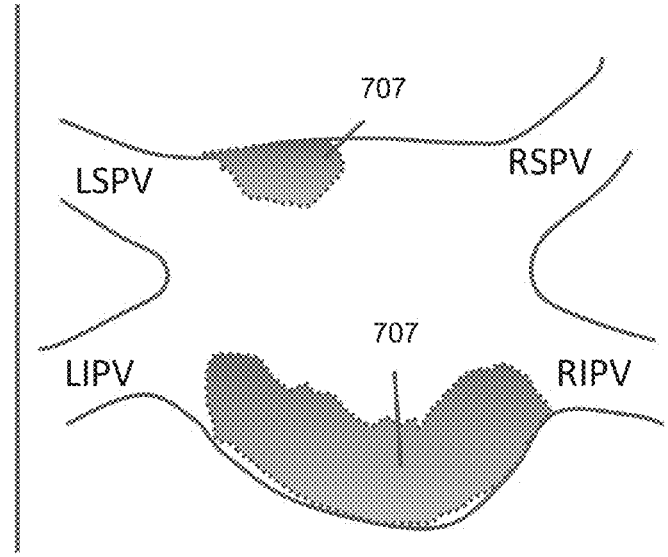
FIG. 7A        FIG. 7B
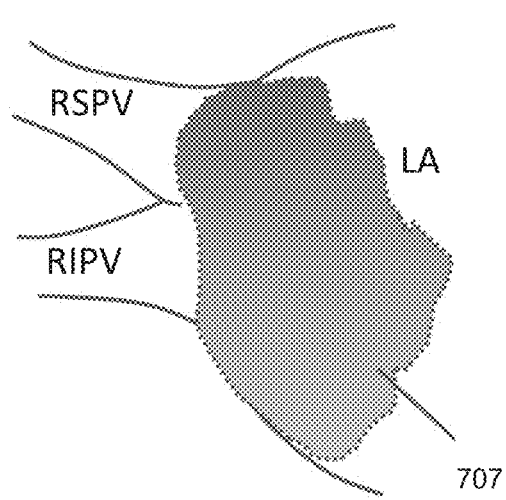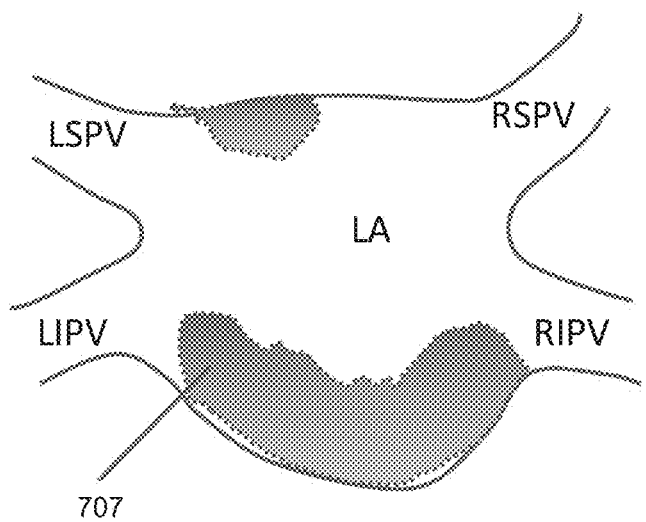
FIG. 7C        FIG. 7D

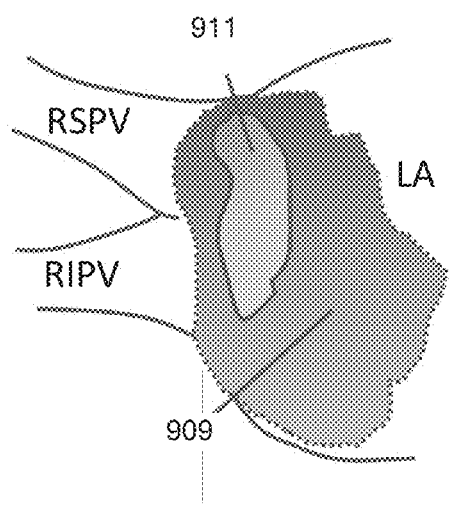
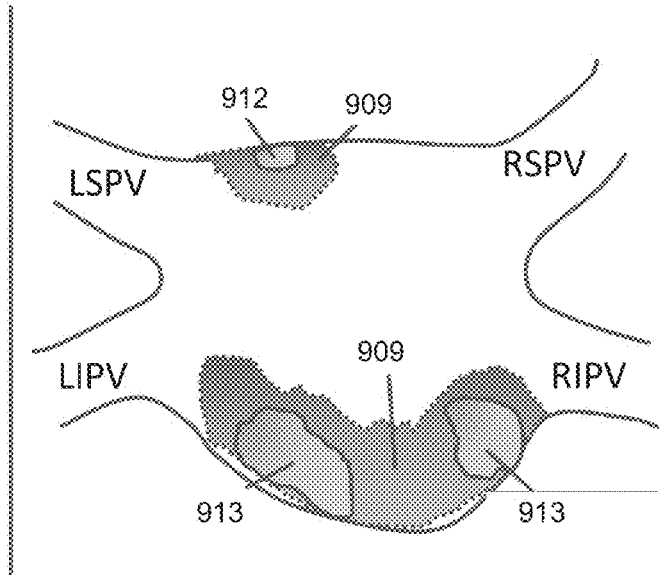
FIG. 8A  FIG. 8B
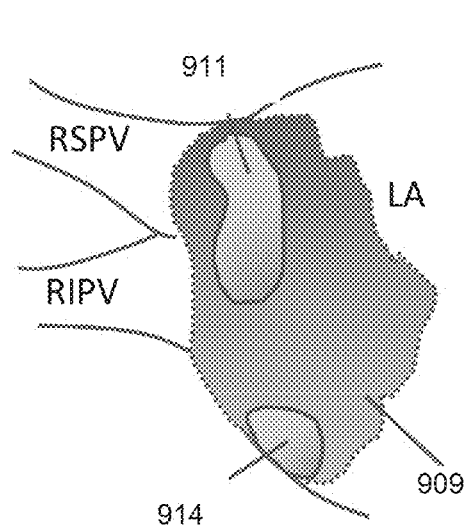
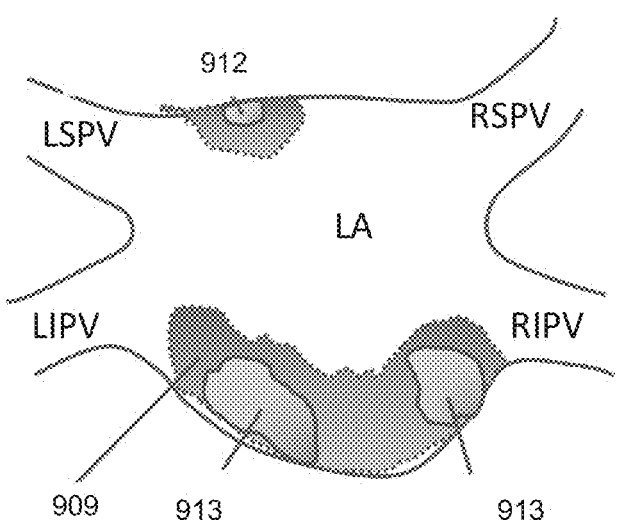
FIG. 8C  FIG. 8D

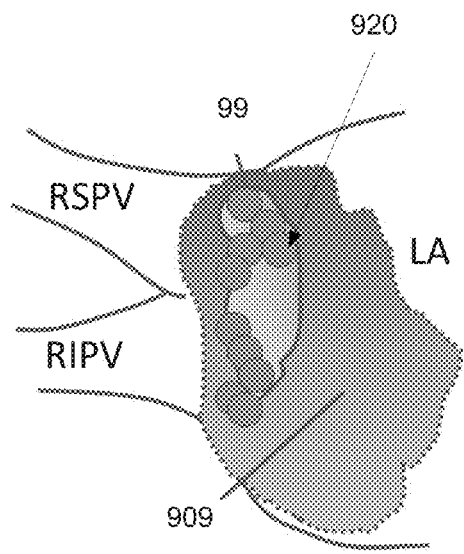
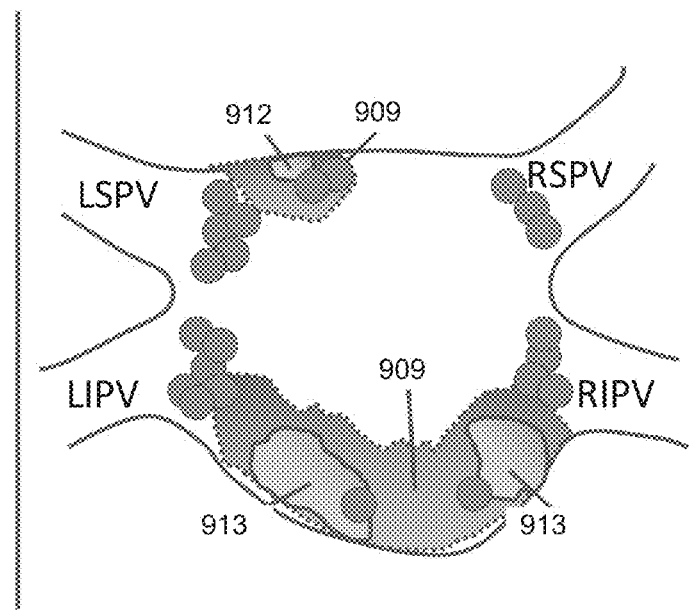
FIG. 9A  FIG. 9B
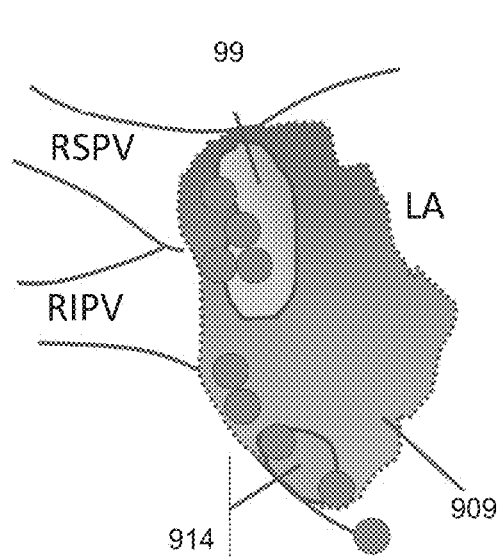
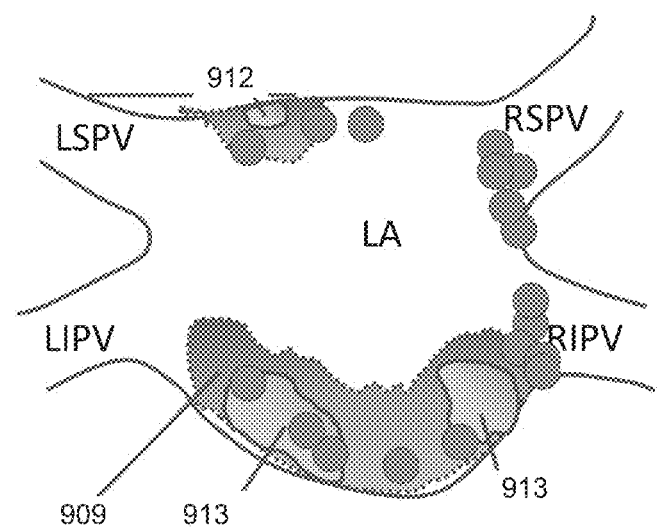
FIG. 9C  FIG. 9D

FIG. 16: Pre HFS mIBG uptake of LA
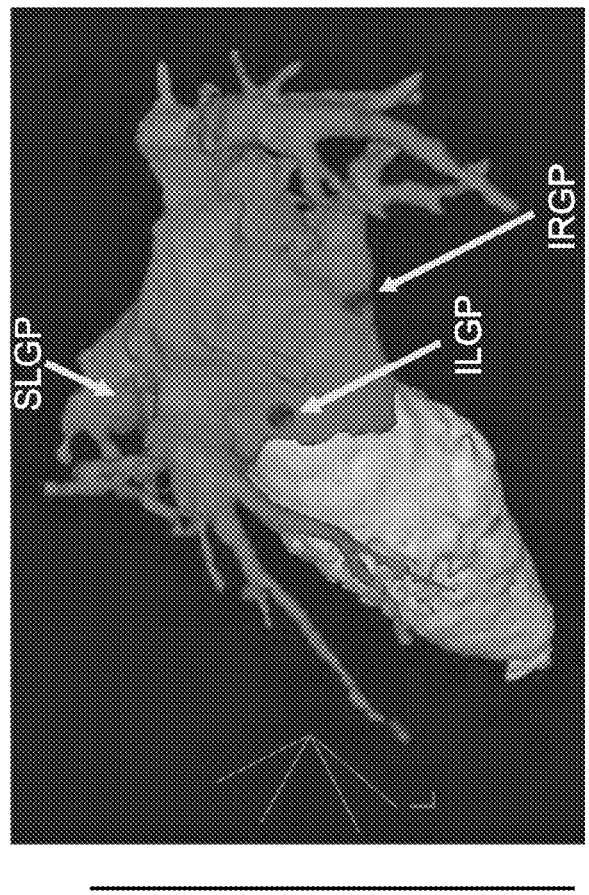
PA view
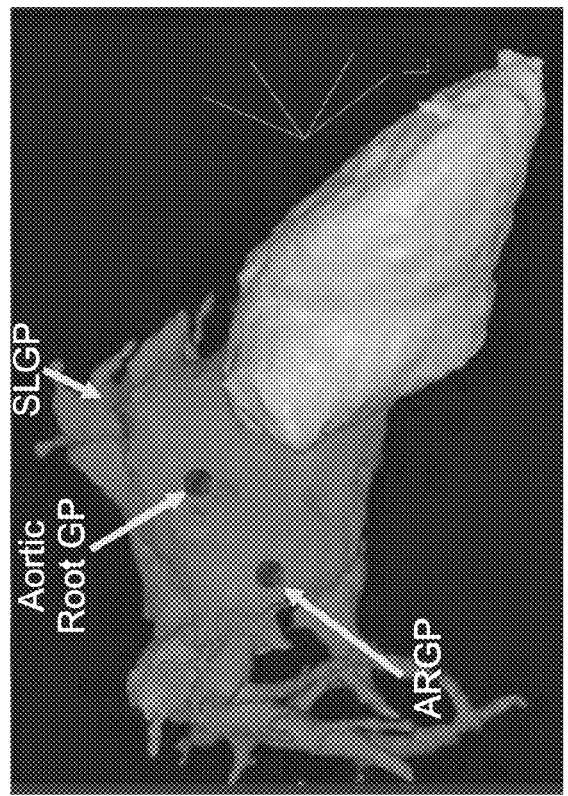
RAO view
● Epicardial GP FIG. 17: Pre HFS saturated image
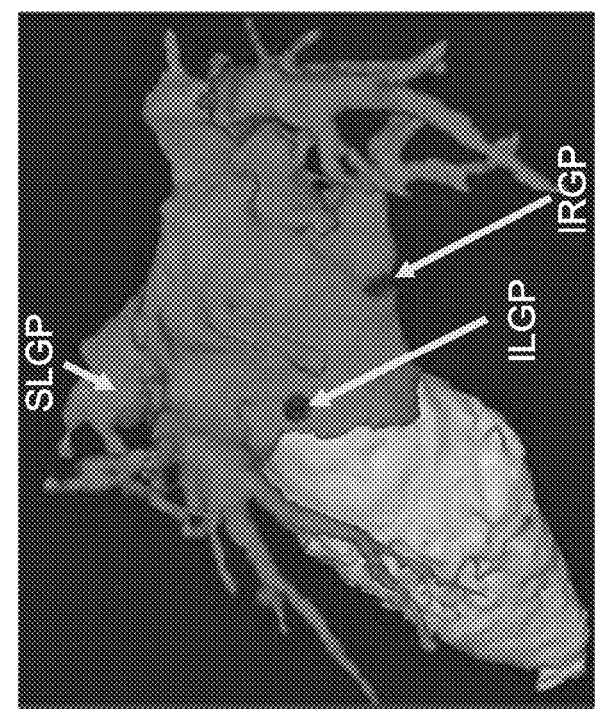
PA view
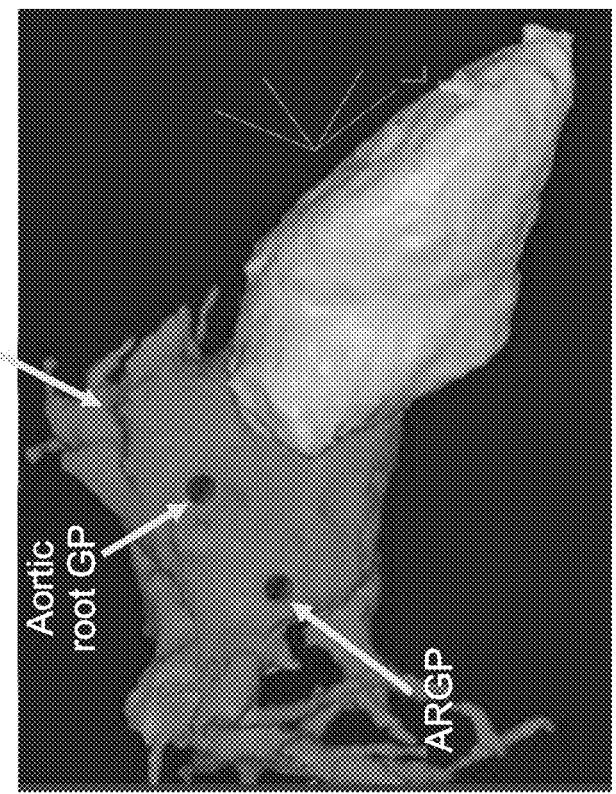
RAO view
● Epicardial GP FIG. 18: HFS pre ablation procedure
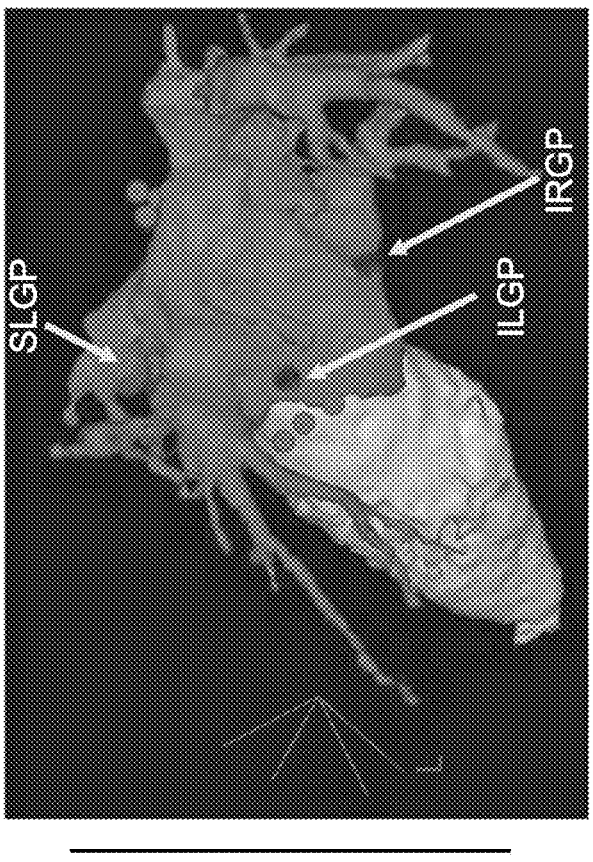
PA view
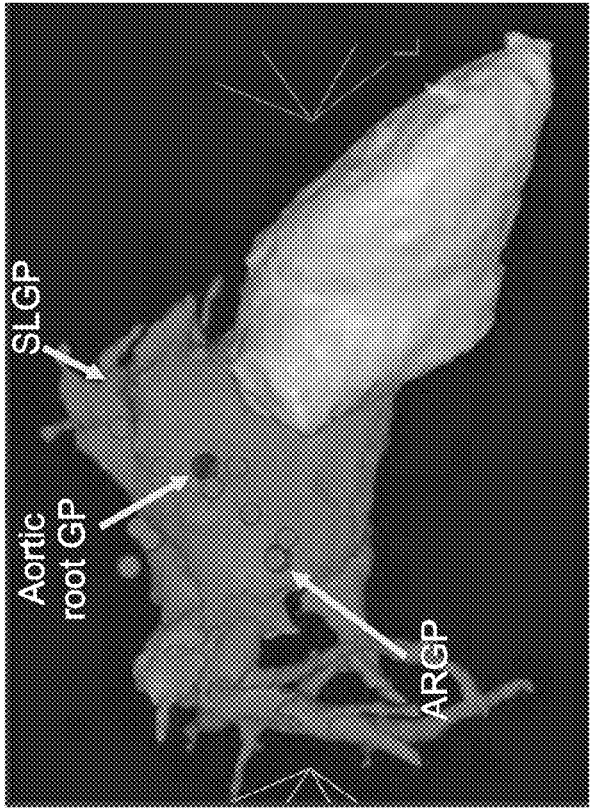
RAO view
● + HFS

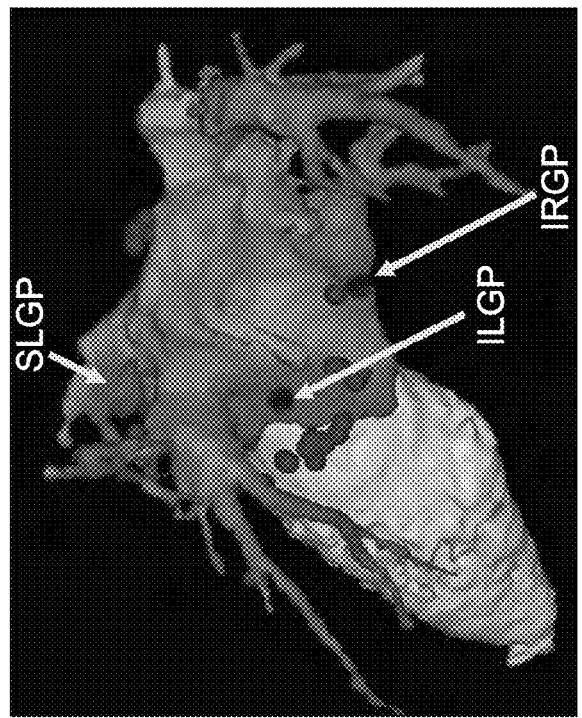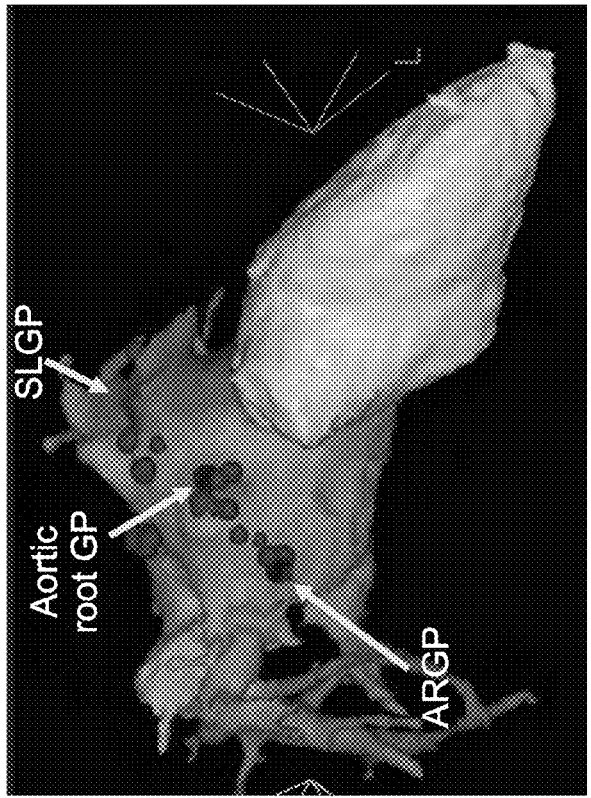
FIG. 19: Ablation procedure

FIG. 20: HFS post ablation procedure
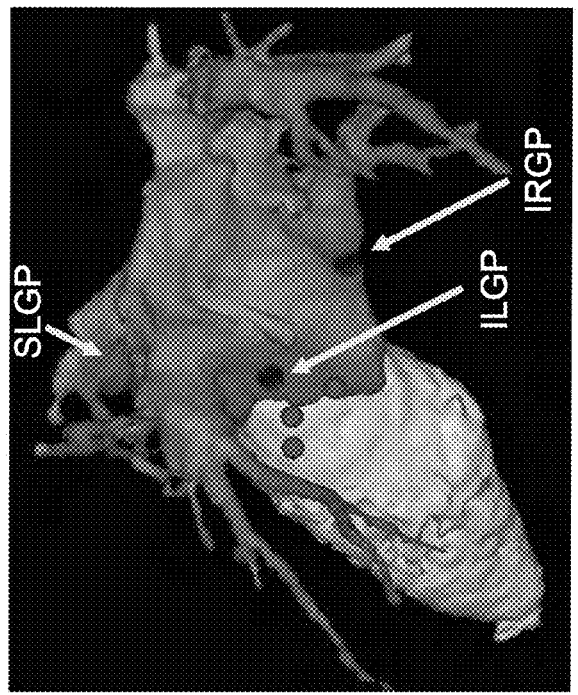
PA view
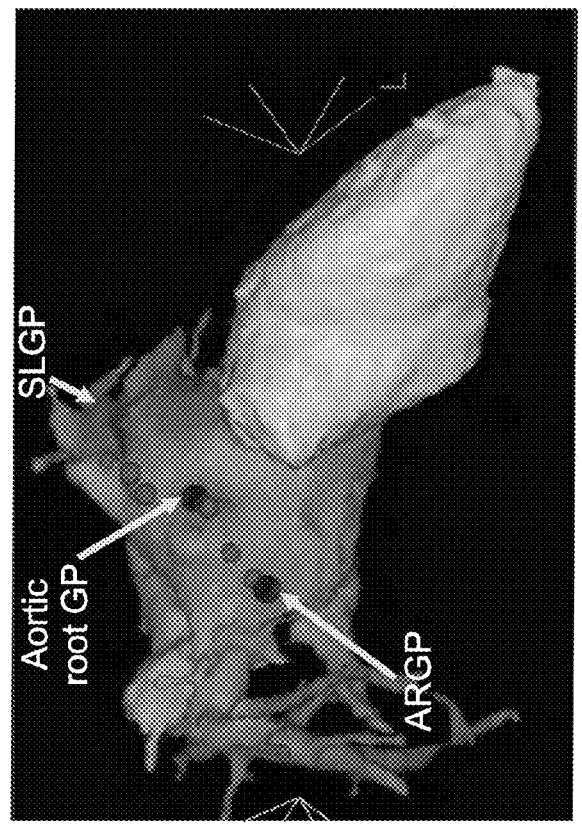
RAO view

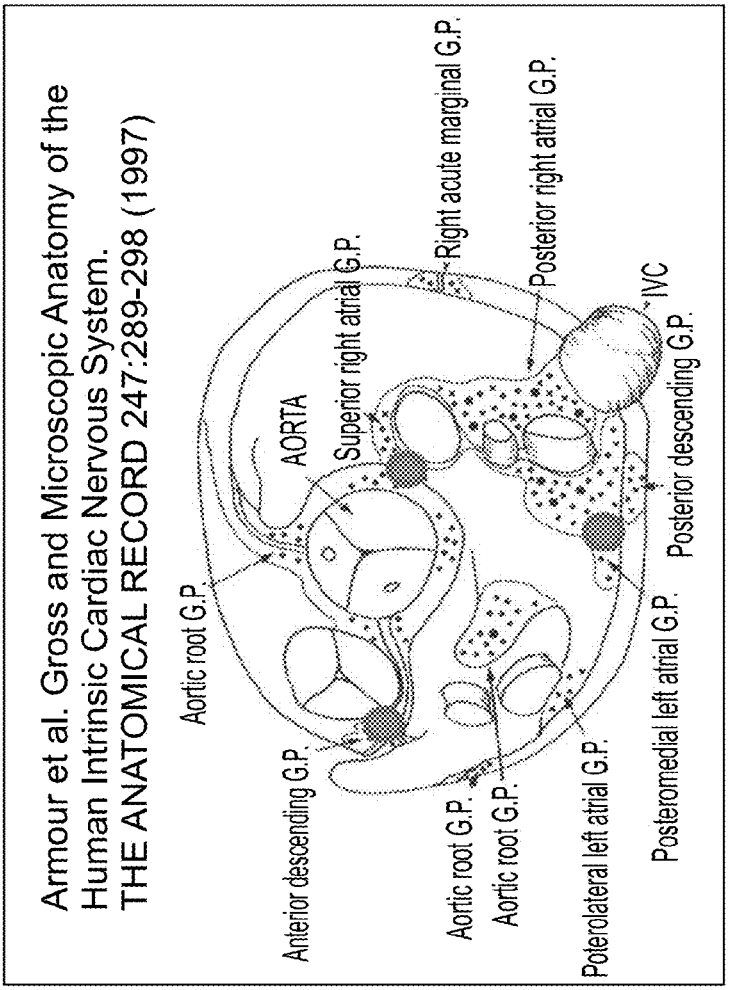
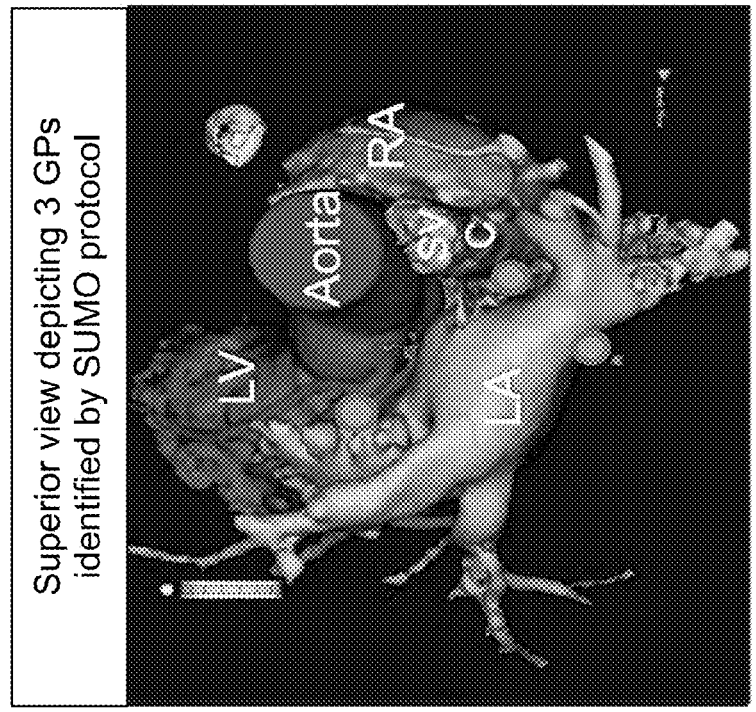
FIG. 22B
FIG. 22A

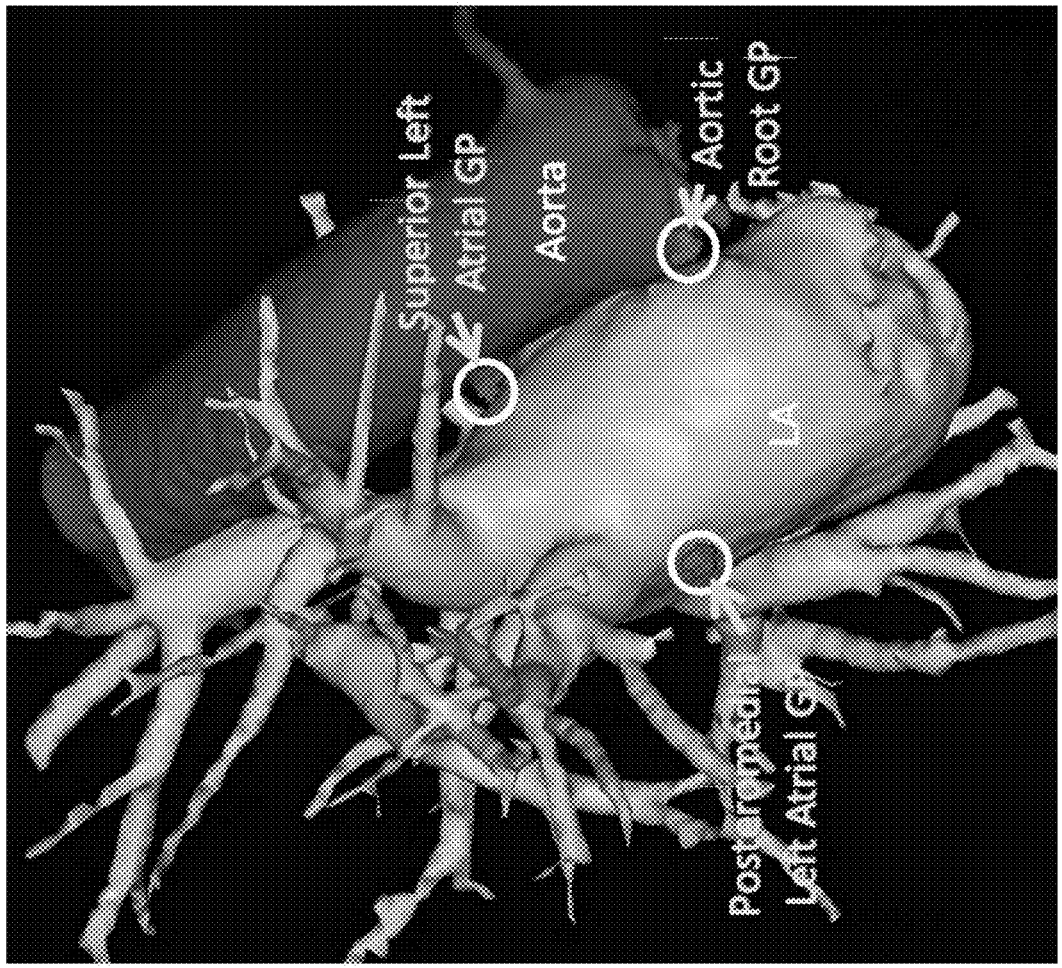
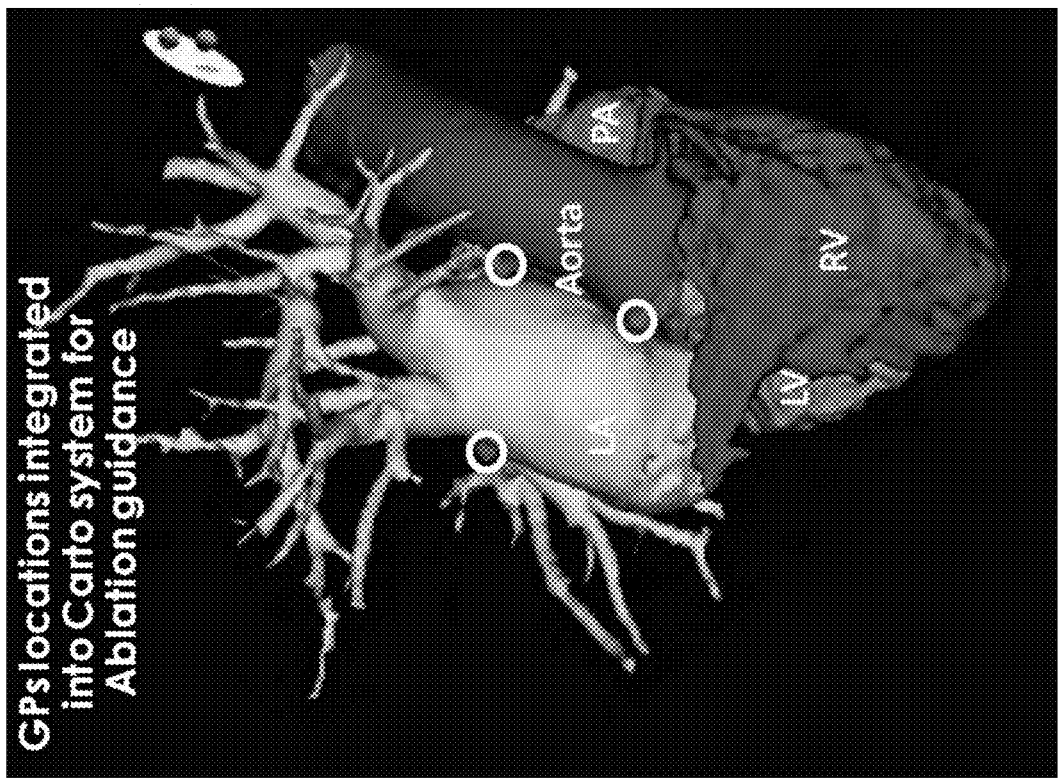
FIG. 24

BODY STRUCTURE IMAGING

RELATED APPLICATIONS

This application is a National Phase of PCT Patent Application No. PCT/IL2014/050088 having International filing date of Jan. 24, 2014, which claims the benefit of priority under 35 USC § 119(e) of U.S. Provisional Patent Application Nos. 61/756,112 filed on Jan. 24, 2013, 61/776,599 filed on Mar. 11, 2013, 61/803,611 filed on Mar. 20, 2013, 61/831,664 filed on Jun. 6, 2013, 61/875,069 filed on Sep. 8, 2013, 61/875,074 filed on Sep. 8, 2013, and 61/875,070 filed on Sep. 8, 2013. The contents of the above applications are all incorporated by reference as if fully set forth herein in their entirety.

PCT Patent Application No. PCT/IL2014/050088 is one of a set including the following PCT Applications:
PCT Patent Application No. PCT/IL2014/050088 having International filing date of Jan. 24, 2014, and titled "BODY STRUCTURE IMAGING";
PCT Patent Application No. PCT/IL2014/050086 having International filing date of Jan. 24, 2014, and titled "BODY STRUCTURE IMAGING";
PCT Patent Application No. PCT/IL2014/050090 having International filing date of Jan. 24, 2014, and titled "NERVE IMAGING AND TREATMENT";
PCT Patent Application No. PCT/IL2014/050089 having International filing date of Jan. 24, 2014, and titled "BODY STRUCTURE IMAGING";
all of which are cofiled on the same date as PCT Patent Application No. PCT/IL2014/050088.

FIELD AND BACKGROUND OF THE INVENTION

The present invention, in some embodiments thereof, relates to methods and systems of imaging and, more particularly, but not exclusively, to methods and systems of medical localizing and monitoring as well as to imaging using a functional imaging modality, e.g., a single photon emission computed tomography (SPECT) and/or positron emission tomography (PET).

Volumetric scans such as CAT scans, positron emission tomography (PET) scans, computerized tomography (CT) scans, magnetic resonance imaging (MRI) scans, Ultrasound scans, laser three dimensional (3D) scanners, and the like are commonly used, particularly in the medical industry, to observe objects within a structure that would otherwise be unobservable. These scans have greatly advanced the capability of professionals such as physicians. Conventional volumetric scan is intended to produce a volumetric image of a large volume of the body at high resolution. The ability to perform a volumetric scan with high resolution requires a large number of detectors, a fine motion control, and abundant processing resources for allowing the acquisition of a high resolution volumetric image in a reasonable time. Furthermore, when the volumetric scan images a relatively large area, such as the torso, the patient radiation dose is relatively high, for example when the volumetric scan is a CT scan.

Usually, volumetric imaging of a body structure is a multi-stage process. First biochemical, radioactive and/or contrast agents may be administered. Then, measurements are taken at a set of predetermined views at predetermined locations, orientations, and durations. Then, the data is analyzed to reconstruct a volumetric image of the body structure and an image of the body structure is formed. The imaging process is sequential, and there is no assessment of the quality of the reconstructed image until after the measurement process is completed. Where a poor quality image is obtained, the measurements must be repeated, resulting in inconvenience to the patient and inefficiency in the imaging process.

The volumetric scan is usually performed by orbiting detectors from multiple directions in order to provide sufficient information to reconstruct a three-dimensional image of the radiation source by means of computed tomography. The detectors are typically mounted on a gantry to provide structural support and to orbit the detector around the object of interest. If the detector is a nuclear medicine detector, such as scintillation detector or CZT detectors, for example single photon emission computed tomography (SPECT) and positron emission tomography (PET) systems detector, a collimator that is used to restrict radiation acceptance, or the direction of ray travel, is placed between the detector and the object being imaged. Typically this collimator is constructed to provide a multiplicity of small holes in a dense, high-atomic-number material such as lead or Tungsten. The rays will pass through the holes if they travel in a direction aligned with the hole but will tend to be absorbed by the collimator material if they travel in a direction not aligned with the holes.

SUMMARY OF THE INVENTION

There is provided, in accordance with some embodiments of the present invention, methods and systems for locating objects of desired shape (e.g., tissue, nerves, cancer) based on a functional image obtained from a functional imaging modality of an intra-body volume of a patient. Optionally, the functional image is combined with an anatomical image, and the nerve tissue is located based on the combined images. Optionally the object of desired shape is detected using a model of nearby tissue.

According to an aspect of some embodiments of the present invention there is provided a method of medical image processing for images of body structures, comprising: receiving anatomical data to reconstruct an anatomical image of a region of a body of a patient, said region comprises a portion of at least one internal body part which borders or is spaced apart from a target tissue; receiving functional data from a functional imaging modality which images at least said portion of the region of the body of the patient; processing said anatomical image to generate at least one image mask corresponding to the zone outside of the wall of said at least one internal body part; correlating the at least one generated image mask with the functional data for guiding a reconstruction of a functional image depicting said target tissue; and providing the reconstructed functional image.

Optionally, the target tissue is a nerve tissue.

Optionally, the anatomical data is obtained form an anatomical imaging modality.

Optionally, the at least one image mask is generated based on preselected anatomical considerations of the at least one internal body part that contain target nerve tissue that have intensity activity registered within the functional data.

Optionally, the at least one image mask is generated based on templates that define the location of target nerve tissue within and/or in proximal to the at least one internal body part.

Optionally, the method further comprises adjusting the shape of the image mask based on functional data readings from corresponding anatomical data that does not include target nerve tissue.

Optionally, the image masks are generated based on anatomical locations of target nerve structures with different levels of functional sensitivity to a radioagent.

Optionally, the method further comprises normalizing the functional data based on measurements denoting activity of the target nerve tissue.

Optionally, the method further comprises removing functional data denoting noise from anatomical regions that do not contain target nerve tissue based on the anatomical data of the regions that do not contain target nerve tissue.

Optionally, the reconstructed functional image contains regions where the target nerve structures are located and/or precise coordinates of the target nerve structures.

Optionally, there are two image cutters, one for the wall of the body structure and another for the outside of the wall of the body structure, the two image cutters being different from each other.

Optionally, the method further comprises correlating target nerves with tissue types.

Optionally, the method further comprises identifying the target nerve structures based on at least one predefined rule.

Optionally, the at least one predefined rule comprises being larger than a 2D or 3D size.

Optionally, the at least one predefined rule comprises comparing a radio labeled molecule activity level compared to an average value and/or standard deviation of molecular activity level across at least one of: the organ volume, within the image mask.

Optionally, the radio labeled molecule is metaiodobenzylguanidine (mIBG).

Optionally, the method further comprises calculating at least one parameter for the identified target nerve structures.

Optionally, the image mask is a mapping of a 3D volume or 2D area, for correlating a volume or an area of the anatomical image to the corresponding functional image.

Optionally, the functional imaging modality is a single photon emission computed tomography (SPECT) modality.

Optionally, the anatomical imaging modality is selected from the group comprising: computed tomography (CT), 3D ultrasound (US), 2D US, magnetic resonance imaging (MRI).

Optionally, the method further comprises applying the image mask to a registration of the anatomical image and the functional image.

Optionally, the method further comprises segmenting the anatomical image into different regions to generate the image masks for detecting different GPs within the segmented regions.

Optionally, the method further comprises generating the at least one image mask based on the segments.

Optionally, a plurality of different sets of image masks are generated to correspond to different parts of the structure of the internal body part containing nerves.

Optionally, a plurality of image masks are generated to detect different nerve structures of different types and/or at different locations.

Optionally, the method further comprises calculating functional activity within the at least one generated image mask correlated with the functional data, and normalizing the calculated functional activity.

Optionally, the method further comprises registering the reconstructed functional image with a navigation system for one or both of treatment and diagnosis.

Optionally, the method further comprises generating a spatial connectivity map of the identified nerve structures that illustrates the relative spatial relationship between nerve structures.

Optionally, the method further comprises combining nerve structures identified based on different image masks, into a single dataset of at least some identified nerve structures.

Optionally, the anatomical image denotes structures of tissues innervated by nerves.

Optionally, the functional image denotes functional activity of the nerves innervating a tissue structure.

Optionally, the size and shape of the image masks are generated to contain target nerves innervating a tissue structure.

Optionally, correlating further comprises positioning the at least one image mask to correspond with regions of the target nerve tissue within the functional image.

Optionally, the method is repeated for different time frames and a single reconstructed image is generated.

Optionally, the anatomical images are obtained during a cyclic physiological process, wherein different spatiotemporal image masks are generated for images obtained during different phases of the physiological process, the different spatiotemporal image masks are synchronized with the physiological process to correspond to the same location of the tissues.

Optionally, the anatomical images obtained during a cyclic physiological process are registered, morphed, and a single set of image masks are generated.

Optionally, the size of the image masks for a hollow organ are selected based on the thickness of the organ wall.

Optionally, the method is performed before an ablation treatment of the tissue, to identify the location of the tissue.

According to an aspect of some embodiments of the present invention there is provided a method of medical image processing for images of nerve tissue of an ANS of a heart, comprising: receiving anatomical image data to reconstruct an anatomical image of heart structures innervated by the ANS; receiving a functional data from a functional imaging modality which images at least the heart structures innervated by the ANS; selecting at least one image mask by processing the anatomical image, the at least one image mask corresponding to dimensions of heart chamber walls containing nerve tissues; applying the at least one selected image mask with the functional data for guiding a reconstruction of a functional image depicting the GPs; and providing the reconstructed functional image.

Optionally, the nerve tissues are GPs.

Optionally, the at least one image mask is oversized compared to the heart wall chamber.

Optionally, the at least one image mask is generated based on preselected anatomical regions of the heart that contain target nerve tissue that have intensity activity registered within the functional data.

Optionally, the at least one image mask is generated based on templates that define the location of GPs in proximity to heart chamber walls.

Optionally, the at least one image mask is generated based on templates that define the location of GPs within heart chamber walls.

Optionally, the at least one image mask is generated based on templates that define the location of GPs that are located more than about 2 mm from the heart chamber walls.

Optionally, the method further comprises adjusting the shape of the image mask based on functional data readings from corresponding anatomical data of blood chambers and/or vessels that do not include GPs.

Optionally, the method further comprises cancelling functional data denoting noise from inside blood filled chambers and/or vessels of the heart based on the anatomical data.

Optionally, the functional imaging modality is SPECT and the anatomical imaging modality is at least one of CT and MRI.

Optionally, the anatomical images are obtained during a cardiac cycle, wherein different spatiotemporal image masks are selected for at least some images obtained during the cardiac cycle, the different spatiotemporal image masks are synchronized with the cardiac cycle to correspond to the same location of the heart.

Optionally, the anatomical image is an average image composed of the end diastolic volume image and the end systolic volume image.

Optionally, the method further comprises segmenting the anatomical image into walls of the heart chambers.

Optionally, the method further comprises selecting the at least one image mask based on the heart chamber wall segments.

Optionally, a first set of image masks is selected to correspond to an epicardium and tissue outside the myocardium, and a second set of image masks is selected to correspond to the myocardium.

Optionally, the method further comprises calculating functional activity within correlated image masks, and normalizing the calculated activity to identify the GPs.

Optionally, the functional activity is calculated for all image masks within the volume of the heart.

Optionally, the method further comprises identifying GPs based on at least one predefine rule comprising the GP being larger than a predefined size.

Optionally, the predefined sizes are different for epicardial GPs located within an epicardium and myocardial GPs located within a myocardium.

Optionally, the method further comprises identifying GPs based on at least one predefine rule comprising calculated activity above a predefined threshold.

Optionally, the predefined threshold is based on a predefined factor times a calculated standard deviation of activity within the image mask above a calculated average activity within the image mask, and the calculated adjacent activity surrounding an active region is lower than half of the activity of the active region.

Optionally, the method further comprises calculating at least one parameter for identified GPs.

Optionally, the at least one parameter is selected from one or more of: average size, specific activity, power spectra, normalized power spectra and GP connectivity map, number of GPs per predefined area.

Optionally, the at least one parameter is calculated for at least one image of the cardiac cycle.

Optionally, the method further comprises identifying changes in the at least one parameter over time.

Optionally, the method further comprises displaying the identified GPs at least one image of multiple frames of a cardiac cycle.

Optionally, the method further comprises registering the identified GPs with a navigation system for treatment.

According to an aspect of some embodiments of the present invention there is provided a method of medical image processing for images of one or more ANS components, the method being carried out by at least one module programmed to carry out the steps of the method, which comprise: receiving anatomical data from an anatomical imaging modality to reconstruct an anatomical image of a region of a body of a patient, said region comprises a portion of at least one internal body part which borders or comprises an ANS component; receiving functional data from a functional imaging modality which imaged at least said portion of the region of the body of the patient;

processing said anatomical image to generate at least one image mask having dimensions that correspond to dimensions of said at least one internal body part; applying the at least one generated image mask with the functional data for reconstruction of a functional image depicting said ANS component; and identifying one or more ANS components in the functional image.

According to an aspect of some embodiments of the present invention there is provided a method of medical image processing for images of GPs of an ANS of a heart, the method being carried out by at least one module programmed to carry out the steps of the method, which comprise: receiving anatomical image data from an anatomical imaging modality to reconstruct an anatomical image of heart structures innervated by the ANS; receiving a functional data from a functional imaging modality which images at least the heart structures innervated by the ANS; generating at least one image mask by processing the anatomical image, the at least one image mask corresponding to dimensions of heart chamber walls containing GPs; applying the at least one selected image mask with the functional data for locating one or more GPs of an ANS of a heart.

According to an aspect of some embodiments of the present invention there is provided a method of guiding a cardiac treatment using a functional imaging modality, comprising: providing functional imaging modality data from a functional imaging modality which images an intrabody volume of a patient containing a heart, the patient having been injected with an imaging agent having a nervous tissue uptake by an autonomic nervous system (ANS) of the heart, the ANS comprising at least one GP; locating the at least one GP innervating the heart based on the functional imaging modality data; and providing the located at least one GP.

Optionally, the ANS comprises at least one GP comprising one or more of: superior left GP (SLGP), inferior left GP (ILGP), anterior right GP (ARGP), inferior right GP (IRGP), and Marshall GP.

Optionally, the ANS comprises two, three or more GPs from two or three or more of: superior left GP (SLGP), inferior left GP (ILGP), anterior right GP (ARGP), inferior right GP (IRGP), and Marshall GP.

Optionally, the method further comprises setting up a system for ablating the located at least one GP to treat cardiac disease based on improper activity of the located at least one GP.

Optionally, the cardiac disease comprises atrial fibrillation.

Optionally, the coordinates of the located GPs are loaded into an intrabody navigation system for displaying the location of the GPs relative to the treatment or other diagnosis EP catheter.

Optionally, the coordinates of the located GPs are loaded into a CARTO® system for displaying the location of the GPs relative to the treatment catheter of the CARTO® system.

Optionally, the method further comprises navigating a catheter within the patient based on the CARTO® system.

Optionally, the method further comprises functionally verifying treatment points for GP ablation based on the CARTO® system.

Optionally, the method further comprises ablating the located GPs with the CARTO® system.

Optionally, the method further comprises confirming ablation of the GPs with the CARTO® system.

Optionally, locating comprises locating the at least one GP in a fat pad or other surrounding tissue of the heart based on the functional imaging modality data.

Optionally, setting up the system comprises setting up the system for ablating the at least one GP within the fat pad without ablating most of the surrounding fat pad.

Optionally, the method further comprises acquiring anatomical imaging modality data from an anatomical image modality which images an intrabody volume of the patient containing the heart, and wherein locating comprises locating the at least one GP in the intrabody volume or next to the intrabody volume of the heart based on registration of the functional imaging modality data and the anatomical imaging modality data.

Optionally, the method further comprises marking the located at least one GP on the anatomical imaging modality data.

Optionally, the anatomical imaging modality data is acquired in real time during a treatment procedure by fluoroscopy, the locating is performed before and/or in real time during the treatment procedure by CT, and the location of the at least one GP is presented to an operator performing the treatment procedure.

Optionally, the method further comprises generating an ANS map comprising a distribution and/or activity of one or both of ANS synapses and GPs, and providing the ANS map for display.

Optionally, the ANS map is overlaid on a reconstructed anatomical image of the heart containing a treatment or imaging probe within the heart, within the same space as the reconstructed anatomical image and CARTO® mapping image.

Optionally, the locating comprises identifying an intersection between a complex fractionated atrial electrogram (CFAE) site and a contractile force (CF) site, the guiding comprises guiding the ablation of the intersection.

Optionally, the locating comprises identifying an intersection between a complex fractionated atrial electrogram (CFAE) site and a dominant frequency (DF) site, the guiding comprises guiding the ablation of the intersection.

Optionally, the locating comprises identifying an intersection between a complex fractionated atrial electrogram (CFAE) site and at least one GP, the guiding comprises guiding the ablation of the intersection.

Optionally, the locating comprises identifying an intersection between a complex fractionated atrial electrogram (CFAE) site, a dominant frequency (DF) and at least one GP, the guiding comprises guiding the ablation of the intersection.

Optionally, the locating comprises identifying an intersection between a complex fractionated atrial electrogram (CFAE) site, a contractile force (CF) site and at least one GP, the guiding comprises guiding the ablation of the intersection.

Optionally, the locating comprises imaging at least one GP and mapping around the located GP to verify the position of the GP.

Optionally, the method further comprises selecting a patient based on a hypothesis that the patient is suffering from improper activity of the heart ANS.

Optionally, acquiring comprises acquiring to contain data multiple frames during at least one cardiac cycle and reconstructing a single image.

Optionally, the method further comprises monitoring the effects of ablation on the heart.

Optionally, the method further comprises confirming effects of ablation based on a generated ANS model.

According to an aspect of some embodiments of the present invention there is provided a system for identifying ANS tissue within an image of a heart of a patient, the system comprising: a module for receiving functional imaging modality data from a functional imaging modality which images an intrabody volume of a patient containing a heart, the patient having been injected with an imaging agent having a nervous tissue uptake by an autonomic nervous system (ANS) of the heart, the ANS comprising at least one GP; a module for receiving anatomical imaging modality data from an anatomical imaging modality which images an intrabody volume of a patient containing the heart; a module for locating the at least one GP innervating the heart based on the functional imaging modality data; and a module for positioning the located at least one GP on the anatomical imaging data.

Optionally, the ANS comprises at least one GP comprising one or more of:

superior left GP (SLGP), inferior left GP (ILGP), anterior right GP (ARGP), inferior right GP (IRGP), and Marshall GP.

Optionally, the ANS comprises two, three or more GPs from two or three or more of: superior left GP (SLGP), inferior left GP (ILGP), anterior right GP (ARGP), inferior right GP (IRGP), and Marshall GP.

Optionally, the anatomical imaging modality data is received before and/or during a treatment procedure.

Optionally, the system further comprises a catheter cardiac navigation system, the catheter cardiac navigation system receiving and displaying the located nervous tissue for guiding the intra-body treatment probe within the heart to ablate the nervous tissue.

Optionally, the catheter cardiac navigation system is CARTO®.

Optionally, the catheter cardiac navigation system is a 3D electrophysiological (EP) system.

Optionally, the system further comprises an intra-body treatment probe for ablation of the nervous tissue within the heart.

Optionally, the intra-body treatment probe is at least one of a radiofrequency (RF) treatment probe, a cryosurgery treatment probe, and a probe that injects a toxin or medication.

Optionally, the system further comprises a diagnosis module for comparing the distribution of the imaged nervous tissue with one or more sets of expected distributions, and detecting abnormal synaptic distribution and/or activity based on the comparison.

Optionally, the system further comprises a tracking module for tracking changes in the distribution of the imaged nervous tissue over time.

Optionally, the system further comprises a repository for storing at least one of generated ANS models and diagnosis.

Optionally, the system further comprises a module for estimating the prediction of success of an ablation procedure based on measured uptake of the functional image.

Optionally, the system further comprises a user input element for receiving manual input from a user, and a treatment planning module for annotating the located nervous tissue based on the received manual input.

Optionally, the system further comprises a function verification module for at least one of stimulating a nervous tissue in a certain intrabody area and identifying one or more nervous responses in response to the stimulation.

Optionally, the system further comprises a module for comparing effects of stimulation of nervous tissue after treatment with effects of stimulation of nervous tissue before treatment, based on a generated ANS model, to confirm the treatment.

Optionally, the modules of the system are distributed.

According to an aspect of some embodiments of the present invention there is provided a system for identifying ANS components within an image of a heart of a patient, the system comprising: at least one module for: receiving functional imaging modality data from a functional imaging modality which images an intrabody volume of a patient containing a heart, the patient having been injected with an imaging agent having a nervous tissue uptake by an autonomic nervous system (ANS) of the heart, the ANS comprising at least one GP comprising one or more of: superior left GP (SLGP), inferior left GP (ILGP), anterior right GP (ARGP), inferior right GP (IRGP), and Marshall GP; receiving anatomical imaging modality data from an anatomical imaging modality which images an intrabody volume of a patient containing the heart; and locating the at least one GP in the intrabody volume of the heart based on the functional imaging modality data and anatomical imaging modality data.

According to an aspect of some embodiments of the present invention there is provided a method of imaging nervous tissue, comprising: acquiring functional imaging modality data from a functional imaging modality which images an intrabody volume of a patient having a body part, the patient having been injected with an imaging agent having a nervous tissue uptake by an autonomic nervous system (ANS); and locating the nervous tissue in the intrabody volume based on the functional imaging modality data.

Optionally, the method further comprises generating an image of the ANS based on the located nervous tissue with activity levels.

Optionally, the image indicates activity levels of the located nerve tissue.

Optionally, the method further comprises setting up a system for treatment of the located nervous tissue to treat disease based on improper activity of the located nervous tissue.

Optionally, the method further comprises acquiring anatomical imaging modality data from an anatomical image modality which images an intrabody volume of the patient containing the body part, and wherein locating comprises locating the nervous tissue in the intrabody volume of the heart based on the functional imaging modality data and the anatomical imaging modality data.

Optionally, the method further comprises positioning the located nervous tissue on the anatomical imaging modality data.

Optionally, the anatomical imaging modality data is acquired in real time during a treatment procedure, the locating is performed before and/or in real time during the treatment procedure, and the location of the nervous tissue is presented to an operator performing the treatment procedure.

Optionally, locating comprises locating at least one ganglionic plexus (GP) of the ANS, with a size of between 1 and 20 mm in maximal diameter.

Optionally, locating comprises locating at least two ganglionic plexus (GP) of the ANS, with a size of between 1 and 20 mm in maximal diameter.

Optionally, the method further comprises generating an ANS map comprising a distribution and/or activity of one or both of ANS synapses and GPs, and providing the ANS map for display.

Optionally, the method further comprises overlaying the ANS map with an image representation of an organ containing the nervous tissue.

Optionally, the method further comprises diagnosing the patient, the diagnosing comprising estimating an effect of the ANS on an organ based on one or both of activity and distribution of synapses and/or ganglions with respect to the organ.

Optionally, the method further comprises stimulating the ANS in conjunction with an imaging thereof and distinguishing between afferent and efferent activity based on the stimulation and the imaging.

Optionally, the method further comprises estimating an effect or change in effect and/or response of an autonomous nervous system and/or an organ based on one or both of activity and distribution of synapses and/or ganglions with respect to the organ, before, during and/or after the treatment.

Optionally, the method further comprises assigning the functional imaging modality data to spatial locations according to a model of a structure of an organ identifying the nervous tissue synapses and/or innervations based on data associated with the organ.

Optionally, the method further comprises providing a mapping function which maps for at least one region in the intrabody volume of a reference kinetic behavior, and applying the mapping function on the functional data to locate the nervous tissue in the intrabody volume.

Optionally, the method further comprises stimulating a nervous tissue in an intrabody volume of a patient to trigger a nervous response associated with a reference uptake value, acquiring, during the nervous response, functional data from the functional modality which images the intrabody volume, and localizing the nervous tissue in the intrabody volume according to the reference uptake value.

Optionally, the method further comprises acquiring anatomical data from an anatomical imaging modality which images the intrabody volume of the patient and localizing the target nervous tissue in the intrabody volume based on both the functional data and the anatomical data.

Optionally, the method further comprises identifying at least one region of interest (ROI) in an intrabody area according to a match with a reference value representing a reference uptake rate of an organ.

Optionally, localizing comprises filtering at least part of a representation of the intrabody volume in the functional data based on a match with a reference value.

Optionally, localizing comprises analyzing data from the functional data to identify at least one region of interest (ROI) in the intrabody volume, the analysis is based on a three dimensional (3D) model of the anatomy of the intrabody volume.

Optionally, localizing comprises identifying at least one anatomic landmark based on an analysis of respective portions of the functional data to register with an anatomic image.

Optionally, localizing comprises identifying a predefined pattern of a dynamic behavior of the imaging agent in at least a region of the intrabody area.

Optionally, the method further comprises targeting a sub region in the intrabody area as a target for a medical treatment.

Optionally, the functional data is captured before, during, after, and/or after a treatment given to the patient.

Optionally, the method further comprises acquiring a location of an intra-body treatment probe in the intrabody volume, and presenting both the functional data and the probe location to an operator during medical procedure.

Optionally, the method further comprises guiding a catheterization procedure for ablation based on the functional data, wherein the guiding is performed according to a combination between the functional data and an anatomical data of the intrabody area.

Optionally, the method further comprises applying a force to position an ablation element on a catheter and/or selecting a level of ablation energy, based on the location of the nervous tissue in the intrabody volume.

Optionally, the nervous tissue is selected from a group consisting of a carotid body nervous tissue, an aortic arch nervous tissue, a pulmonary nervous tissue, a renal nervous tissue, a splenic nervous tissue, a hepatic nervous tissue, an inferior mesenteric nervous tissue, a superior mesenteric nervous tissue, a muscular nervous tissue, a stomach, and a penile nervous tissue.

Optionally, the anatomical imaging modality data is received before and/or during a treatment procedure.

According to an aspect of some embodiments of the present invention there is provided a system for identifying ANS components within an image of an intrabody volume of a patient, the system comprising: a module for receiving functional imaging modality data from a functional imaging modality which images an intrabody volume of a patient having a body part containing nervous tissue, the patient having been injected with an imaging agent having nervous tissue uptake by an autonomic nervous system (ANS); a module for acquiring anatomical imaging modality data from an anatomical image modality which images an intra-body volume of the patient containing the body part; and a module for locating the nervous tissue in the intrabody volume based on the functional imaging modality data.

Optionally, the system further comprises a module for positioning the located nervous tissue on the anatomical imaging modality data.

Optionally, the functional imaging modality is selected from a group consisting of an electrocardiogram-gated SPECT (GSPECT) modality, a SPECT-CT modality and D-SPECT modality, and/or A-SPECT.

Optionally, the system further comprises a module for receiving an anatomical image from an anatomical imaging modality which images an intrabody volume of the patient containing the nervous tissue, and a module for combining the anatomical image with the functional image.

Optionally, the anatomical imaging modality is selected from a group consisting of a positron emission tomography (PET) modality, a computerized tomography (CT) modality, a magnetic resonance imaging (MRI) modality, and an Ultrasound modality.

Optionally, the system further comprises a module for generating an ANS map comprising a distribution and/or activity of one or both of ANS synapses and GPs.

Optionally, the imaging agent is metaiodobenzylguanidine (mIBG).

Optionally, the nervous tissue is a neural fiber.

Optionally, the nervous tissue is composed of synapses.

Optionally, the nervous tissue is a part of a peripheral nervous tissue.

Optionally, the nervous tissue is part of at least one of parasympathetic nervous tissue and sympathetic nervous tissue.

Optionally, the nervous tissue includes at least one ganglionic plexus (GP).

Optionally, the nervous tissue is selected from a group consisting of a carotid body nervous tissue, an aortic arch nervous tissue, a pulmonary nervous tissue, a renal nervous tissue, a splenic nervous tissue, a hepatic nervous tissue, an inferior mesenteric nervous tissue, a superior mesenteric nervous tissue, a muscular nervous tissue, a stomach, and a penile nervous tissue.

Optionally, the system further comprises an intra-body treatment probe for intraoperative ablation of the nervous tissue.

Optionally, the system further comprises a navigation system for the intra-body treatment probe, the navigation system adapted for displaying the located nervous tissue.

Optionally, the system further comprises imaging apparatus programmed to control one or more of injection, acquisition and/or reconstruction so as to identify one or both of ganglia and synapse density in innervated tissue.

Optionally, the system further comprises an output element programmed to display a 2D or 3D or higher dimensional map of distribution of synapses and/or ganglia with respect to a tissue volume or an organ, based on the imaging data.

Optionally, the system further comprises a module to estimate an effect of an autonomous nervous system on an organ.

Optionally, the system further comprises imaging apparatus programmed to selectively identify and/or measure and/or display one or more of sympathetic nervous tissue, innervated tissue, afferent pathways, efferent pathways and parasympathetic tissue.

Optionally, 2-6 GPs are identified.

Optionally, the size of the identified GPs ranges from about 2×2×2 mm to about 4×4×4 mm.

Optionally, the system further comprises a storage unit for storing a reconstructed image of the identified nervous tissue.

Optionally, the system further comprises a module for displaying a personalized GP map on an anatomical image.

Optionally, activity levels are displayed on the anatomical image.

According to an aspect of some embodiments of the present invention there is provided a system for identifying ANS components within an image of an intrabody volume of a patient, the system comprising: at least one module for: receiving functional imaging modality data from a functional imaging modality which images an intrabody volume of a patient having a body part containing nervous tissue, the patient having been injected with an imaging agent having nervous tissue uptake by an autonomic nervous system (ANS); acquiring anatomical imaging modality data from an anatomical image modality which images an intrabody volume of the patient containing the body part; and locating the nervous tissue in the intrabody volume based on the functional imaging modality data and anatomical imaging modality data.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In some exemplary embodiments of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse or touch screen are optionally provided as well.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a schematic diagram of an autonomic nervous system, to help understand some embodiments of the present invention;

FIG. 2A is a flowchart of a method of localizing nervous tissue based on a combination of anatomical data and functional data of an intrabody volume, according to some embodiments of the present invention;

FIG. 2B is a flow chart of a computer-implemented method for combining the functional and anatomical images and/or locating the GPs, in accordance with some embodiments of the present invention;

FIG. 3 is a schematic block diagram of a system for localizing nervous tissue based on a combination of anatomical data and functional data of an intrabody volume, according to some embodiments of the present invention;

FIG. 4 is a flowchart of a clinical protocol wherein a patient is injected with radio labeled metaiodobenzylguanidine, according to some embodiments of the present invention;

FIG. 5 is a schematic illustration of a human heart and a set of four ganglionic plexi and their axons;

FIG. 6 is a flowchart of a method for performing an ablation treatment by mapping complex fractionated atrial electrograms, contractile force sites, and/or dominant frequency sites in the atria as target areas for an treatment, such as ablation, according to some embodiments of the present invention;

FIGS. 7A-7D, 8A-8D, 9A-9D, 10A-10D and 11A-11D are sets of figures that depicts activity sites in the heart which are set as areas for ablations, according to some embodiments of the present invention, where each set includes four views (clockwise): right anterior oblique (RAO). Posterior-anterior (PA) view, a right lateral view (left side) and a posterior view (right side);

FIG. 12 is a flowchart of a method of localizing a nervous tissue based on an association of different regions in a SPECT image to different organs and/or tissues based on a mapping function, according to some embodiments of the present invention;

FIG. 13 shows an image of the left atrium and left ventricle, in which the left atrium is colored in accordance with a radio labeled metaiodobenzylguanidine (mIBG) molecule activity according to exemplary embodiments of the invention, showing a maximal activity level in the left inferior pulmonary vein;

FIG. 14 shows an image of the right ventricle and left ventricle, in which the right ventricle is colored in accordance with mIBG activity according to exemplary embodiments of the invention, showing a maximal activity level in the intra ventricular septum;

Figure 15:
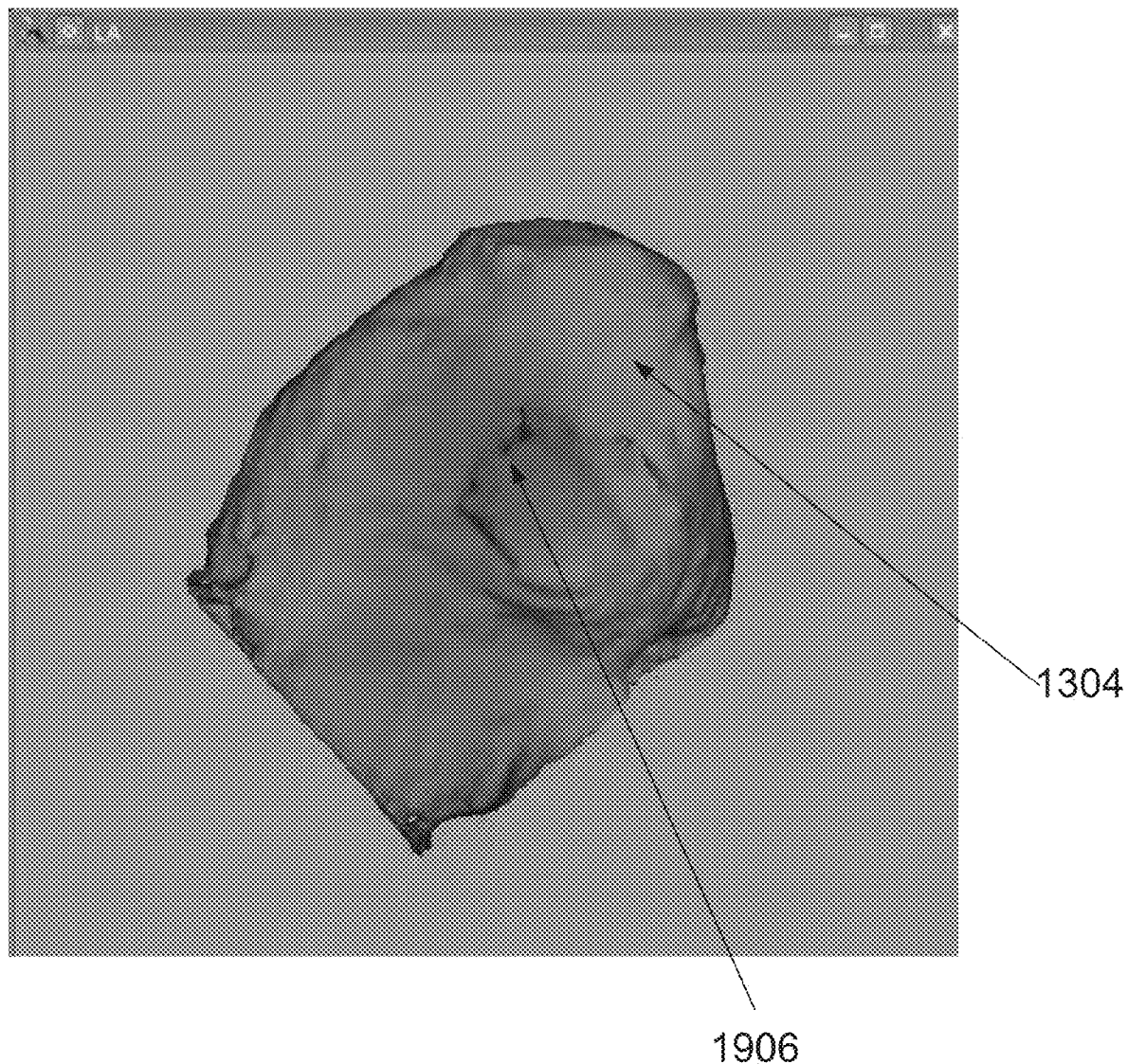
Figure 21A:
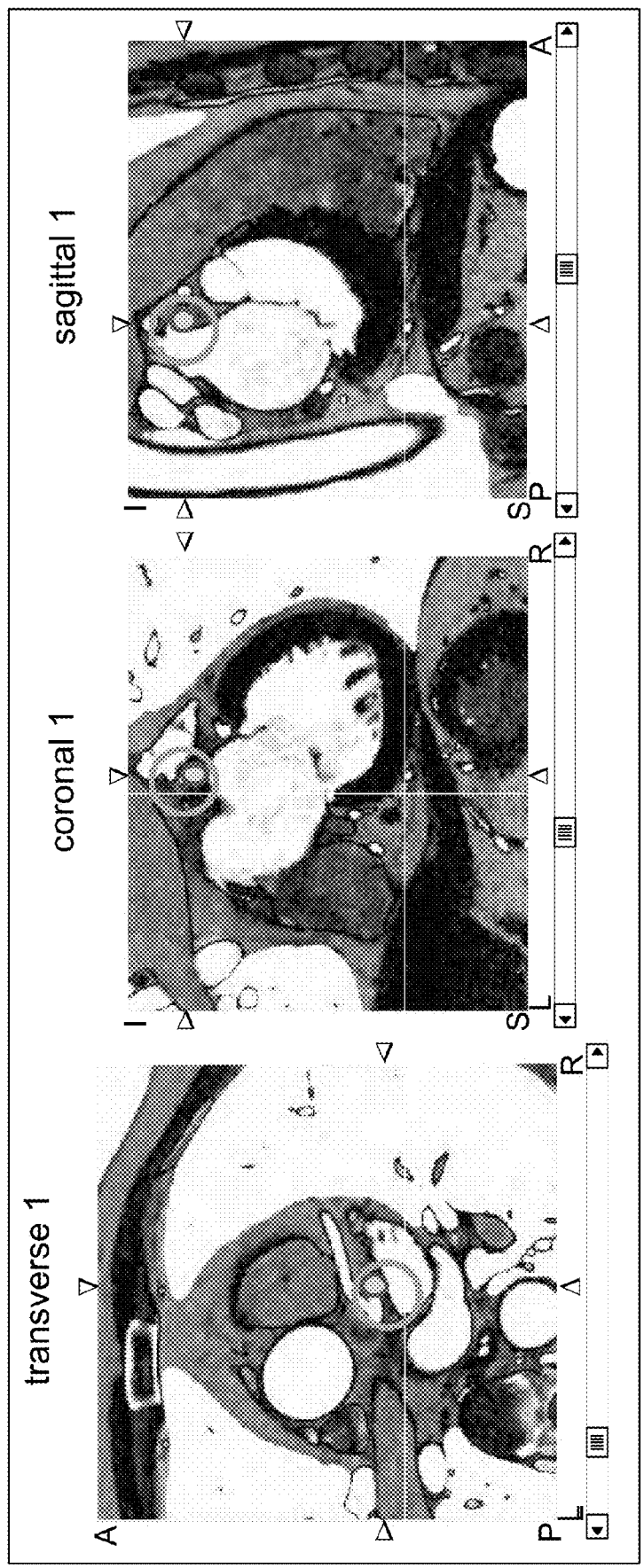
Figure 21B:
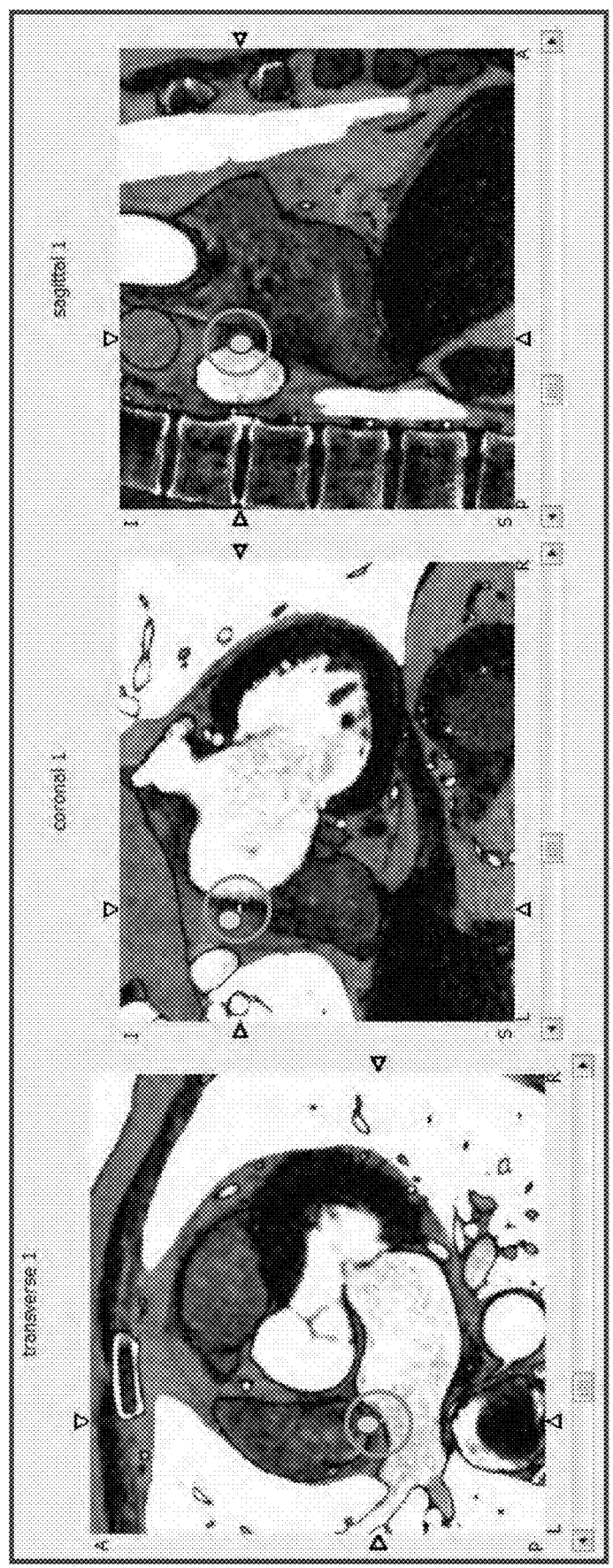
Figure 21C:
Figure 22C:
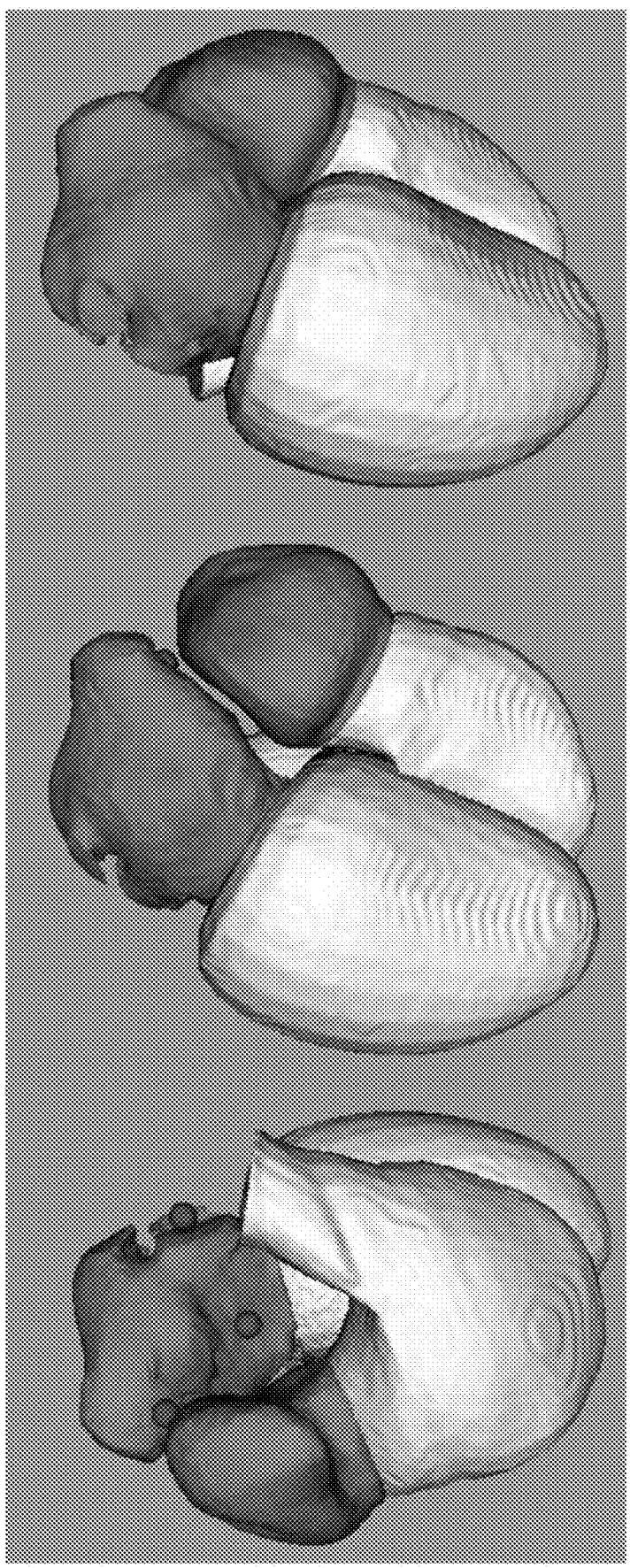
Figure 23A:
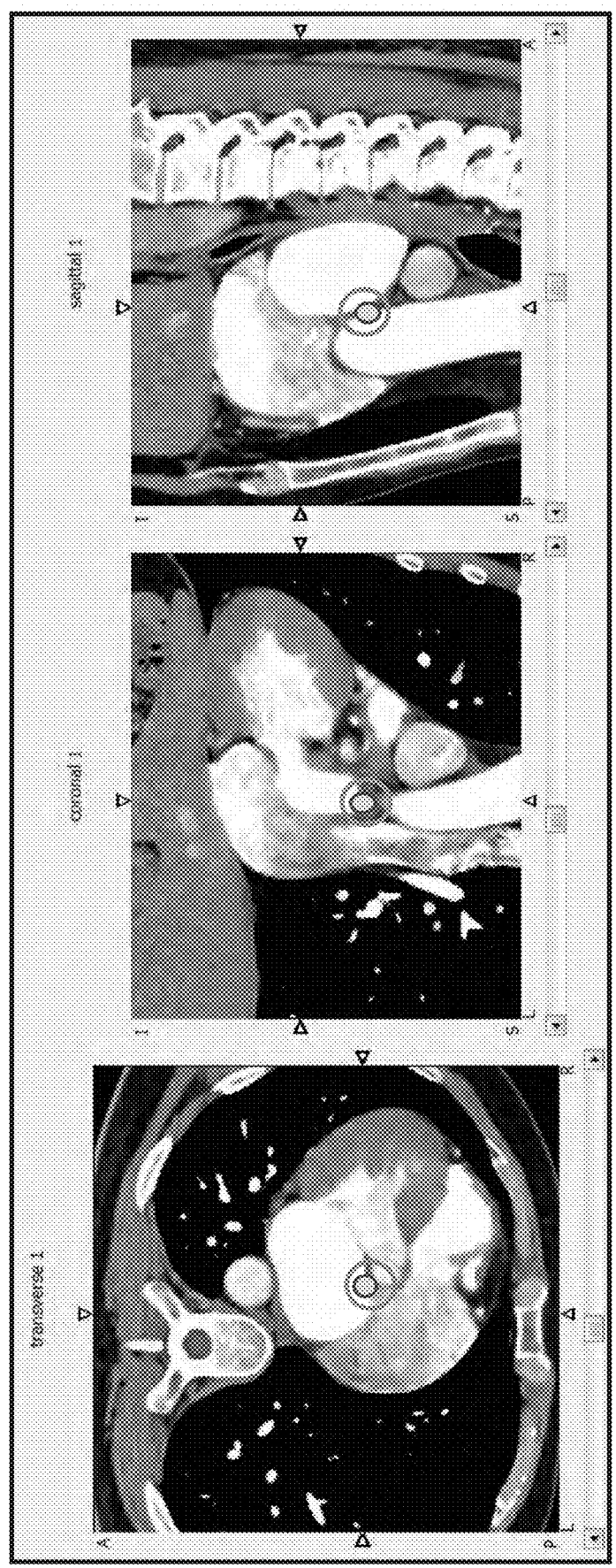
Figure 23B:
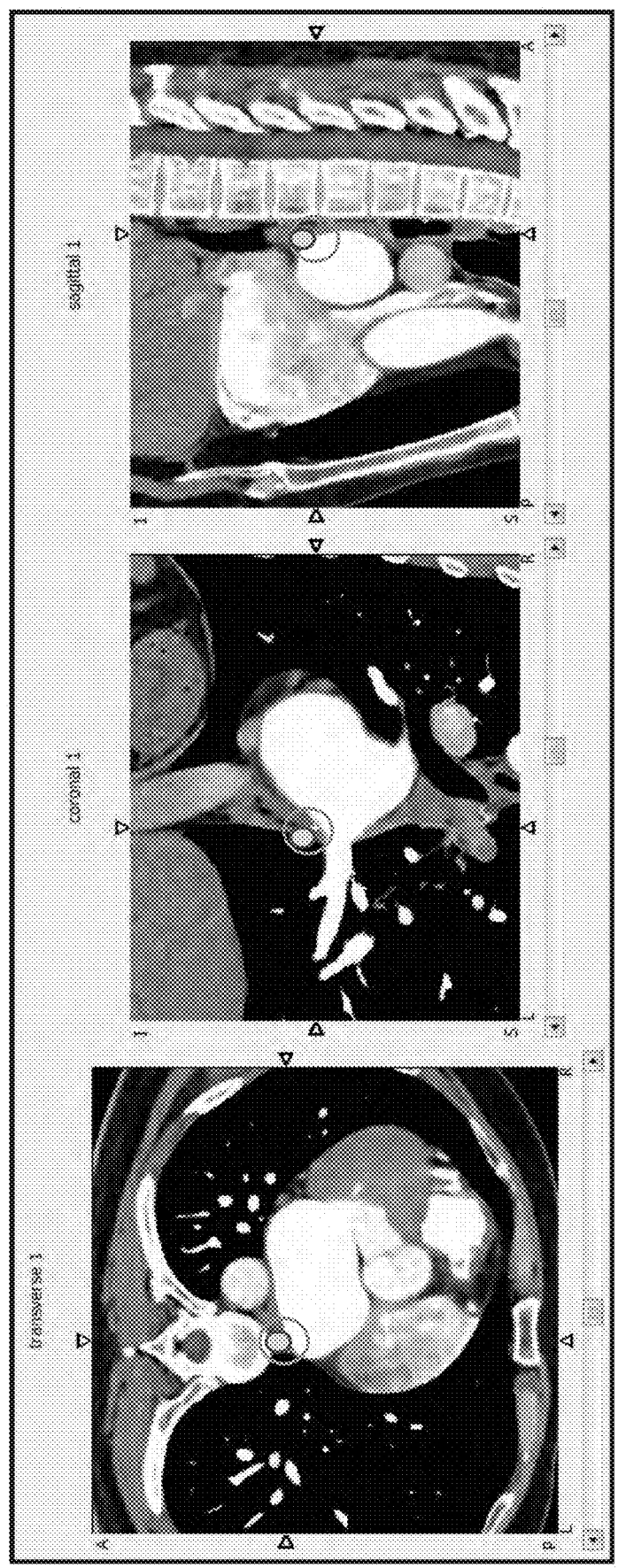
Figure 23C:
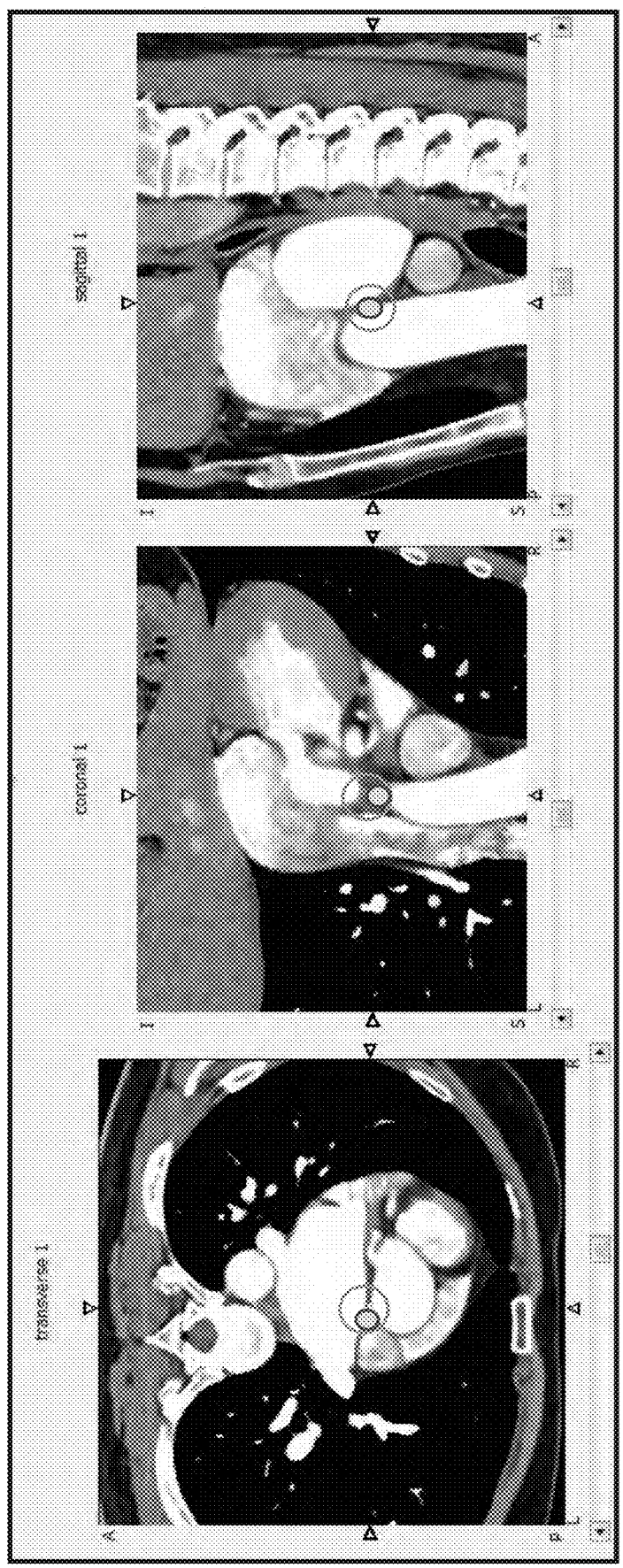
Figure 23D:
Figure 25:
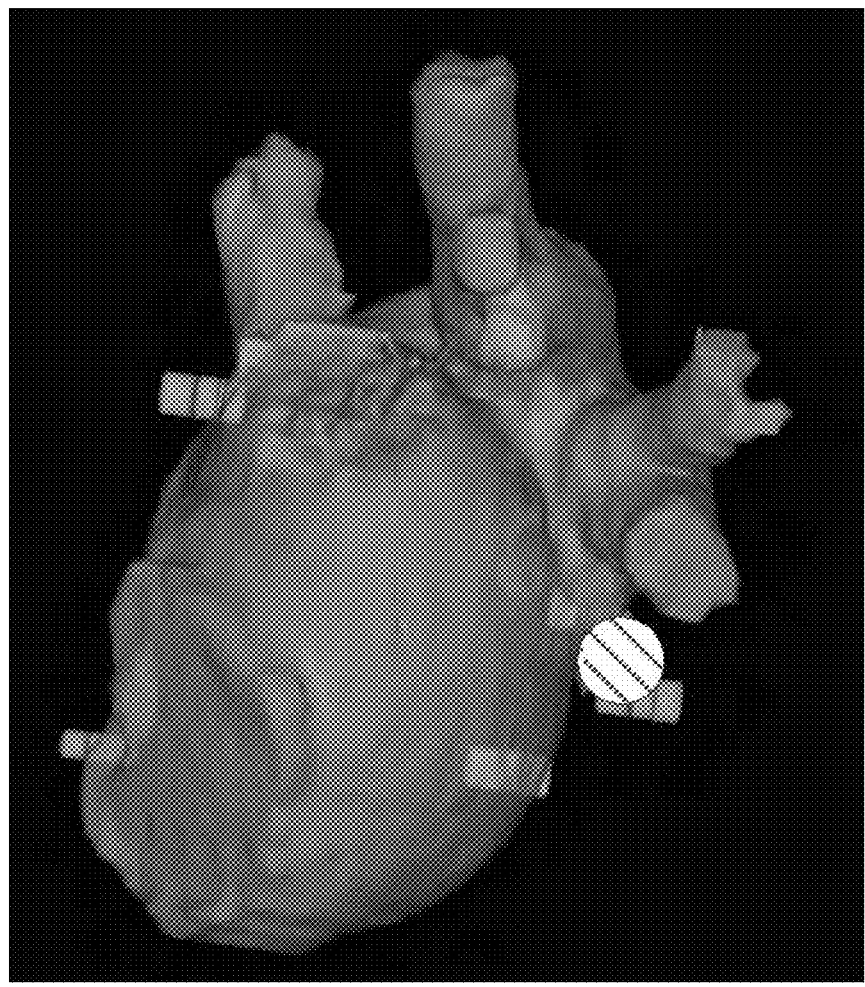
Figure 26:
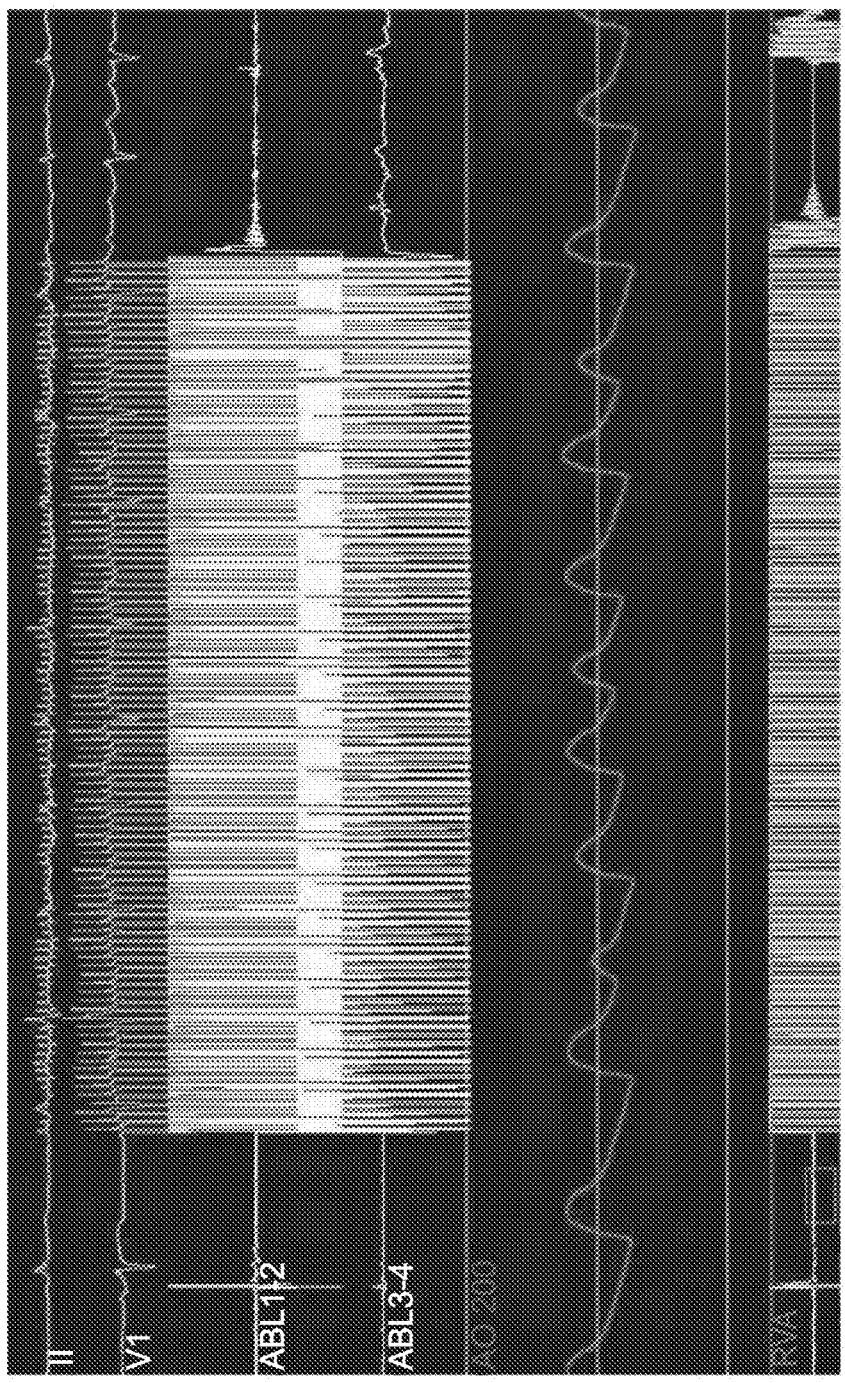
Figure 27A:
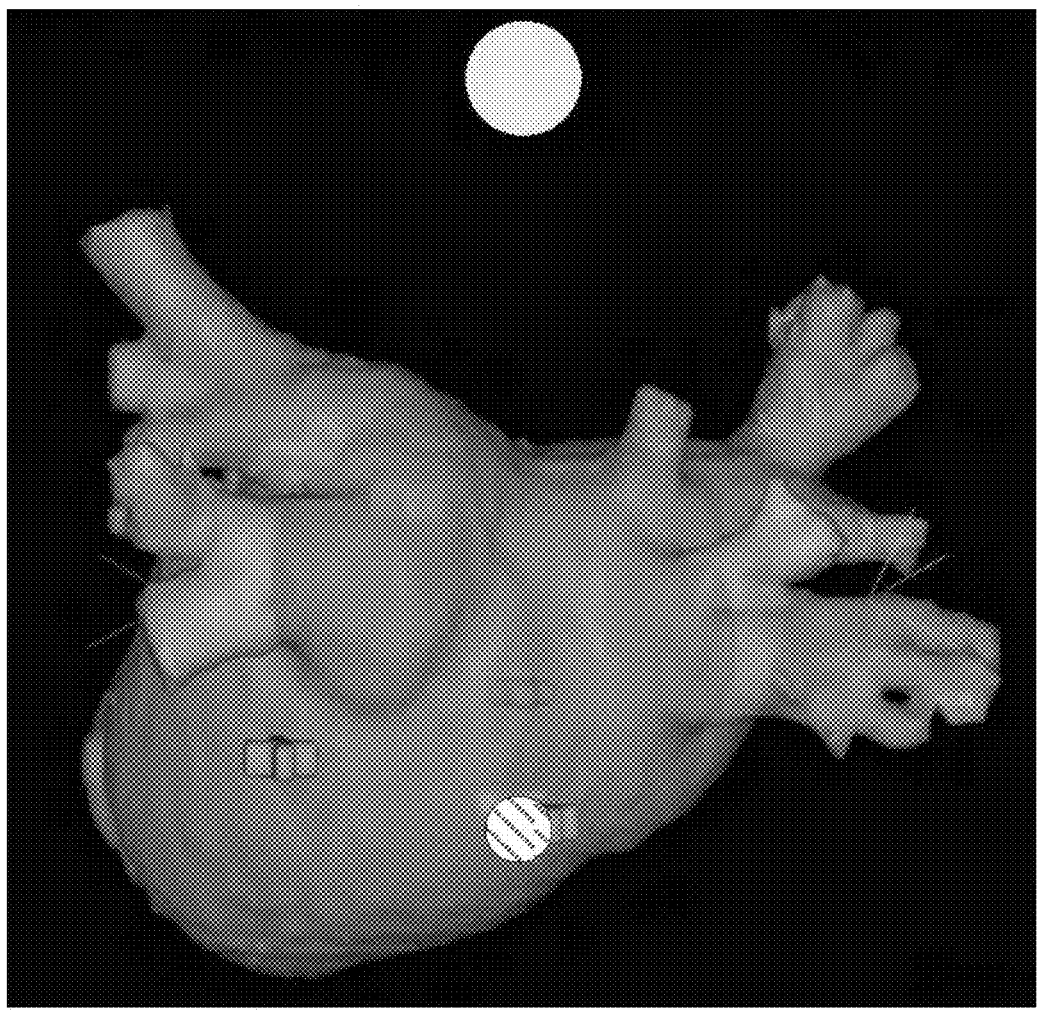
Figure 27B:
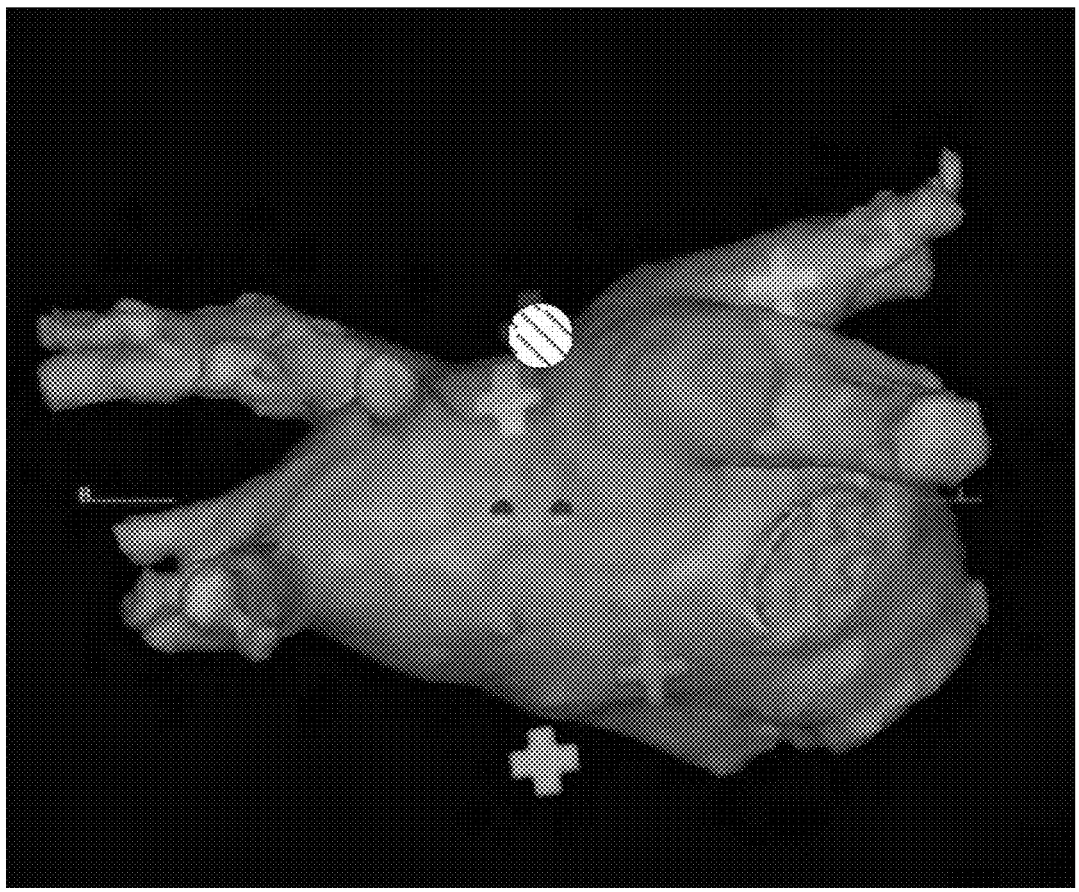
Figure 28:
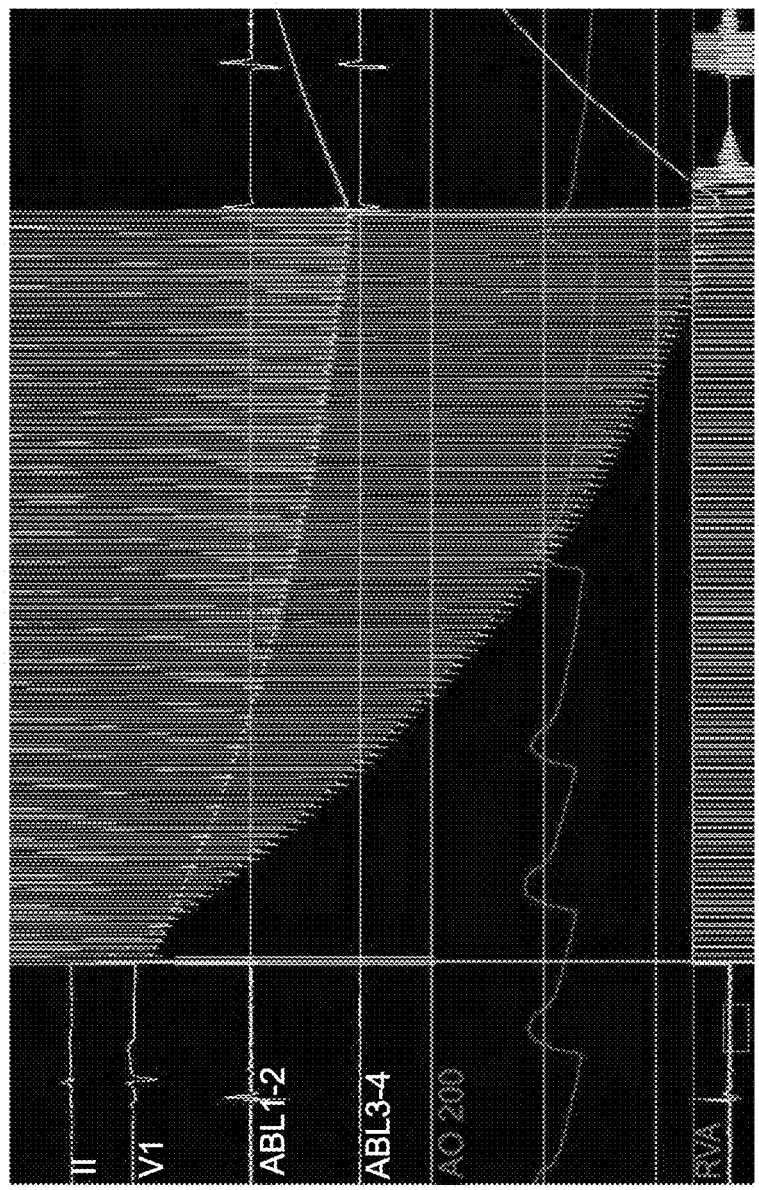
Figure 29:
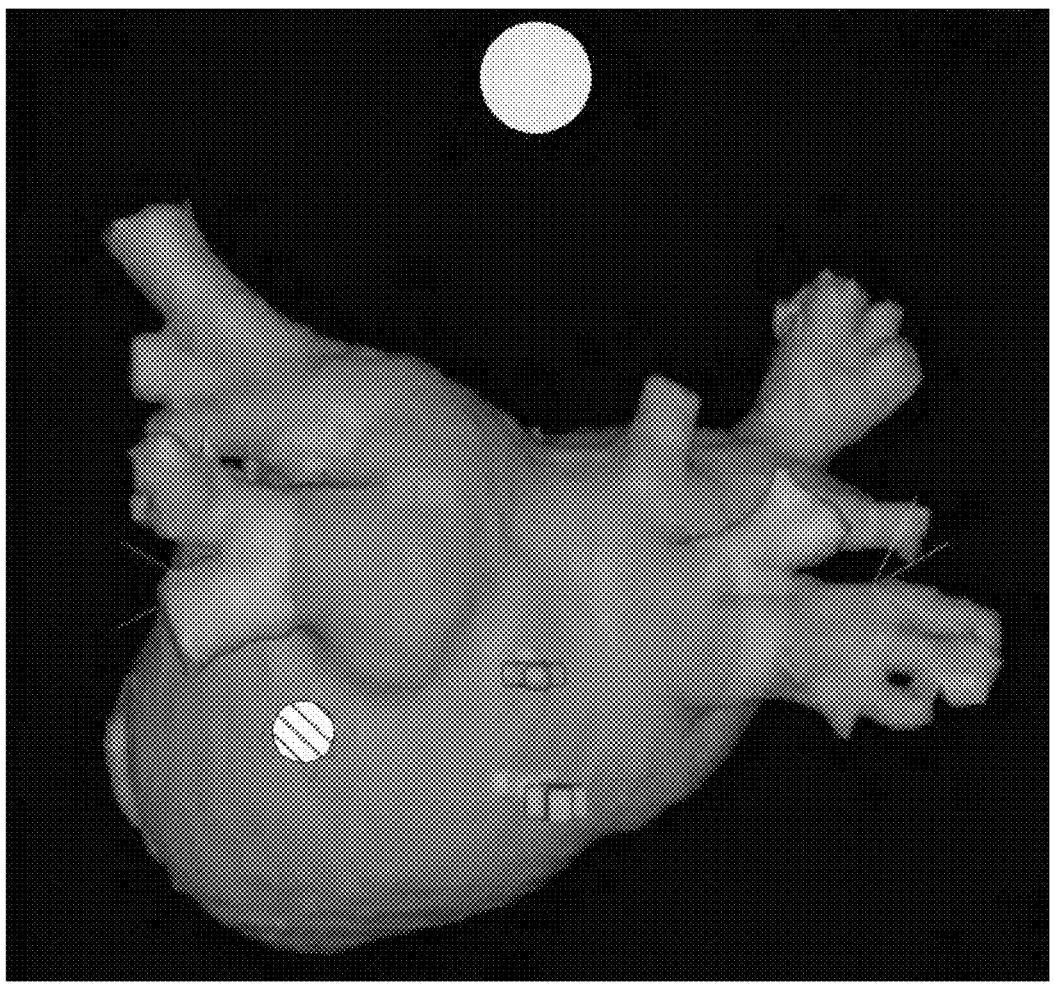
Figure 30:
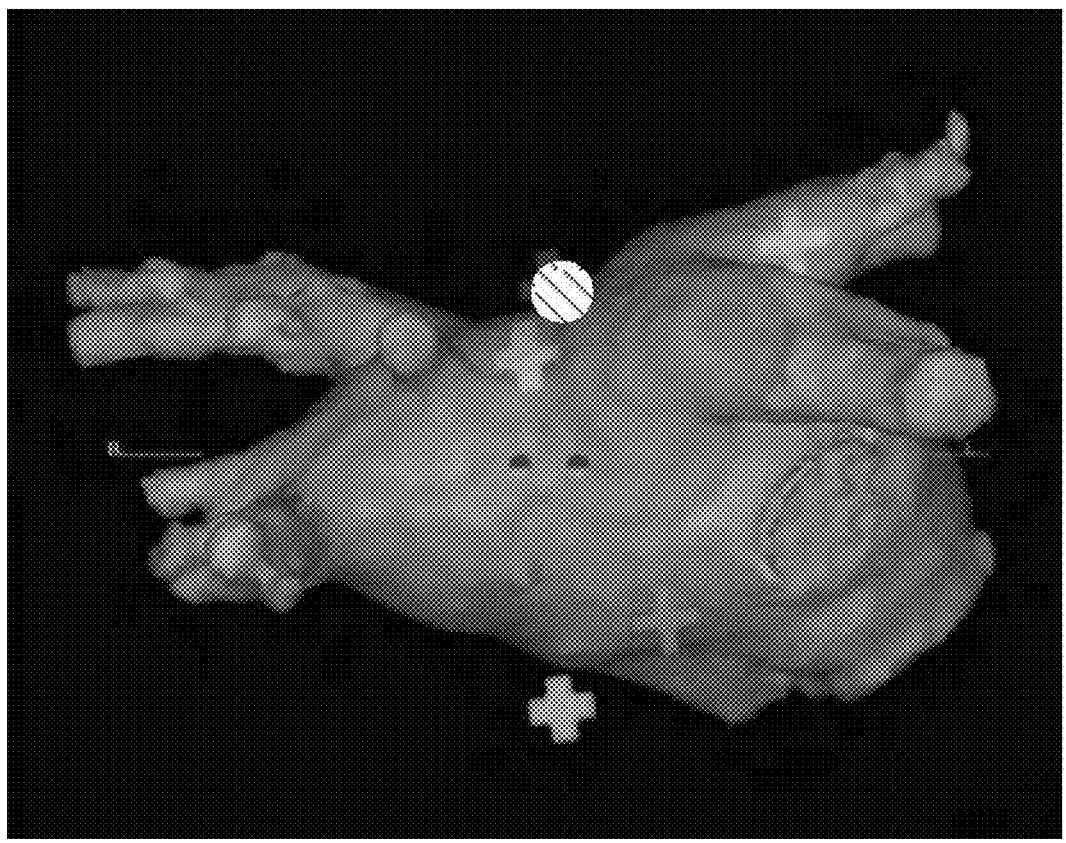
Figure 31:
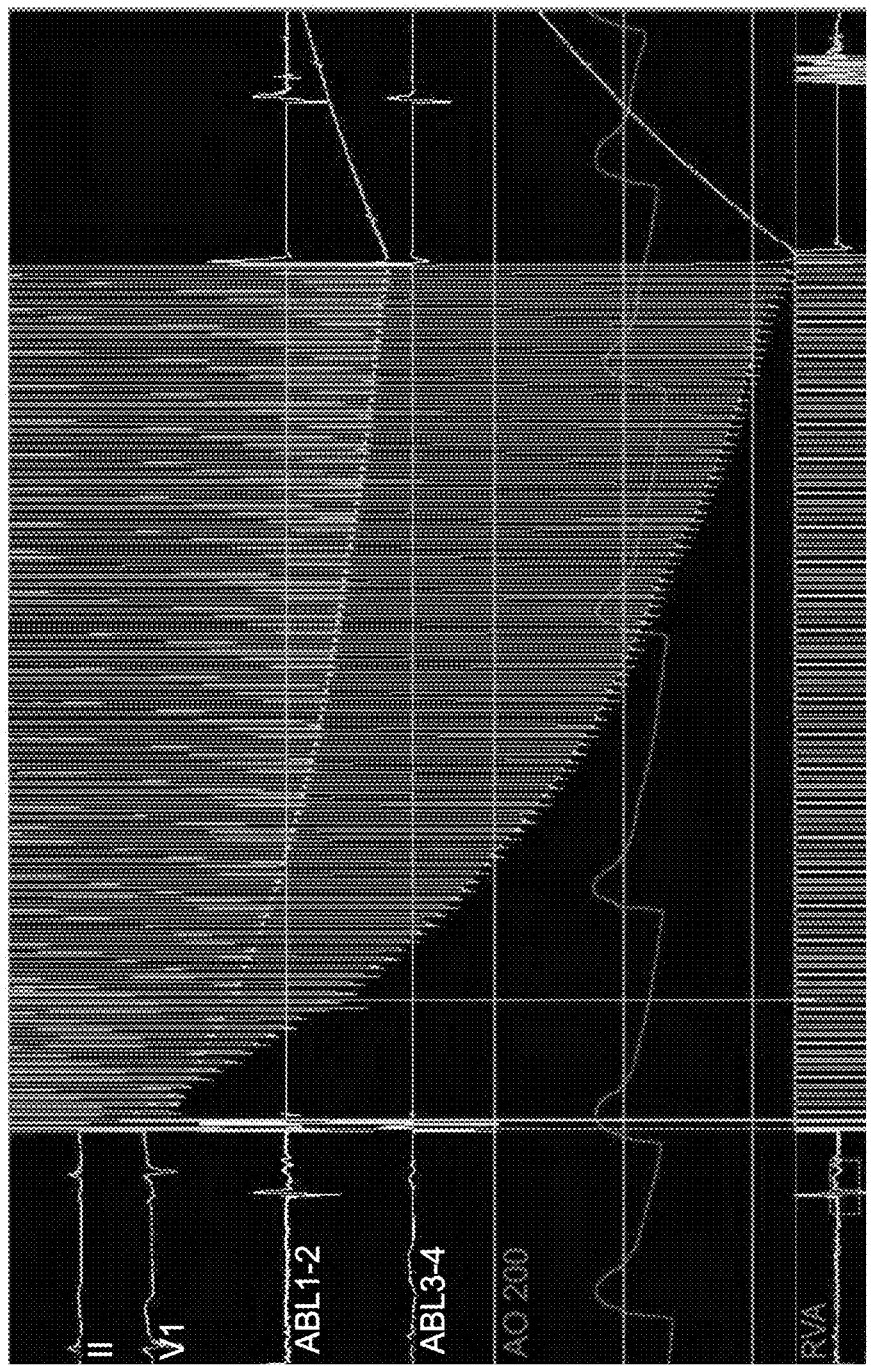
Figure 32:
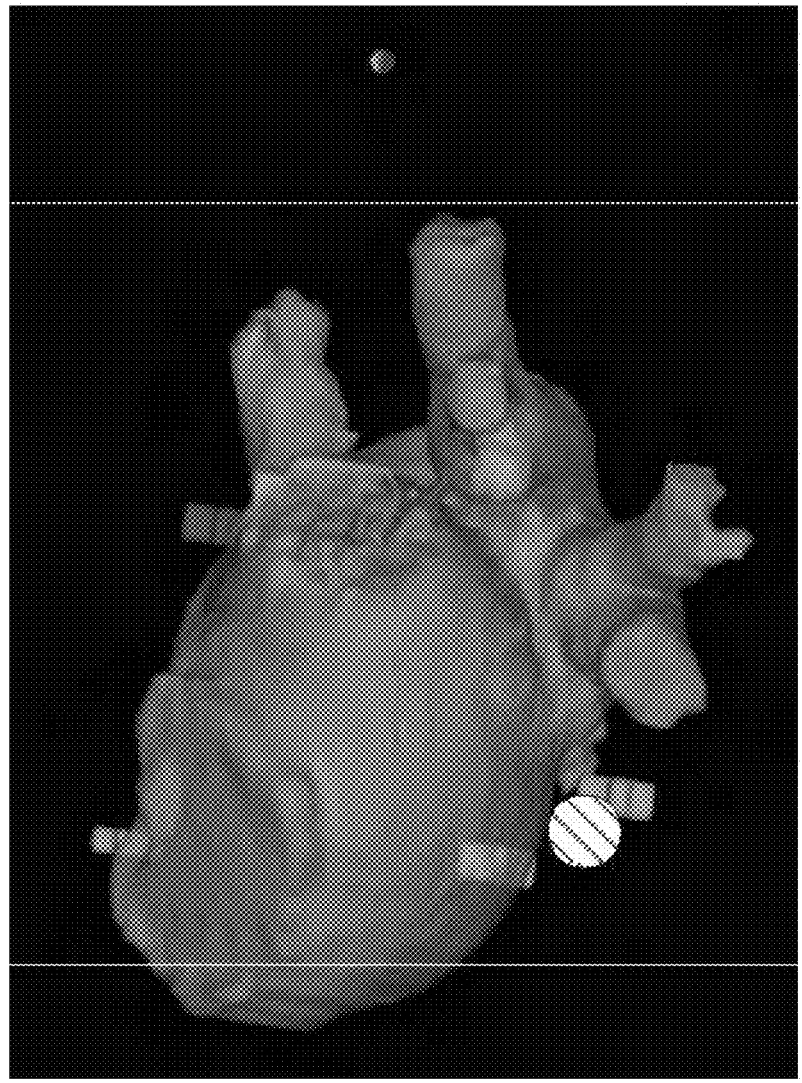
Figure 33:
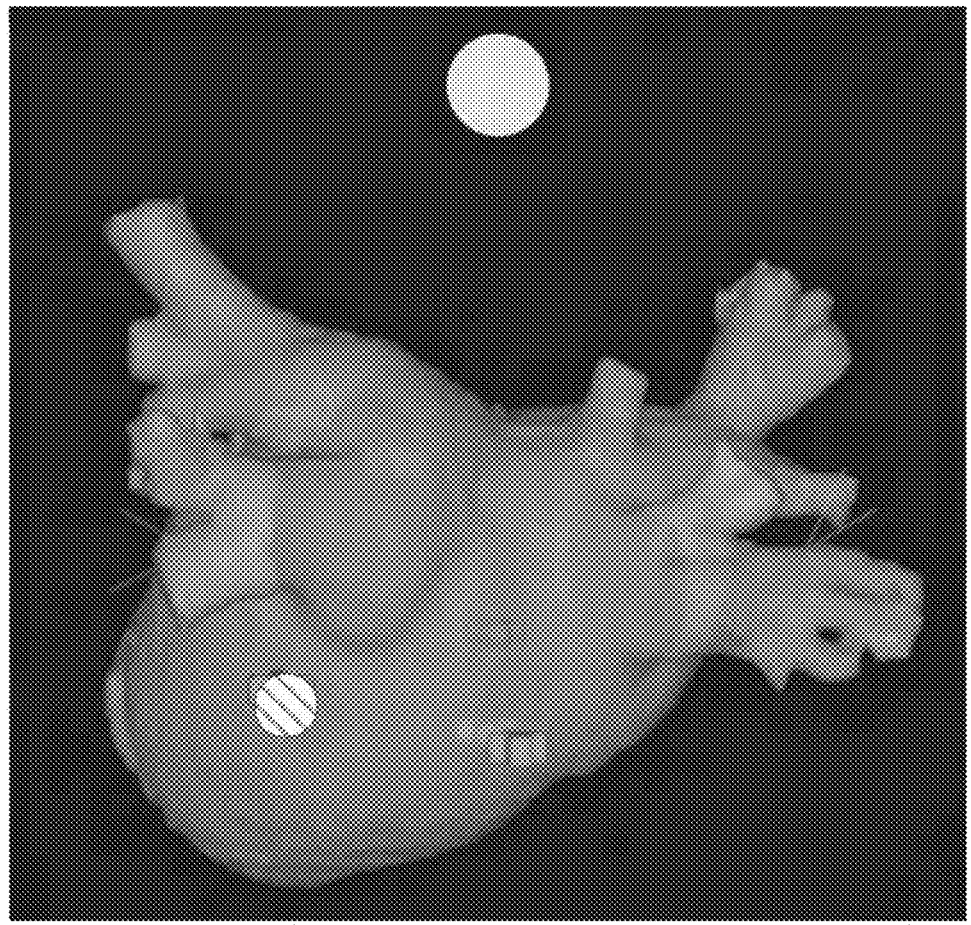
Figure 34:
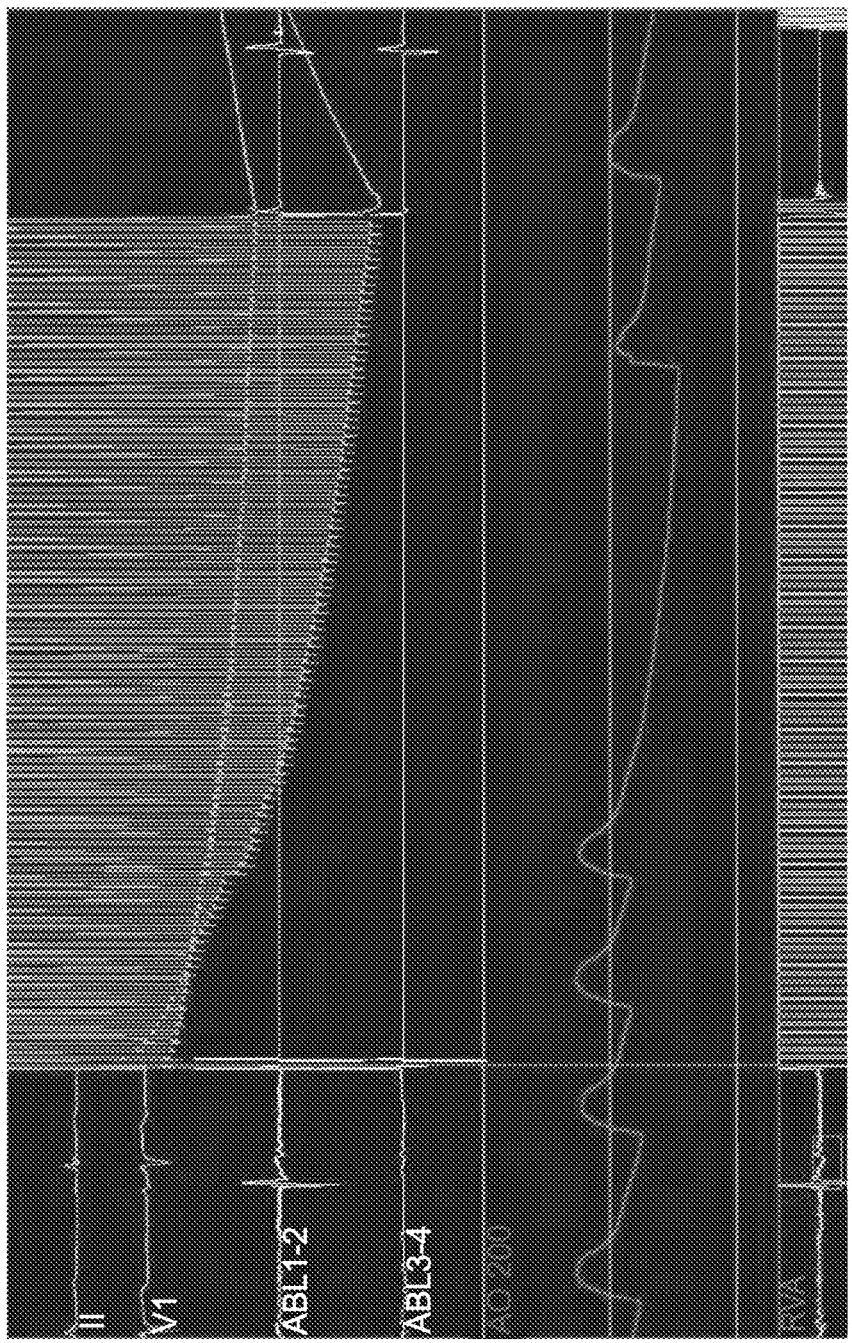
Figure 35:
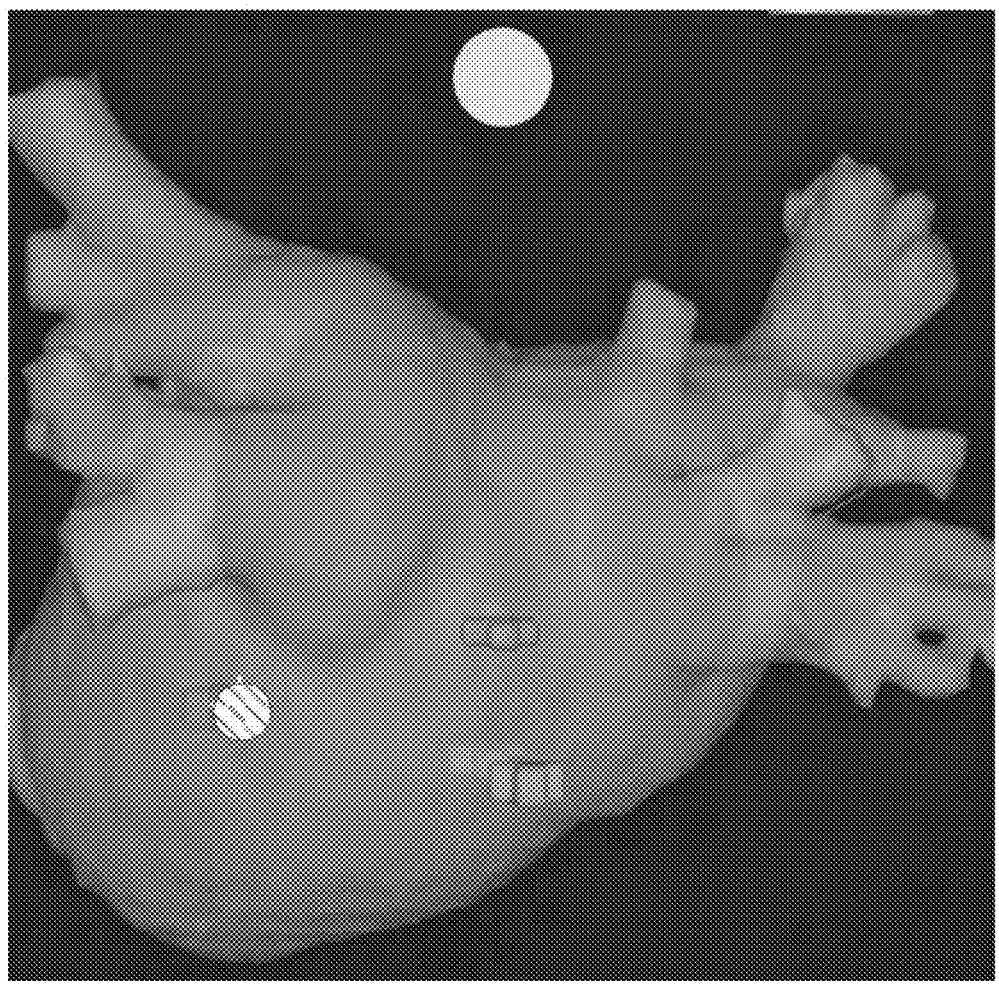
Figure 36:
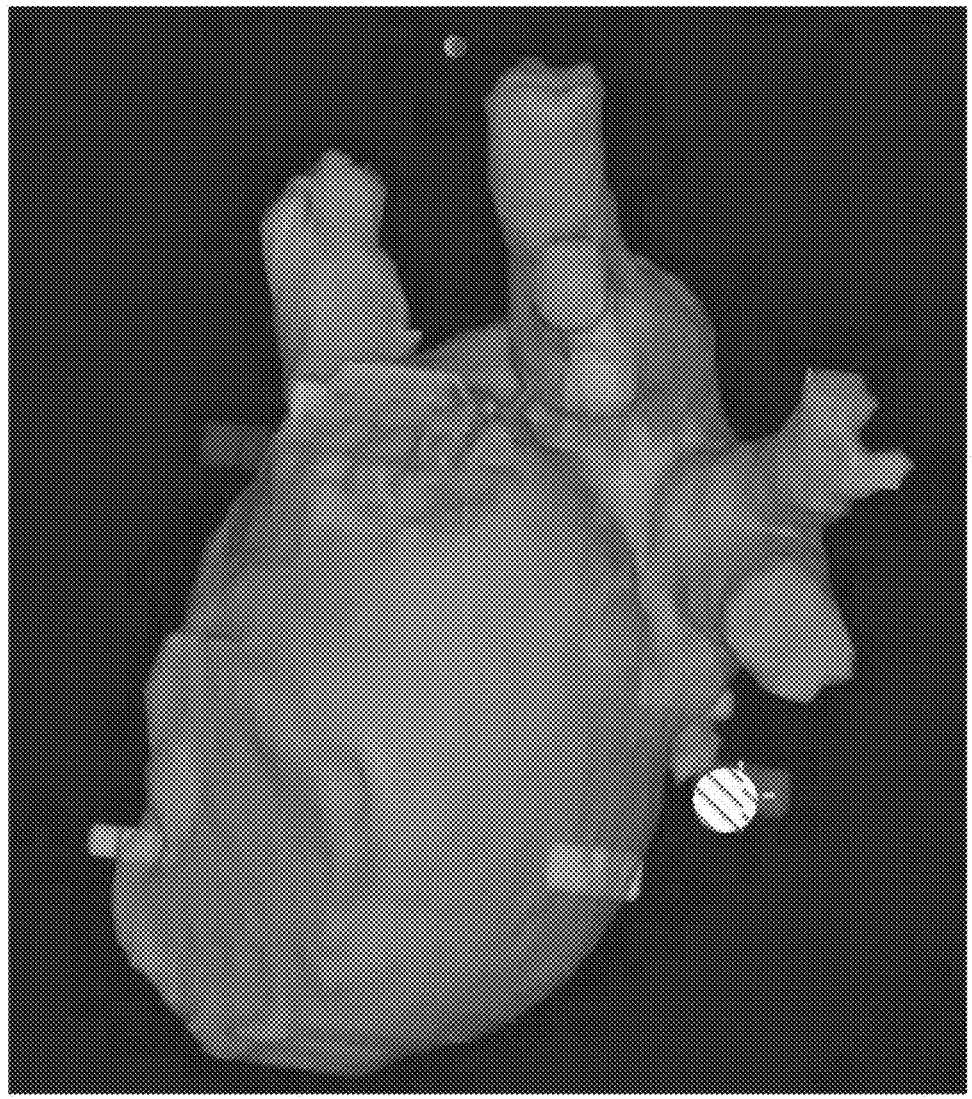
Figure 37:
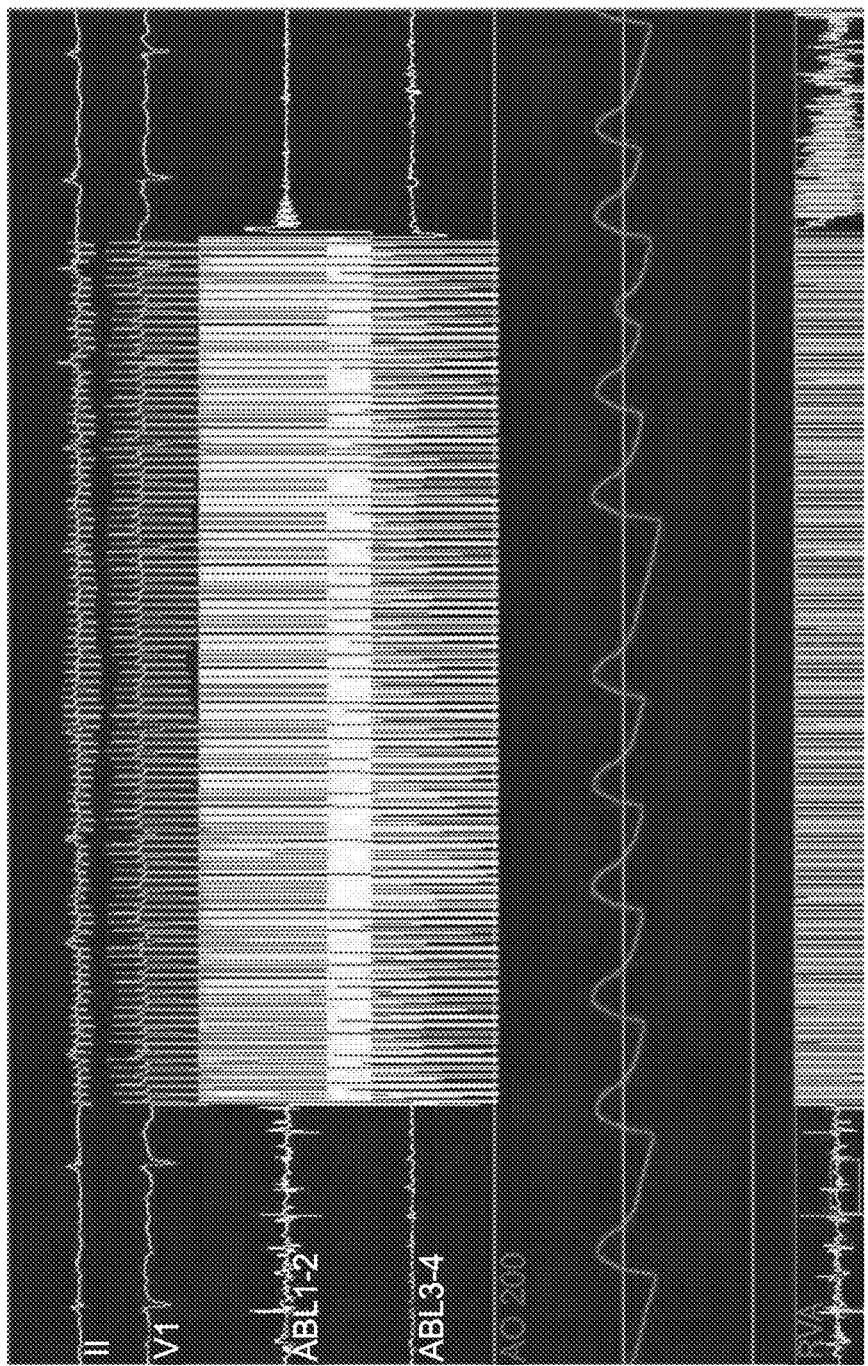
Figure 38:
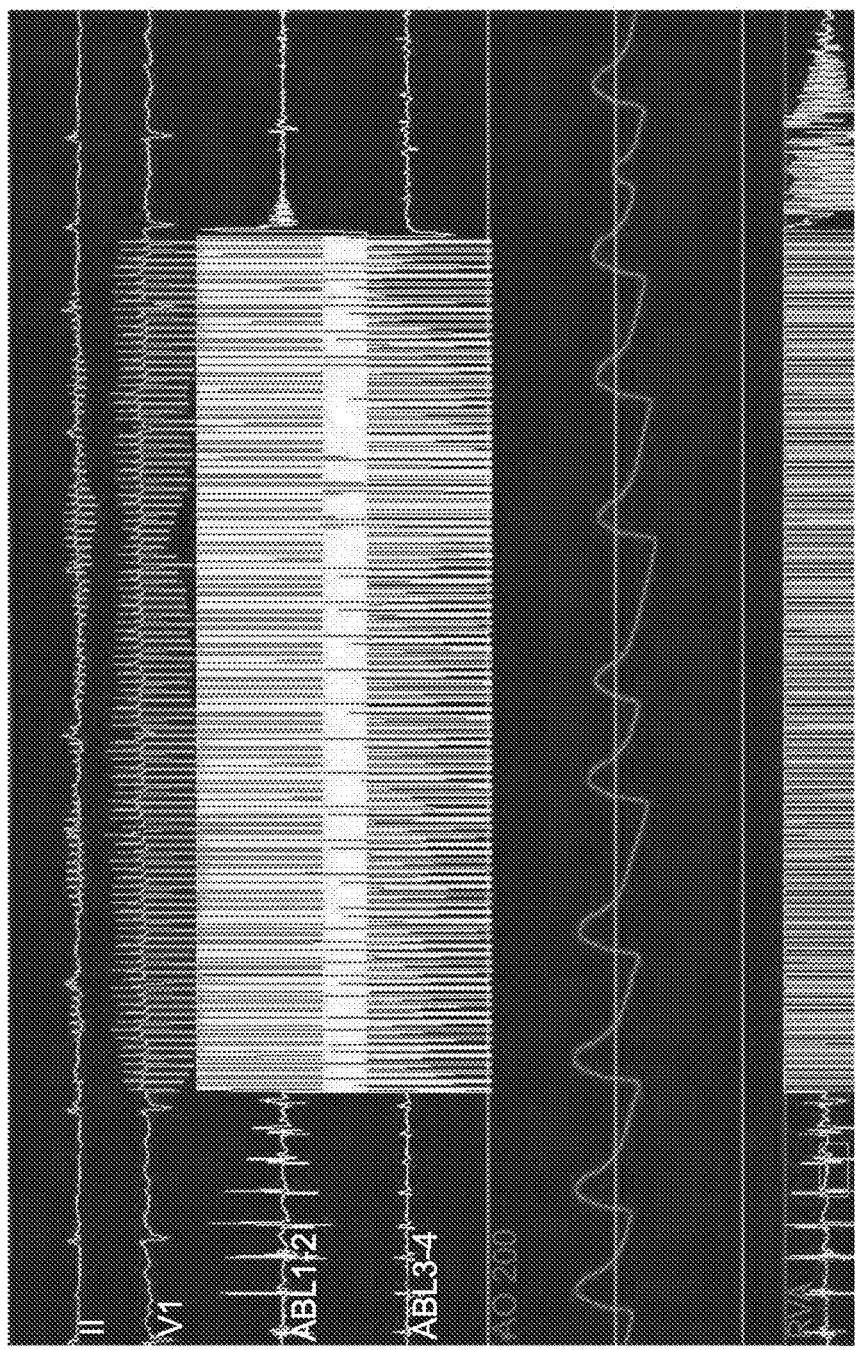
Figure 39:
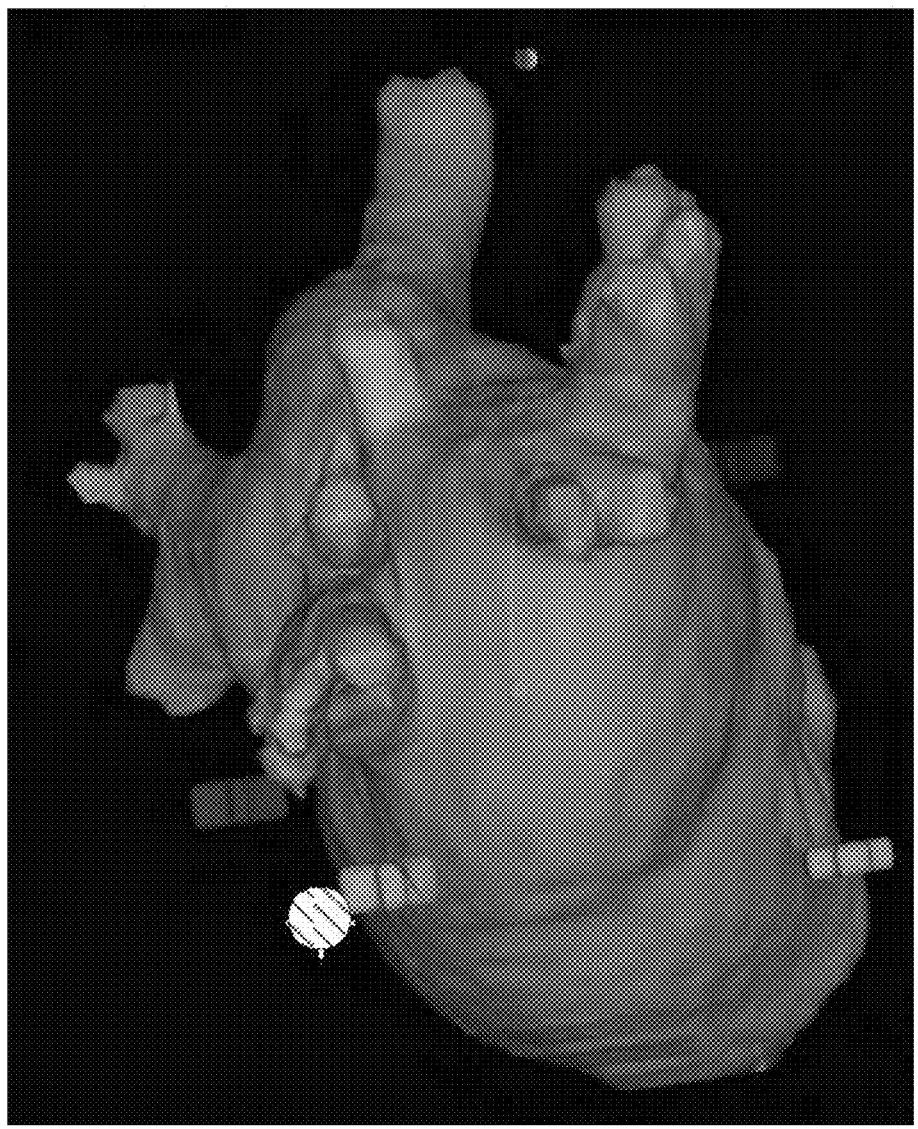
Figure 40:
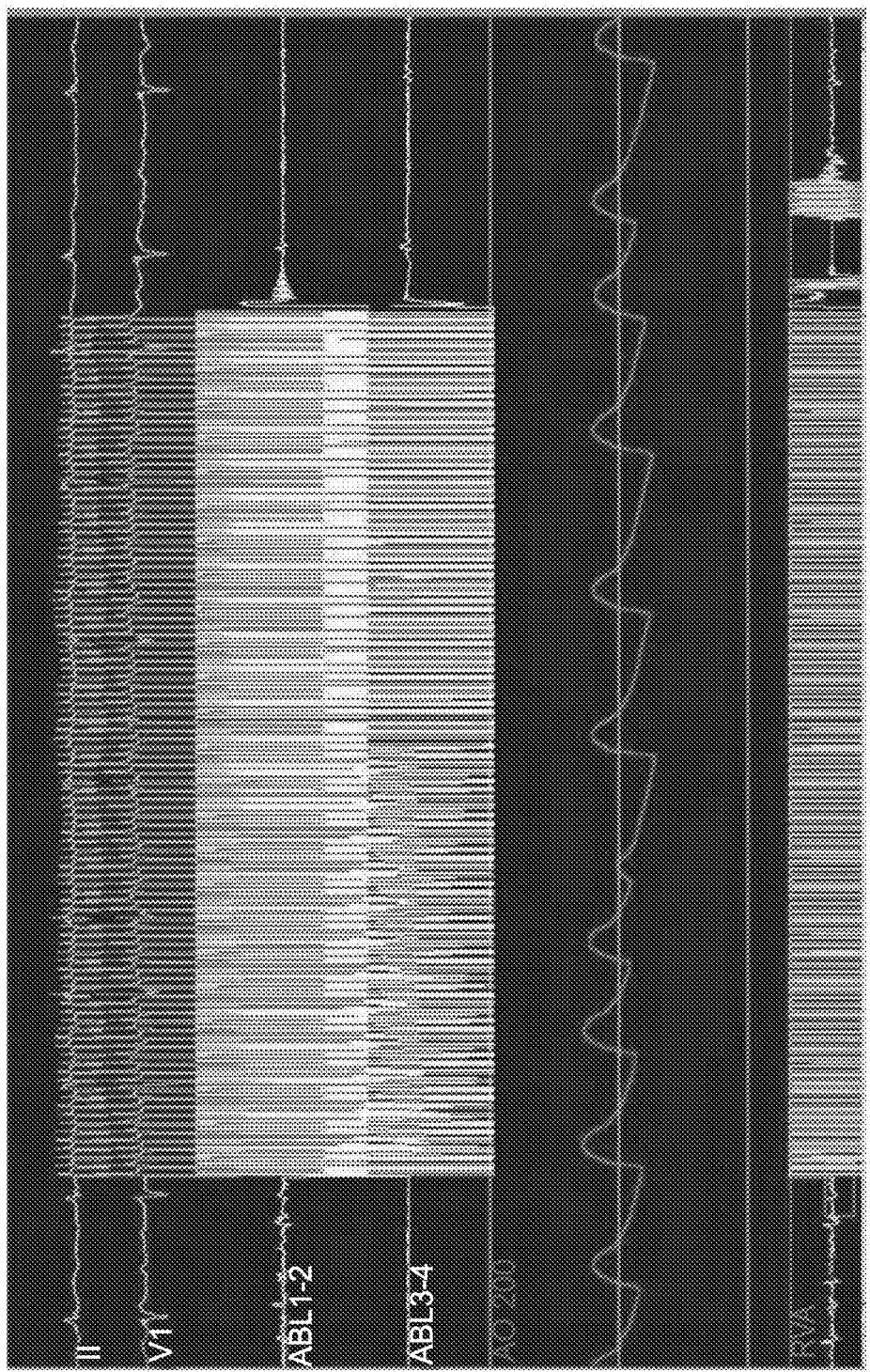
Figure 41:
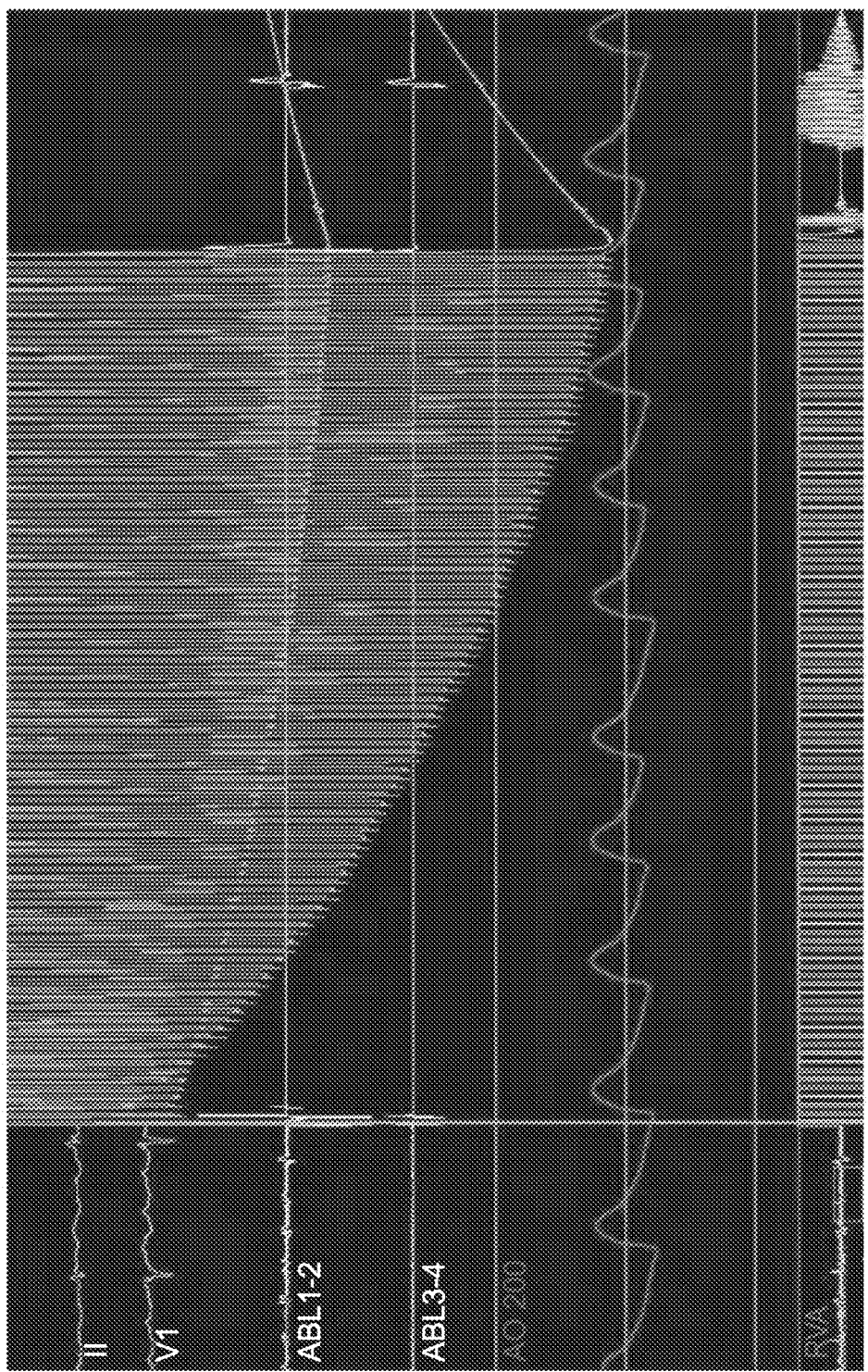
Figure 42:
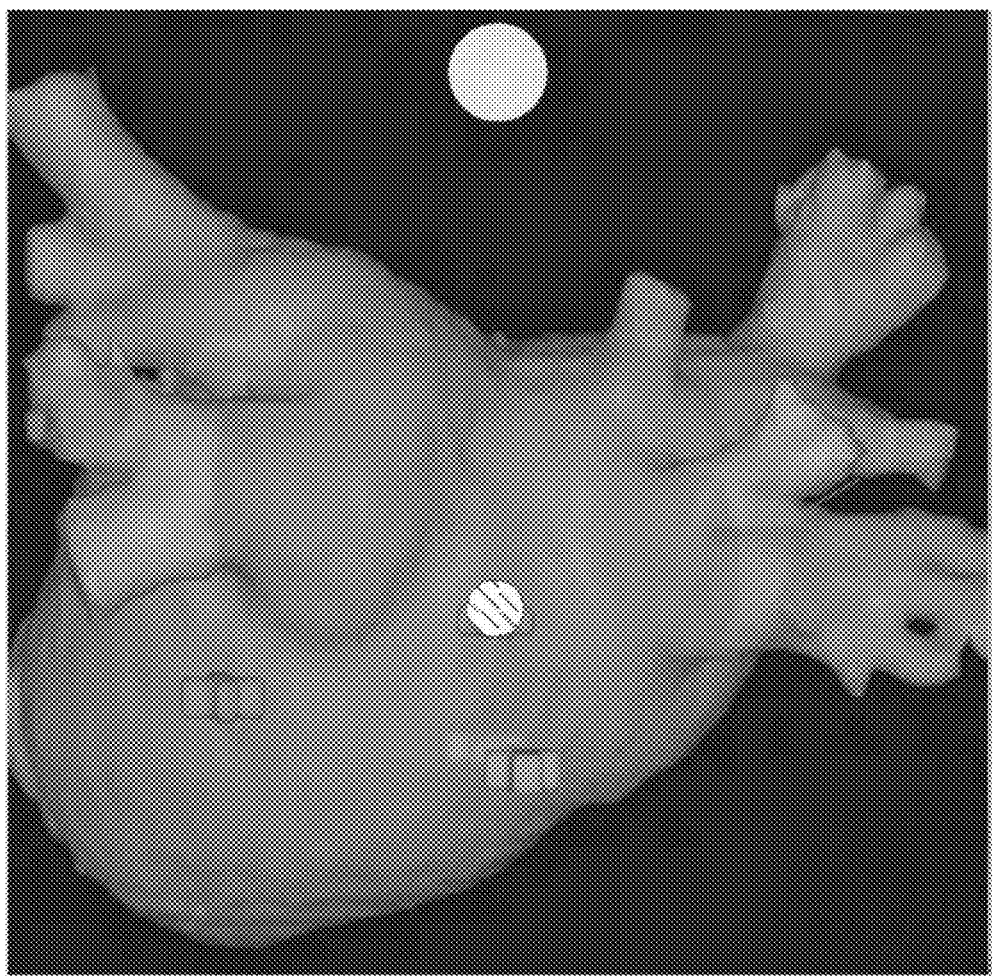
Figure 43:
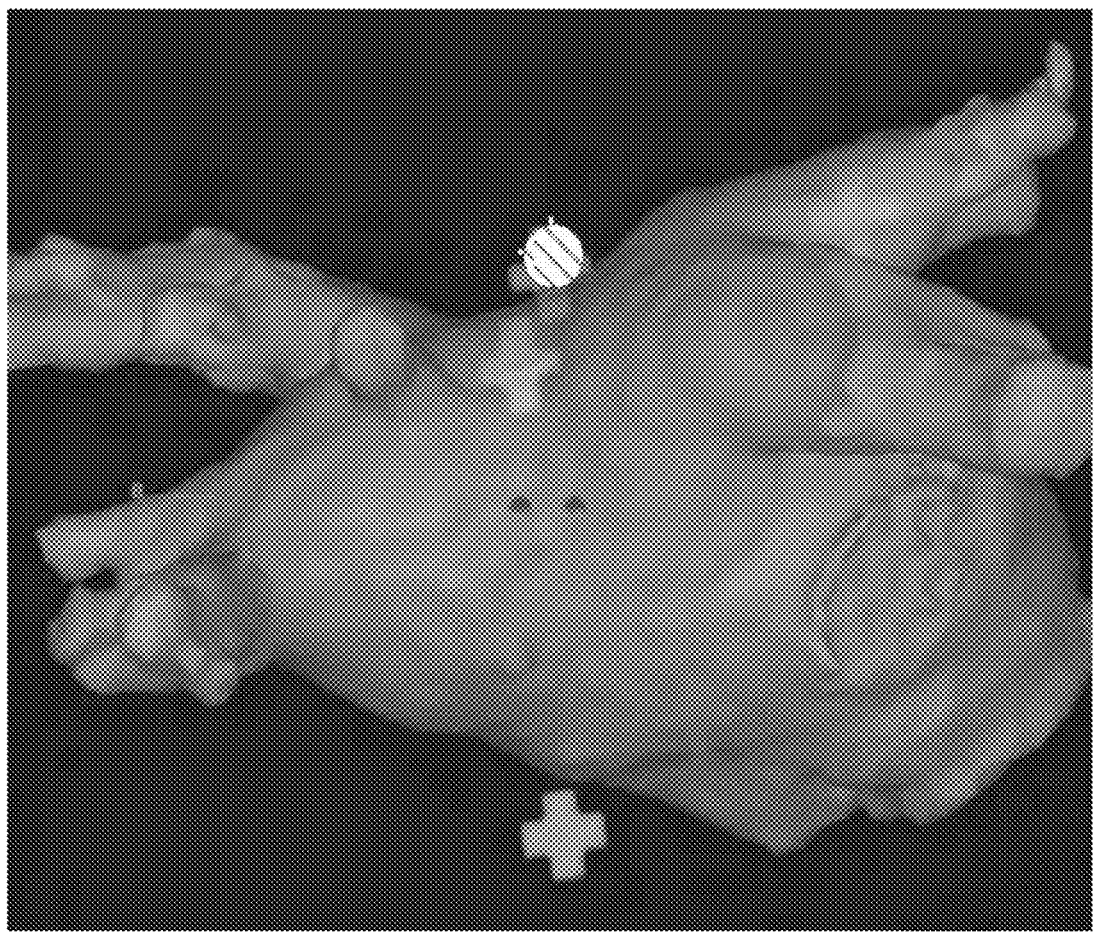
Figure 44A:
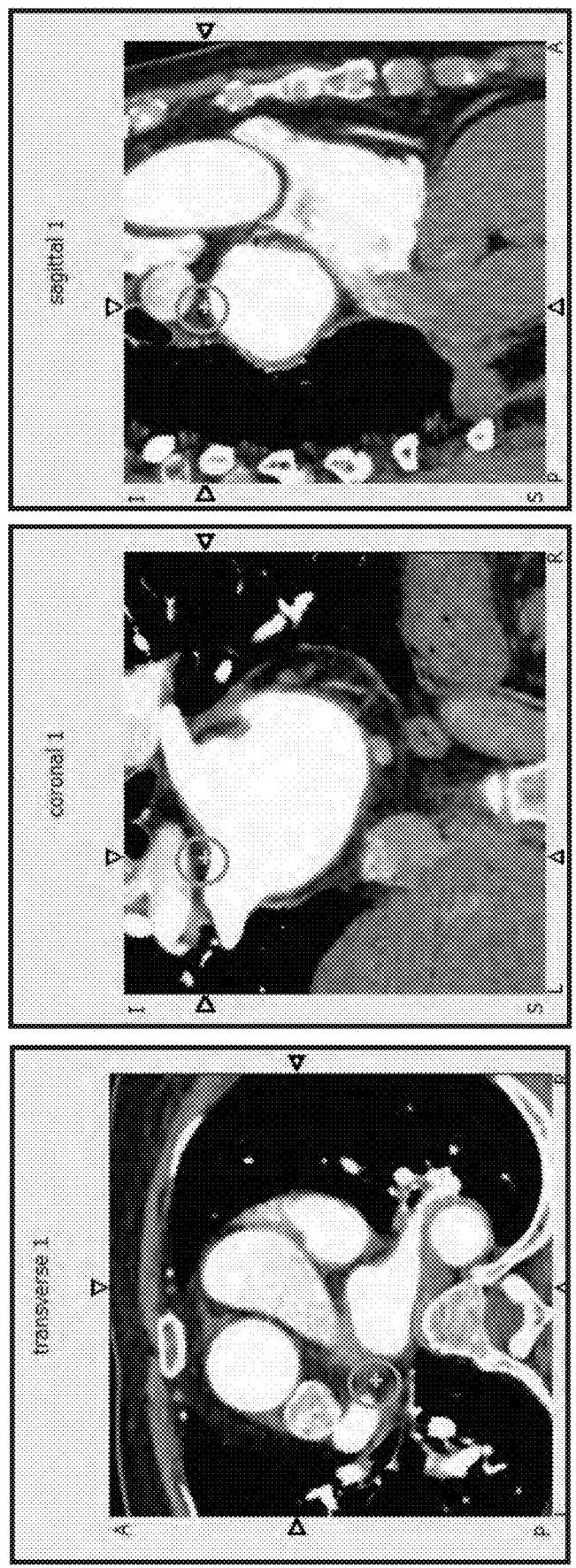
Figure 44B:
Figure 44C:
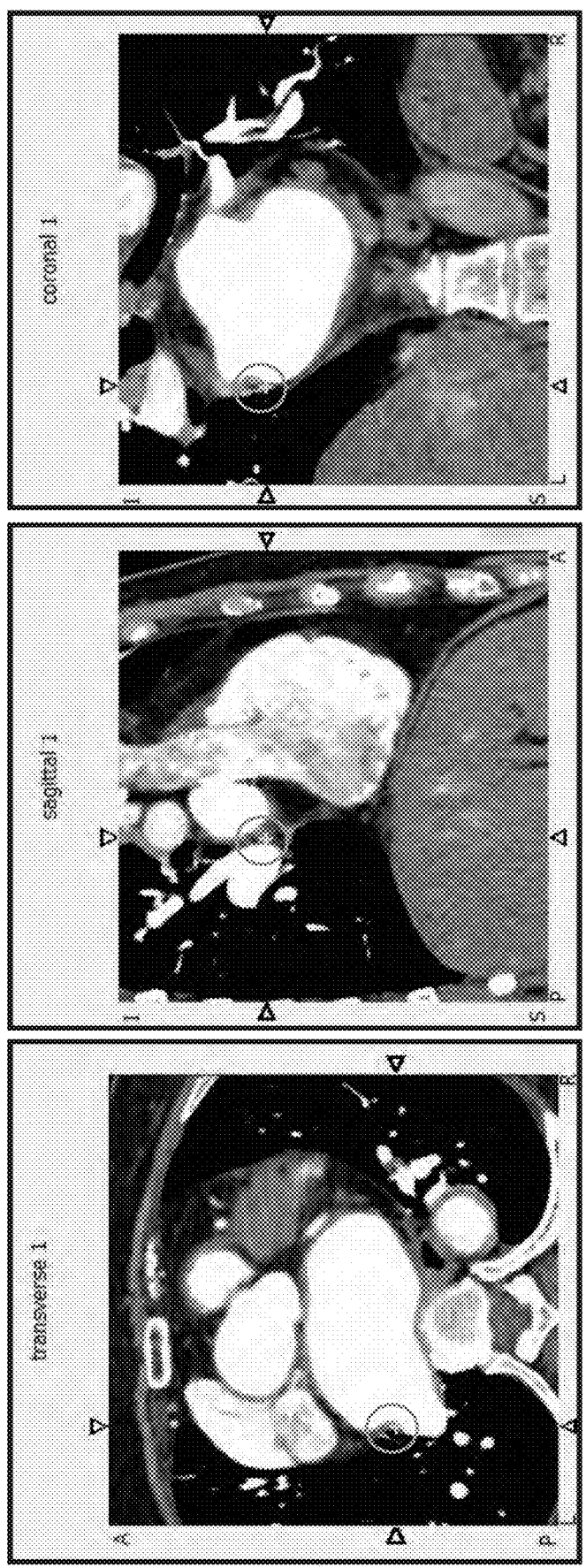
Figure 44D:
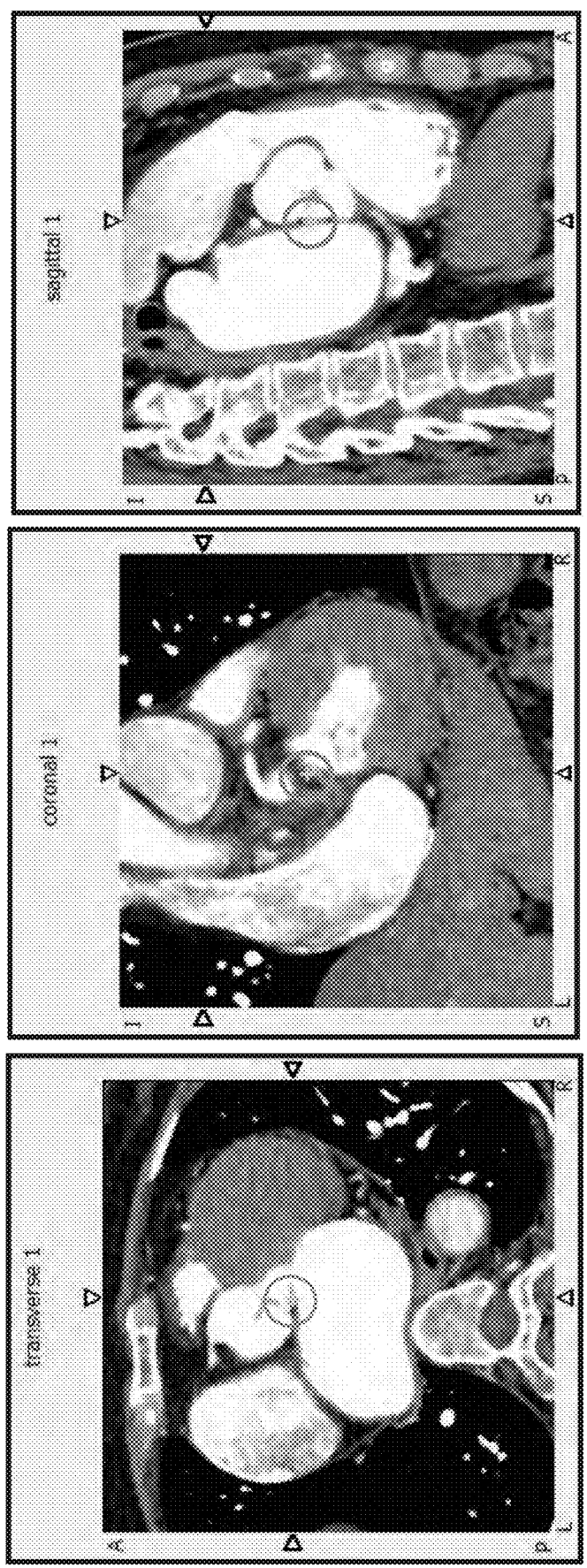
Figure 45:
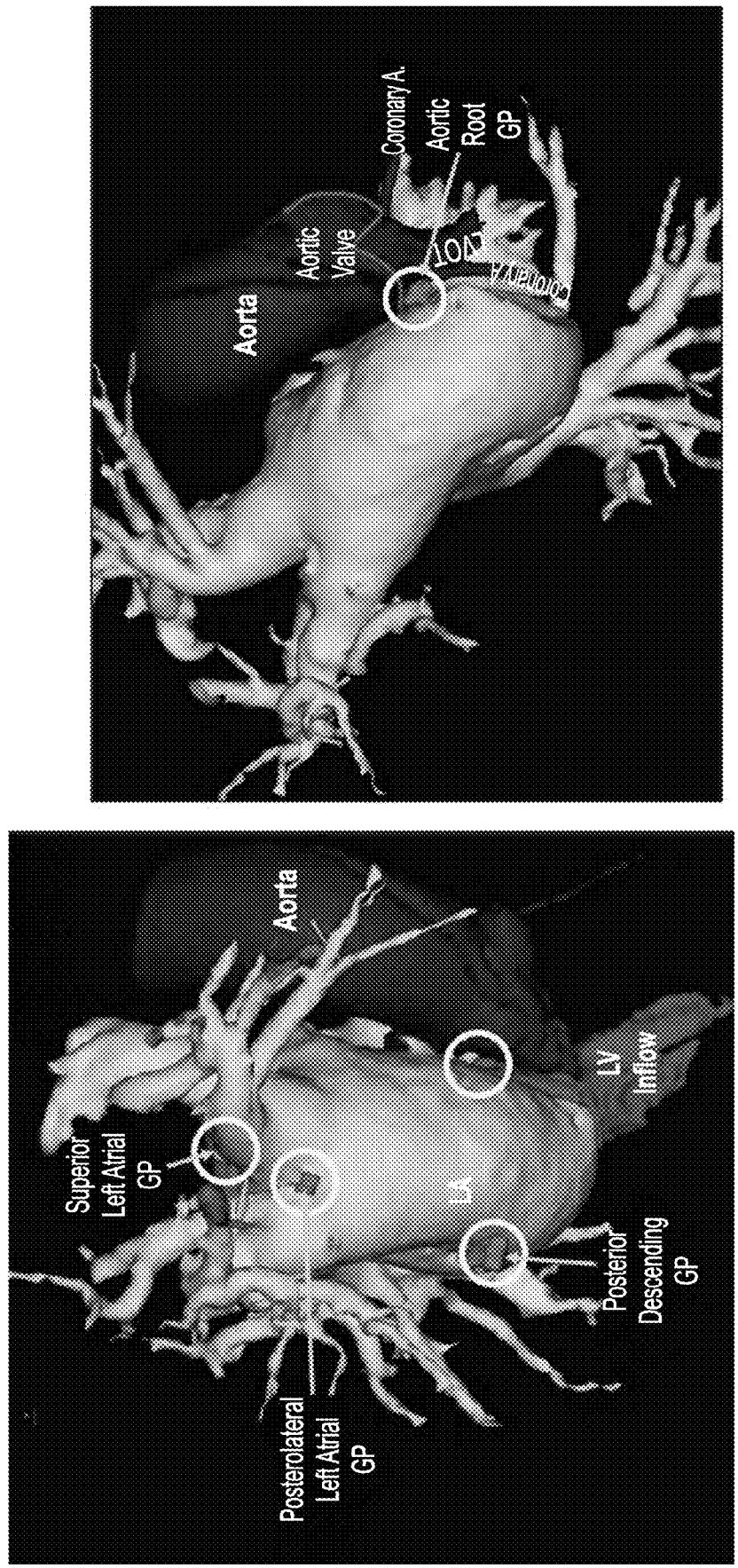
Figure 46A:
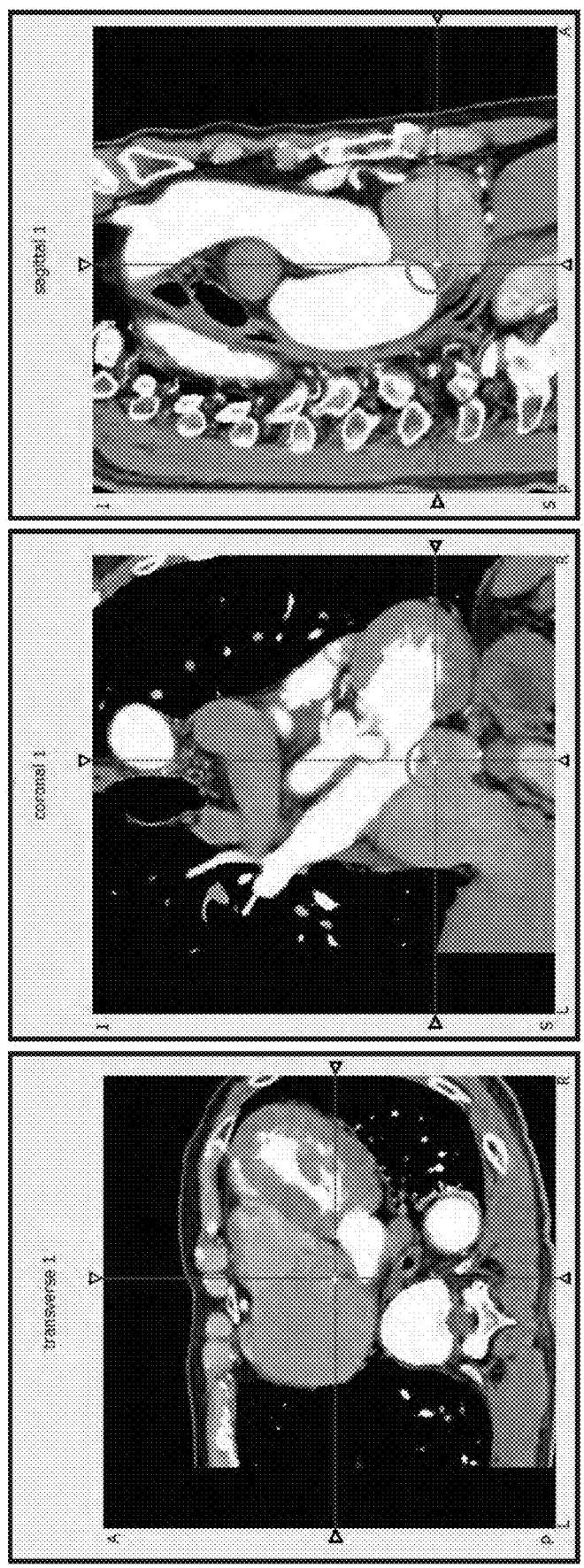
Figure 46B:
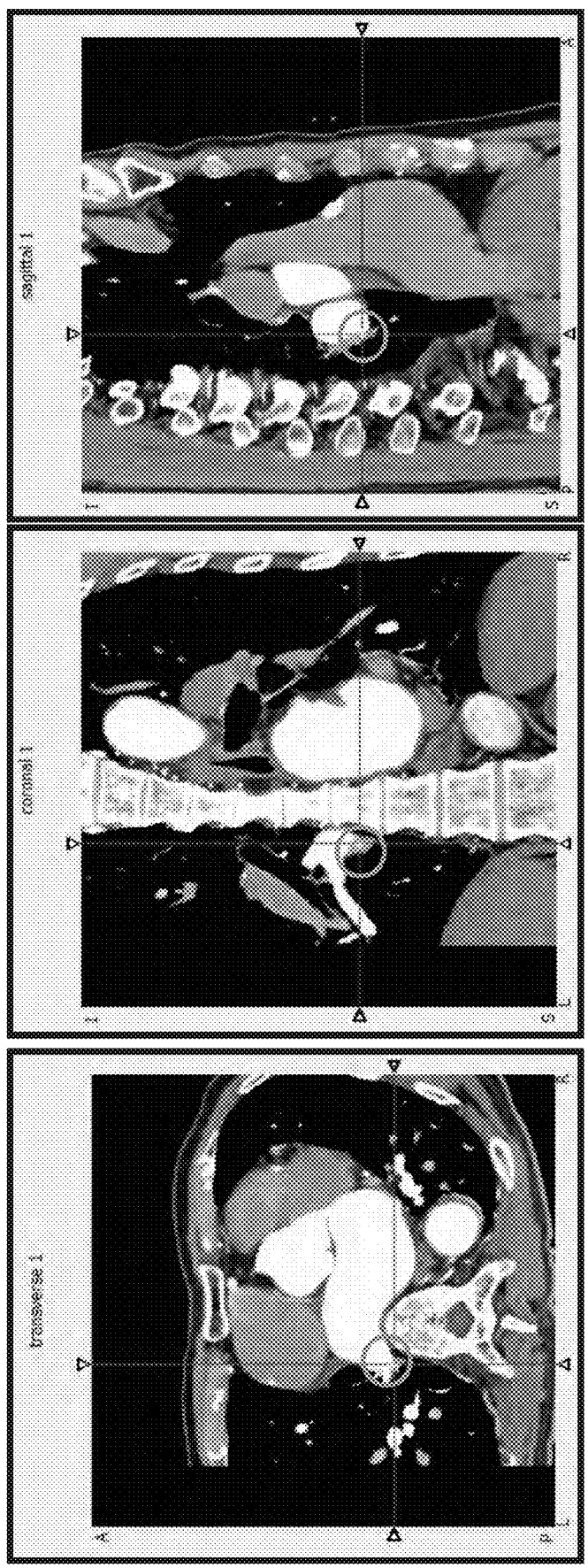
Figure 46C:
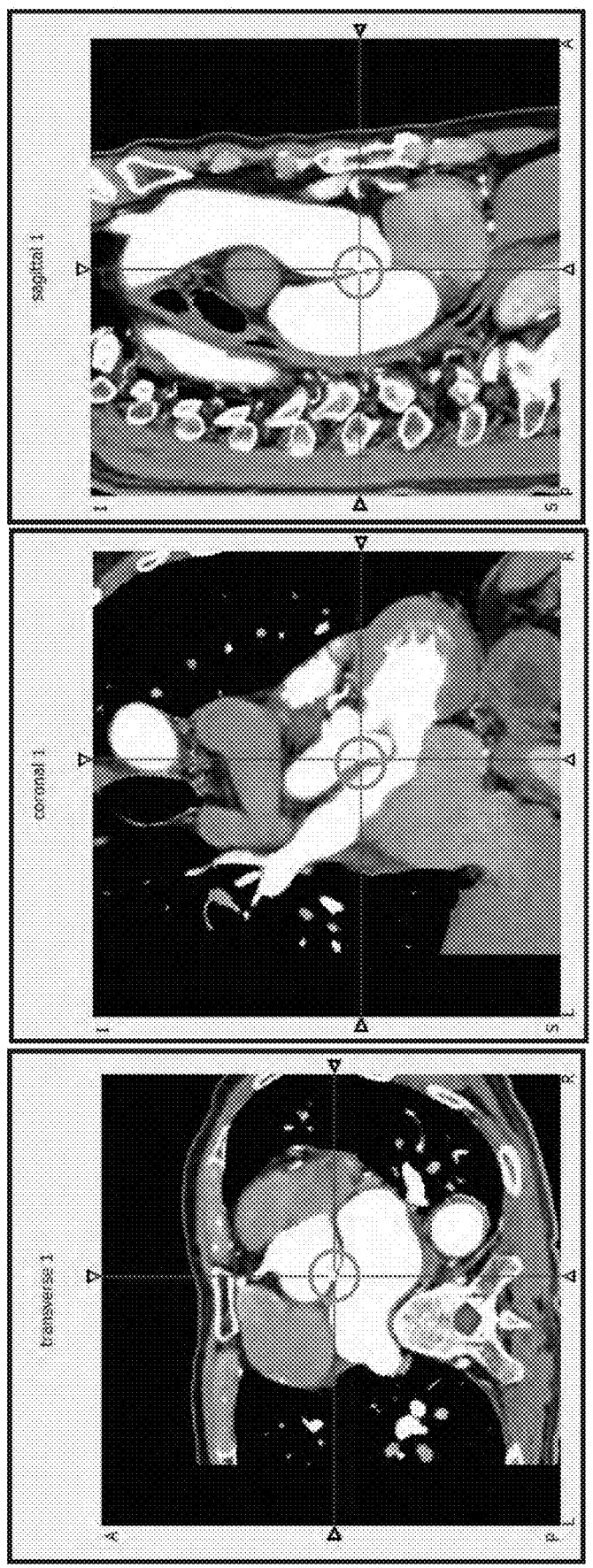
Figure 47:
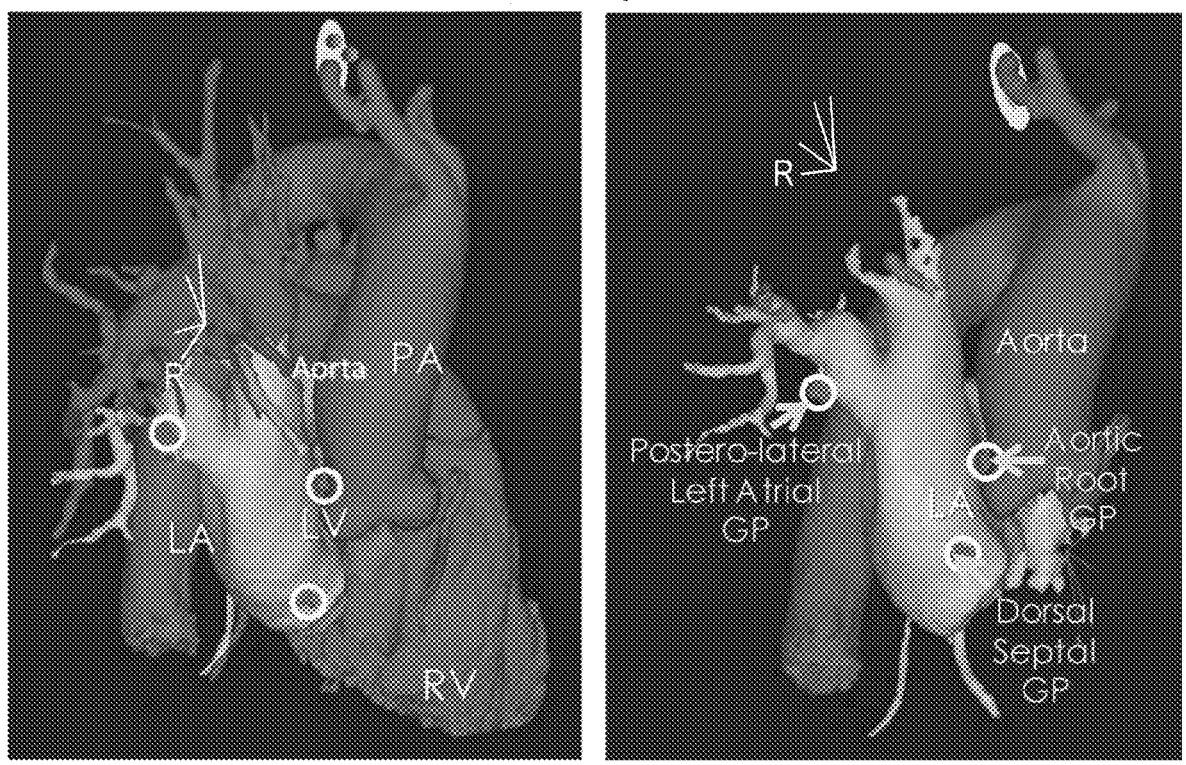

FIG. 15 shows an image of the left atrium colored in accordance with mIBG activity, according to exemplary embodiments of the invention;

FIGS. 16, 17, 18, 19, 20 show steps in treatment of GP sites, according to some embodiments of the present invention;

FIGS. 21A, 21B, and 21C show GP sites localized, according to exemplary embodiments of the invention, where each one of these figures includes, from left to right, a transverse cut image, a coronal cut image, and sagittal cut image;

FIGS. 22A and 22B show the GP sites of FIGS. 21A, 21B, and 21C after estimated locations have been correlated with a map of typical anatomical GP locations in the heart;

FIG. 22C shows the GP sites of FIGS. 21A, 21B, and 21C after estimated locations have been overlaid on sympathetic synapse density maps;

FIGS. 23A, 23B, 23C and 23D show GP sites localized, according to an exemplary embodiment of the invention, where each one of these figures includes, from left to right, a transverse cut image, a coronal cut image, and sagittal cut image;

FIG. 24 shows the location of localized GP sites integrated into a Carto system for ablation guidance, according to some embodiments of the invention;

FIG. 25 depicts HFS application site (marked with a circle having a dashed pattern) on a 3D simulation of the heart of a patient and localized according to some embodiments of the present invention;

FIG. 26 depicts a negative response to the appliance of HFS in the application site depicted in FIG. 25;

FIGS. 27A and 27B depict HFS application site (marked with a circle having a dashed pattern) on a 3D simulation of the heart of a patient and localized according to some embodiments of the present invention;

FIG. 28 depicts a positive response to the appliance of HFS in the application site depicted in FIGS. 27A and 27B;

FIGS. 29 and 30 depict repeating the HFS application at the GP Site depicted in FIGS. 27A and 27B;

FIG. 31 depicts a positive response to the appliance of HFS in the application site depicted in FIGS. 29 and 30;

FIGS. 32 and 33 depict HFS application site (marked with a circle having a dashed pattern) on a 3D simulation of the heart of a patient and localized according to some embodiments of the present invention;

FIG. 34 depicts a positive response to the appliance of HFS in the application site depicted in FIGS. 35 and 36;

FIGS. 35 and 36 depict ablation site (marked with a circle having a dashed pattern) on a 3D simulation of the heart of a patient and localized according to some embodiments of the present invention;

FIGS. 37 and 38 depict negative HFS response in a post ablation measurement;

FIG. 39 depicts an ablation site (marked with a circle having a dashed pattern) on a 3D simulation of the heart of a patient and localized according to some embodiments of the present invention;

FIGS. 40 and 41 depict a negative HFS response in a post ablation measurement;

FIGS. 42 and 43 depict an ablation site (marked with a circle having a dashed pattern) on a 3D simulation of the heart of a patient and localized according to some embodiments of the present invention;

FIGS. 44A, 44B, 44C and 44D show GP sites localized, according to an exemplary embodiment of the invention, where each one of these figures includes, from left to right, a transverse cut image, a coronal cut image, and sagittal cut image;

FIG. 45 shows the location of localized GP sites integrated into a Carto system for ablation guidance, according to some embodiments of the invention;

FIGS. 46A, 46B, and 46C show GP sites localized, according to an exemplary embodiment of the invention, where each one of these figures includes, from left to right, a transverse cut image, a coronal cut image, and sagittal cut image; and FIG. 47 shows the location of localized GP sites integrated into a Carto system for ablation guidance, according to some embodiments of the invention.

DESCRIPTION OF EMBODIMENTS OF THE INVENTION

The present invention, in some embodiments thereof, relates to methods and systems of imaging and, more particularly, but not exclusively, to methods and systems of medical localizing and/or monitoring and/or imaging and/or mapping using a functional imaging modality, for example, single photon emission computed tomography (SPECT).

As used herein, the phrase functional imaging modality means an imaging modality that is designed to or otherwise configured to produce functional based data and/or images (e.g., of an intrabody organ or a part thereof), for example, a nuclear based modality such as single-photon emission computed tomography (SPECT), positron emission tomography (PET), functional magnetic resonance imaging (fMRI), or other modalities. The images may be based on changes within tissues, for example, chemical composition (e.g., at nerve synapses), released chemicals (e.g., at synapses), metabolism, blood flow, absorption, or other changes. The images may provide physiological functional data, for example, activity of nervous system tissue.

As used herein, the phrase anatomical imaging modality means an imaging modality that is designed to produce structural based data and/or images (e.g., anatomical image), for example, X-rays, ultrasound (US), computed tomography (CT), such as x-ray or gamma-ray, magnetic resonance imaging (MRI), or other modalities. Organs, tissues and/or other structures may be detected by the anatomical image.

The present invention, in some embodiments thereof, relates to the use of radiolabeled tracers (also referred to as radiotracer or radioagent or tracer) and/or radiopharmaceuticals, for example, a metaiodobenzylguanidine (mIBG) tracer or another imaging agent for imaging and/or localization (e.g., medical localizing) and/or monitoring and/or mapping (e.g., to obtain synapse distribution in an organ) of the autonomic nervous system (and more particularly for identifying nervous tissue, GP, or other structures) and diagnosis and/or treatment thereof. Optionally, the radiolabeled tracer is a nervous activity tissue marker, for example, denoting activity of neurotransmitters such as norepinephrine (NE). As used herein, the terms marker, imaging agent, and radioactive tracer, and radiolabeled tracer are all interchangeable. Optionally, nerve tissues are detected, for example, the presence of significant nerve tissues is detected (e.g., GPs innervating the organ of interest) over non-significant nerve tissue (e.g., GPs innervating other organs).

An aspect of some embodiments of the invention relates to diseases, medical conditions and/or disease conditions (may be used interchangeably herein) that may be caused, exacerbated or sustained, or otherwise affected by input or involvement of the autonomic nervous system (ANS). Examples of such disease conditions include hypertension, cardiac arrhythmias, diabetes and irritable bowel syndrome. In some embodiments of the invention, such disease conditions may be diagnosed and/or monitored. In some embodiments, such disease conditions may be treated by input or involvement of the autonomic nervous system, e.g., GP ablation.

Some embodiments of the invention relate to means and/or methods for use of such means for detecting the connection between the autonomic nervous system and the organ affected by improper activation of the autonomic nervous system (e.g., innervated organ), for example, based on a combination of functional imaging data and optionally anatomical imaging data.

Some embodiments of the invention relate to means and/or methods for use of such means for diagnosing the disturbance and/or improper activation of the ANS, for example, by comparing acquired functional imaging data or information derived therefrom to a set of reference data (e.g., reference images—for example: of the same patient or a healthy person).

Some embodiments of the invention relate to means and/or methods for use of such means for determining and/or guiding a therapy for the disease, for example, by providing reconstructed functional imaging data that identifies the location of nervous tissue for registration with anatomical images (e.g., to a treatment navigation system, such as CartoMerge™ module).

Also provided in accordance with some embodiments of the invention are means and/or methods for monitoring or guiding the therapy and/or following up on the patients treated (e.g., every few days, weeks, months and/or years and/or according to progress of the disease and/or change in treatment regimen). For example, following up may include monitoring the nerve tissues e.g., locating and tracking over time to detect changes. Optionally, the therapy may be modified, e.g., stopped, continued, increased and/or changed, based on data obtained in the following up.

An aspect of some embodiments of the invention relates to identifying nervous tissue, for example cardiac related nervous tissue, gastrointestinal related nervous tissue, smooth muscle related nervous tissue, and/or nervous tissue associated with other organs and/or tissues. In some exemplary embodiments of the invention, the nervous tissue detected and/or identified includes synapses and/or nervous tissue which innervates a target tissue, such as the heart, bladder, eye, gastrointestinal organs (e.g., stomach, intestines), respiratory related tissues, muscles, glands, liver, pancreas, adrenal, kidney, sexual organs, bladder, or other organs and/or tissues. Additional examples of innervated tissue are provided with reference to FIG. 1.

In some exemplary embodiments of the invention, the innervating tissue is automatically identified and/or otherwise visually presented and/or measured by injecting a marker selectively taken up by nervous tissue (e.g., mIBG). Optionally, anatomical segmentation is used to distinguish between innervating nervous tissue (e.g., to a target organ) and separate nervous tissue (e.g., not to the target organ), and/or either or both from other tissues (non-nervous tissue e.g., fat, muscle, connective tissue, glands). Optionally, both types of nervous tissue are shown. Optionally or alternatively, structural and/or functional limitations on the separate nervous tissue, such as size, location and/or shape are used to distinguish between innervating nervous tissue, separate nervous tissue, and other tissues. In some exemplary embodiments of the invention, the relative amount of innervation and/or activity of innervating nervous tissue may be determined by calculating a relative amount of activity in different parts of said tissue, with respect to the injected radioisotope—e.g., nervous activity tissue marker.

In some exemplary embodiments of the invention, an image may be displayed showing both functional and structural details of an organ (e.g., heart) and of the nervous system (e.g., nerves innervating the organ). In some exemplary embodiments of the invention, functional details of the nervous system include both synapses and ganglions. Optionally or alternatively, functional details of the heart include metabolism (e.g., based on uptake of, for example, Sestamibi).

An aspect of some embodiments of the invention relates to distinguishing afferent nervous activity from efferent nervous activity. In some embodiments of the invention, imaging of nerve tissue, such as synapses and/or ganglions at two points along a conduction pathway of a nervous system, is provided, while a portion of the nervous system not between the two points is stimulated. The order and/or intensity with which the two imaged points are affected by the stimulation may indicate whether afferent or efferent nerves are being stimulated and/or their specific pathways (e.g., connection network along which simulation point lie) and/or locations (e.g., confirm the location of nerves at the stimulation point and/or locate nerves connected to the stimulation point). For example, afferent nerves, when stimulating an organ, for example, the heart, the intestines, the eye, the bladder, smooth muscle, or other organs, will light up (show increased uptake of radioactive tracers) in the synapses compared to the baseline state (e.g., the state before stimulation). Optionally, nervous circuits and/or conduction pathways may be identified by noting the order of excitation of nervous tissue and/or its discrete location with respect to the location of the stimuli (e.g., central or peripheral). The distinction between afferent and efferent nerves may be based on combined anatomical and functional imaging data, and/or on methods for locating the position of nerve structures, as described herein. For example, the location of the stimulated nerves may be displayed on an anatomical image.

Some embodiments of the inventions may include imaging synapse distribution using a single photon emission computed tomography (SPECT and/or the use of radiolabeled metaiodobenzylguanidine (mIBG) tracer or another imaging agent in such imaging.

An aspect of some embodiments of the invention relates to diagnosis and/or therapy control based on synapse distribution in an organ (e.g., in the heart).

In some exemplary embodiments of the invention, abnormal synapse distribution and/or activity may be determined by comparing the distribution imaged with one or more sets of expected or "normal" distributions. Optionally, different expected distributions may be provided for comparison in different situations, such as per gender, age, nationality, disease state, medication, stress, exercise, stimulus or stimuli. Optionally, a disease may be identified based on a match between the imaged distribution and/or activity and one or more sets of distributions characterizing diseases and/or conditions. Optionally, reference sets of synapse distributions characterizing diseases and/or conditions may be acquired for a range of patients. Similarly, reference sets of synapse distributions characterizing healthy people may be acquired for a range of healthy people. A set of distributions imaged from a particular patient may be compared with one or more reference sets for diagnosing the state of the particular patient. Such comparison may be based on characterization of the reference sets and the set imaged from the particular patient, for example, by relative intensities, location and/or sizes of hot-spots (e.g., areas of relatively higher intensity indicating activity of nerves) and/or intensities, location and/or sizes of cold spots (e.g., areas of lower intensity, indicating lack of activity or lower activity of nerves).

In some cases, synapse distribution (e.g., density) may teach about a disease process and/or about any remodeling that the nervous system may be undergoing or gone through. It is important to note that in many patients, the nervous system is highly dynamic in nature and the density and activity of the system and the system components (e.g., ganglia, synapses, sympathetic, parasympathetic, efferent and afferent) respond to the disease and to the response of the body as a result of the disease or a therapy. In some embodiments, the disease and/or state may be identified based on a change in nervous tissue between two imaging sessions and/or taking into account treatment provided in the interim.

In some embodiments of the invention, diagnosis may take into account both distribution and activity of synapses in the imaged region. For example, synapse distribution may indicate potential reactivity of innervated tissue, and synapse activity may show the degree of utilization of that potential. The combination of distribution and activity may also show the evenness of innervation and/or stimulation/control of the tissue by the nerves, for example, the heart by the imaged portion of the neural system.

In some embodiments of the invention, diagnosis may be used to estimate damage and/or prognosis of healing from a cardiac infarct. For example, it is sometimes the case that damage to nervous tissue is different from damage to cardiac muscle and/or that nerve regeneration is different in different tissues and/or for different nerve types. Imaging of the heart may indicate, for example, portions of the heart which are not suitably innervated and thus may be the cause of cardiac chamber remodeling, mitral regurgitation, heart failure and/or cardiac dis-synchrony.

In some embodiments of the invention, the effect of a treatment meant to affect nervous tissue, such as beta blockers and/or renal (or other) denervation, may be measured and/or tracked, optionally by comparing nerve activity to response (e.g., mechanical, electrical, chemical) of the organ (e.g., for heart: amount and/or velocity of wall movement). Optionally, the treatment may be modified, e.g., stopped, continued, increased and/or changed, based on the measurements.

In some embodiments of the invention, the effect of a chronic condition such as, for example, hypertension, diabetes and/or stress may be tracked by tracking one or both of synapse distribution and/or activity, optionally in conjunction with ganglion activity and/or cardiac response.

In some embodiments of the invention, the functional measurements and/or diagnosis described herein may be used to select placement for pacemaker or other cardiac electrical controller electrodes. For example, electrodes used for arrhythmia treatment may be optionally placed where they can subdue, dampen and/or capture more highly activated tissue.

In another example, pacemaker electrodes may be placed according to an expect effect of the electrical stimulation on nervous activity and/or conductions. In another example, electrodes may be placed so as to block conduction of stimuli from one area to another area and/or to reduce reactivity of cardiac tissue according to over-activity of nervous tissue.

In other examples, the functional measurements may be used to guide ablation of nerves fibers, ganglions and/or the outer surface of an organ—e.g., the heart. Optionally, measurement may be applied after ablation (possibly during an ablation procedure) to determine an effect of ablation and optionally repeat or modify as needed.

In some embodiments of the invention, the functional measurement may be used to select locations for drug eluting patches which elute, for example, stimulating or inhibiting chemicals to the heart and/or nervous tissue and/or which elute materials which encourage growth of nervous tissue.

In some embodiments of the invention, diagnosis may include identifying parts of an organ (e.g., the heart) which do not react as desired when an increase in demand is placed on the organ, for example, based on reduced activity and/or reduced mechanical reaction. In some embodiments of the invention, a map showing delay in activation time and/or conduction velocity may be correlated with nerve activation. Such a correlation map may be used to identify, for example, locations which are over activated in an attempt by the heart to compensate for delayed activation and/or conduction problems. In some embodiments of the invention, a therapy may include balancing (or changing the balance in a desired way) the activity of certain regions for example, by modulating the neural tissue input and/or or affecting the underlying or associated heart condition.

In some embodiments of the invention, such functional measurements may be used to assess causes for hypertrophy and/or hypotrophy in some or all of the innervated organs. For example, patients with right ventricular heart failure may present compensatory neural activation of the weaker tissue, which in some cases will have a spillover effect on the normal tissue. Neural activity beyond a certain level will cause a reduction in heart activity that can be treated by local blockade of the improper increase in compensatory neural stimulation. Such spillover may also be implicated, for example, in arrhythmia.

An aspect of some embodiments of the invention relates to a method of detecting or localizing ganglions in functional (e.g., SPECT) data. The method may include viewing and/or analyzing (e.g., by a processor) functional data at multiple resolutions (e.g., different sizes of image masks as described below) and/or object filter sizes (e.g., selecting objects above a minimum size threshold), and identifying as ganglia those objects which appear in multiple sizes of filters. One or more parts of the method may be automatically performed by hardware and/or software. Some embodiments of the invention relate to a method of detecting ganglions by using an imaging agent, for example, radiolabeled agents, for example, a metaiodobenzylguanidine (mIBG) tracer, or other suitable imaging agents.

According to some embodiments of the present invention, there are provided methods and systems of localizing or detecting a nervous tissue, for example ganglia, based on functional imaging modality data (e.g., functional image), optionally in combination with anatomical imaging data (e.g., anatomical data), for example before and/or during and/or after a treatment procedure (e.g., heart treatment procedure).

Nervous tissue areas, such as the ganglia, are relatively small and having a limited uptake of an imaging agent in relation to surrounding tissues. The combination of functional (e.g., SPECT) data with anatomical data may allow selecting regions of interest (ROIs) that limits the area from which data for reconstruction (e.g., data for localizing or detecting a nervous tissue) may be gathered. The ROIs may be selected based on the anatomical data. Such a selection may increase the signal to noise ratio (SNR) as noises from surrounding tissues are filtered. The anatomical data is optionally gathered using other imaging modalities, such as CT, MRI, fluoroscopy modality, Ultrasound, and/or the like. Additionally or alternatively, one or more anatomic landmark(s) may be detected from an analysis of the SPECT data, for example based on the uptake and/or the uptake rate of the imaging agent which is set to be engulfed by the nervous tissue and/or by an imaging agent not engulfed by the nervous tissue. The detected anatomic landmarks may be used for registration with an anatomical image. Optionally, dynamic behavior of the imaging agent during a monitoring period may be used as a differentiator of the location of the nervous tissue. In some embodiments, the functional data (e.g., SPECT data) may include kinetic data which is indicative of an uptake rate during a monitoring period, for example in one or more ROIs in a target intrabody volume. For example, the SPECT data may include functional data acquired by monitoring an uptake rate of an imaging agent such as a radio labeled metaiodobenzylguanidine or a cocktail that includes radio labeled metaiodobenzylguanidine.

Optionally, the functional (e.g., SPECT) data may be combined with anatomical data captured during an ablation procedure, for example during denervation of ganglionic plexi in proximity to the atria of a patient's heart, renal denervation, a liver treatment, a spleen treatment, and/or an intestine treatment. Optionally, the functional data may be combined with anatomical data for diagnosis, for example for determining whether to perform a heart treatment such as neural modulation or ablation for treatment of different disease states including heart arrhythmia, congestive heart failure and ischemic heart disease.

Optionally, functional (e.g., SPECT) data may be captured in advance and forwarded to a workstation for combination with anatomical data, for example during and/or before a treatment procedure, e.g., a heart treatment procedure. For example, the combination may be performed using a CartoMerge™ module. Optionally, SPECT data and anatomical data, such as fluoroscopy data, are combined for performing a catheterization procedure, allowing an operator to identify and/or localize target nervous tissue and optionally to navigate and/or guide a treatment probe to proximity with the target nervous tissue (e.g., to contact the target nervous tissue). The treatment probe may be, for example, an ablation device, for example an intraoperative ablation device, a non invasive ablation device, and/or a minimally invasive ablation device. Alternatively or additionally, the treatment device may include an RF probe, magnetic-based catheter and/or a Cryosurgery probe.

In some embodiments, functional data and anatomical data, may be combined for performing a catheterization procedure, allowing an operator to navigate a treatment probe or an imaging probe.

In some embodiments, functional data may allow localizing tissue (e.g., nerve structures) that cannot be localized by anatomical imaging alone. For example, hidden functional portions of an organ may be localized by visualizing their functionality. In some embodiments, this may be combined with enhancing the resolution of functional imaging, for example, by focusing the functional imaging on regions expected to include the anatomical imaging hidden functional portions. These regions may be identified, in some embodiments, based on structural imaging.

Optionally, anatomical data is used for instructing the reconstructions of functional (e.g., mIBG) activity mapping functional images in a manner that the resolution of areas wherein the nerve structures (e.g., GP, ganglia) are located is increased. Optionally, reconstruction is performed with anatomically varying gating, for example, anatomically varying image masks.

For example, nervous tissue in the atria, such as individual ganglia, are commonly surrounded by fatty connective tissue closely adjacent to epicardial muscle. Other ganglia in the atria are imbedded in the fat pad overlying the posterior surface of the left atrium and/or in the atrioventricular groove. The close proximity of these ganglia to a fat layer may prevent an operator (manually) or a processing module (automatically) from localizing the ganglia based on the anatomical data. The combination with the functional data provided by the SPECT data (for example) however, may allow separating between the ganglia and the surrounding tissues based on the uptake rate of the imaging agent, kinetic data and/or dynamic behavior.

Optionally, the nerve structure (e.g., GP) is identified, rather than the fat pad. Optionally, the nerve structure itself is identified within the fat pad, rather than identifying the fat surrounding pad. Alternatively or additionally, the fat pad is used as an anatomical guide for detecting the GP within the fat pad, for example, with reference to the image mask method described below (e.g., FIG. 2B), image masks may be generated using anatomical images to correspond with the fat pad. The GPs within or next to the fat pads are then identified within functional data based on the application of the image masks to the GP.

Optionally, during ablation, the GP within the fat pad is targeted for ablation. Optionally, the ablation is selected to ablate the GP, rather than the surrounding fat pad. The surrounding fat pad may not be entirely removed, for example, most of the fat pad may remain, or some of the fat pad, for example, no more than about 25%, or about 50%, or about 70%, or about 90% of the fat pad. The fat pad ablation may be performed as required to ablate the GP inside and/or near the fat pad. The entire fat pad may be removed, for example, as a secondary effect of ablating the GP, rather than being the primary target.

An aspect of some embodiments of the present invention relates to a method of processing functional images to identify and/or locate nerves (e.g., GPs) within tissues (e.g., heart, stomach, intestines, kidney, aorta, or other organs or structures). Optionally, anatomical images used to reconstruct the functional image and/or process the functional data are combined with the functional images, the combined image may be used as a basis for locating GPs. The method may comprise generating image masks corresponding to regions of the anatomical image contain the GPs and/or the innervations of the organ. The GPs are not visible on the anatomical image, for example, cardiac GPs on a CT scan that includes the heart. The selected image masks are applied to corresponding locations on the functional image, for example, by a registration process. GP characteristics within the functional image are reconstructed, instructed by the applied mask. GPs within the selected image mask applied to the functional image may be identified, based on predefined rules, for example, size of active spots and/or intensity of the active spots relative to surrounding intensity (e.g. relative to an average value). In this manner, anatomical information is used for reconstructing the activity of GPs within the functional image. The anatomical information, in the form of the mask, may be used for guiding the processing to certain regions of the functional image, to help in locating the GPs of interest. The identified GPs may be displayed on the anatomical image or a combined functional and anatomical image, and/or may be registered with a navigation system for patient treatment such as an electrophysiological catheter navigation system for treating diseases (e.g., cardiac disorders such as arrhythmias). In this manner, the anatomical image may serve as a guide for where to look within the functional data to identify the relevant nerve structures, where the rough location of the nerve structure within the body is known before hand, for example, based on a predefined anatomical atlas.

Optionally, the image mask method may be used to decide where the innervated organ is located and/or to define where to look for objects of interest.

The size and/or shape of the image masks may be defined, for example, by the ability of software to segment the anatomical image, by the resolution of the anatomical and/or functional images, by the resolution of the ablation treatment, by the size of the structure being identified, or other methods.

The image mask method is not limited to detecting nerve structures (e.g, GPs). The image mask method may be used to detect other small structures, for example, small cancer lumps and/or lymph nodes near tissue.

Optionally, image masks are generated for an organ with one or more lumens, fluid and/or air filled and/or potential spaces (e.g., bladder, heart, stomach, intestine, aorta). Optionally, the image masks are generated to identify structures (e.g., nerves, GPs) in the tissue itself, rather than within the lumen and/or space. Optionally, the contour of the organ and/or tissue is identified based on the anatomical image, for example, the inner wall of the heart chambers, stomach, bladder, aorta, or other organs. Optionally, the image masks are generated based on the anatomical image, to guide searches within the functional data to identify the nerve structures.

Figure 1:
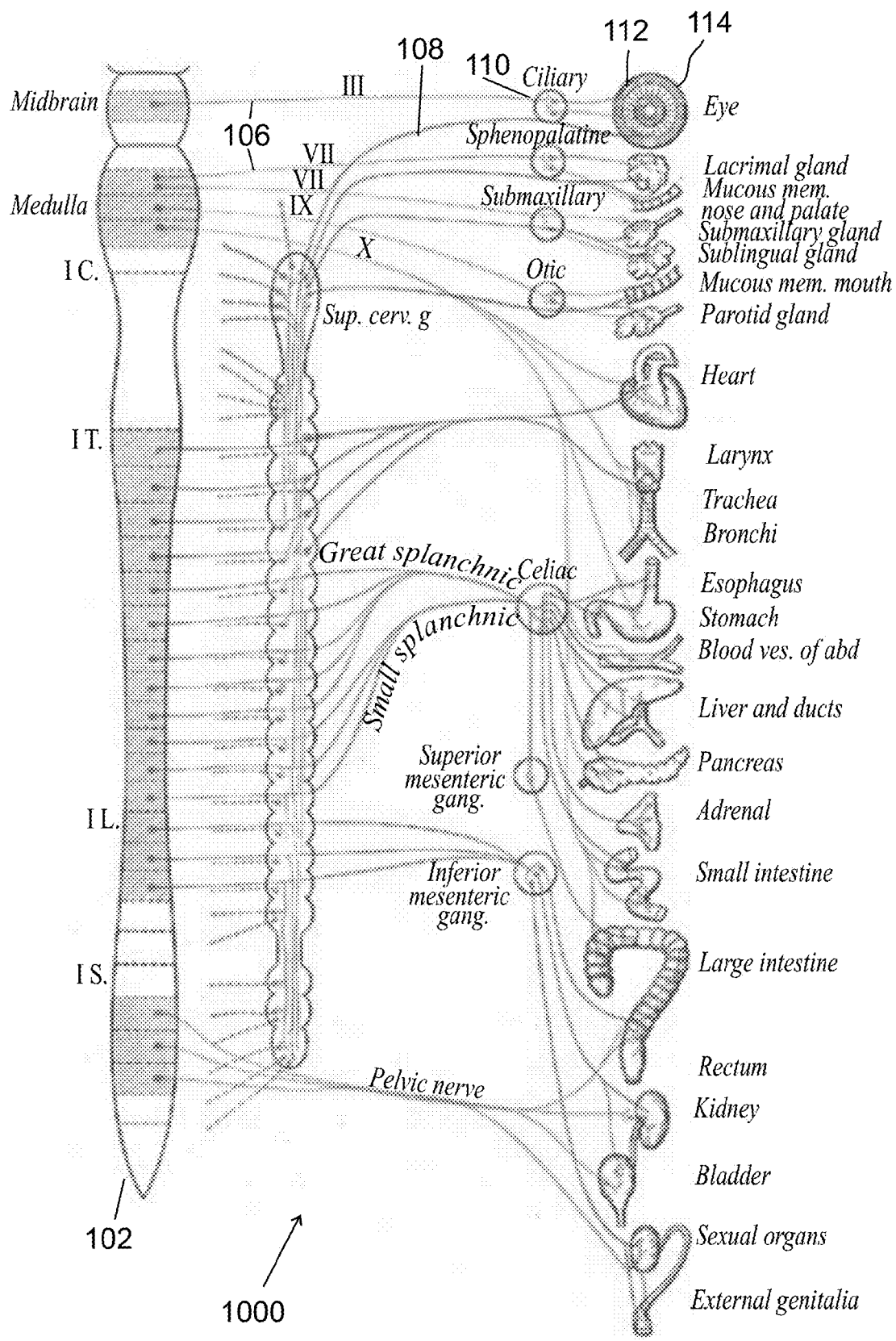

For purposes of better understanding some embodiments of the present invention, as illustrated in FIGS. 2-47 of the drawings, reference is first made to the anatomy and function of an autonomic nervous system (ANS) of a mammal (e.g., human) as illustrated in FIG. 1. FIG. 1 shows the components of an ANS 1000, in schematic form. As can be seen, the ANS includes a network of ganglions, also termed ganglionic plexi (GP). Nerve fibers meet and synapse at the ganglions.

The human body has several control systems, including the hormonal system, the central nervous system and the autonomic nervous system (ANS). As traditionally depicted, the autonomic nervous system is (mostly) not under conscious control and serves to regulate various body functions, including, life sustaining functions. For example, basal heart rate, breathing and digestion are controlled by the autonomic nervous system. In some classifications, the portion of the autonomic nervous system which relates to digestion is termed the enteric nervous system (ENS).

A spinal column 102 provides both sympathetic and parasympathetic enervation. As shown, parasympathetic enervation 106 may proceed directly to organs 114 and/or to secondary ganglia 110. Sympathetic enervation may be modulated by a spinal ganglia and then feed into secondary ganglia 110 or organs 114. In many cases, the sympathetic and parasympathetic enervations interact at the secondary ganglia 110 (e.g., Ciliary, Celiac, etc.). Secondary ganglia 110 may be connected directly to nerve endings at an organ (e.g., 114). In some cases, an intermediary network or chain of ganglia exists as well (not shown).

The ANS is generally considered to include two main functional layers, the sympathetic nervous system (SNS), generally in charge of excitatory and increased responsiveness and control and the para-sympathetic nervous system (PNS), generally in charge of damping responsiveness and control. For example, heart rate is increased by increased activity of the SNS and decreased by increased activity of the PNS. In some organs, such as the heart, the nerve fibers of the SNS and nerve fibers of the PNS meet at certain ganglions. Ganglions which include both SNS fibers and PNS fibers utilize a balance between the excitations of the SNS and PNS to determine their behavior.

The ANS includes both afferent (leading towards the innerverated tissue) and efferent fibers (leading away from the innerverated tissue).

From a perspective of diagnosis, it is recognized that malactivity of the ANS may cause body dysfunction, for example, in atrial fibrillation. Furthermore, general ANS tone is considered to be related to some diseases such as high blood pressure. Damage to the ANS can sometimes occur, causing organ dysfunction, for example, in transplanted organs.

From a perspective of treatment, some examples of treating an undesired condition by ablating a part of the ANS have been suggested.

It is noted that throughout the application, the term GP and/or ganglia may also refer to a synaptic center, to encompass regions other than ganglia (such as where a nerve meets an organ), as it may be difficult to differentiate between a ganglion and a GP. In some cases, the difference between an individual ganglion and a synaptic center comprising a plurality of ganglia (e.g., a ganglionated plexus) is merely semantic (e.g., wherein different people in the art use different terminology) and/or of no significant medical importance.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Figure 2A:
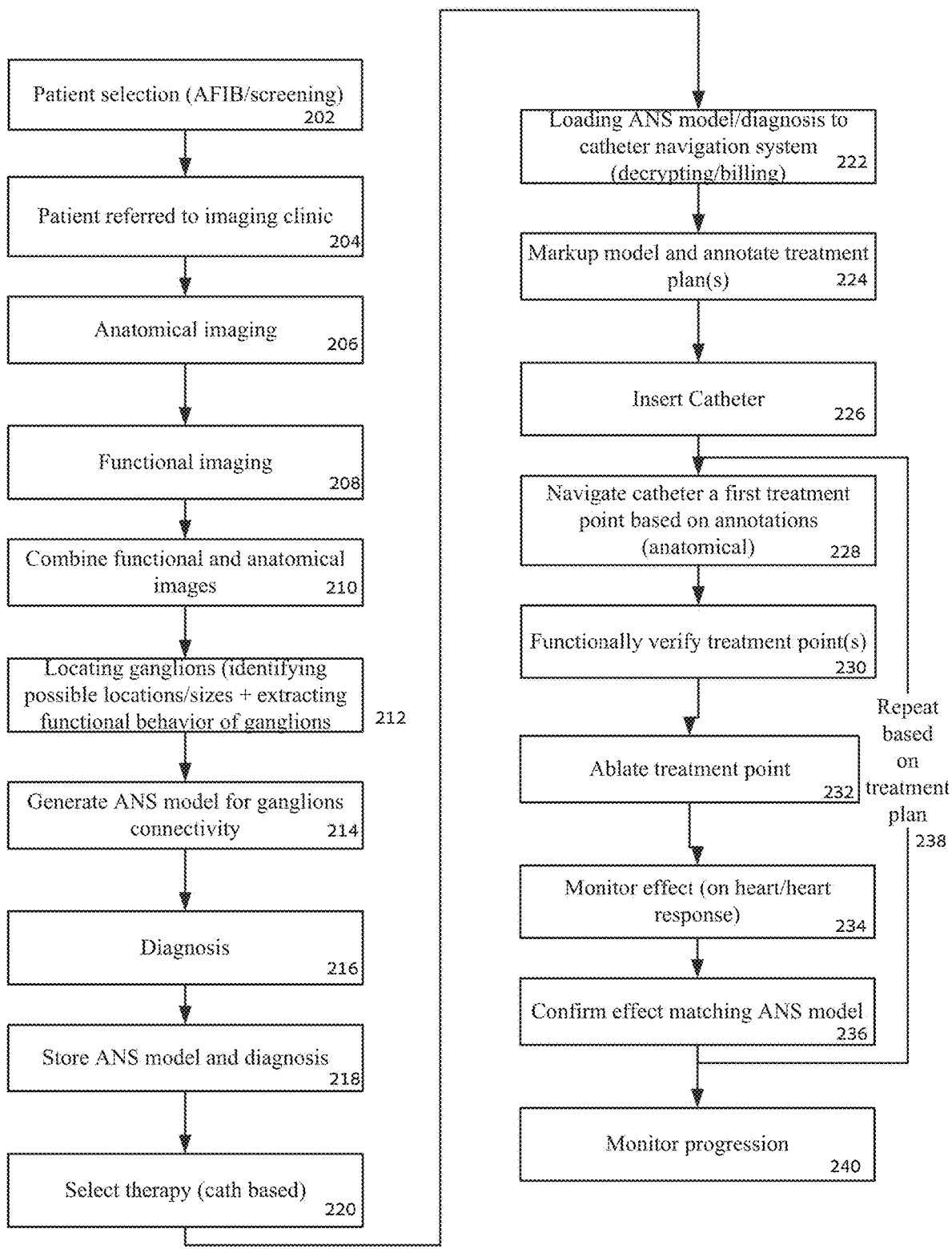

Reference is now made to FIG. 2A, which is a flowchart of a method of localizing and/or detecting and/or identifying, for example imaging and/or mapping, nervous tissue in an intrabody volume by combining functional data (e.g., SPECT data) and optionally anatomical data, according to some embodiments of the present invention. It is noted that in some cases, localization, detection and identification are used interchangeable, for example, when referring to generating data denoting the position of nerve structures. In other cases, localization, detection and identification are not interchangeable, for example, with reference to FIG. 2B, during the process of generating the data of the position of the nerve structures, in which case the terms may denote different stages of the process.

Figure 3:
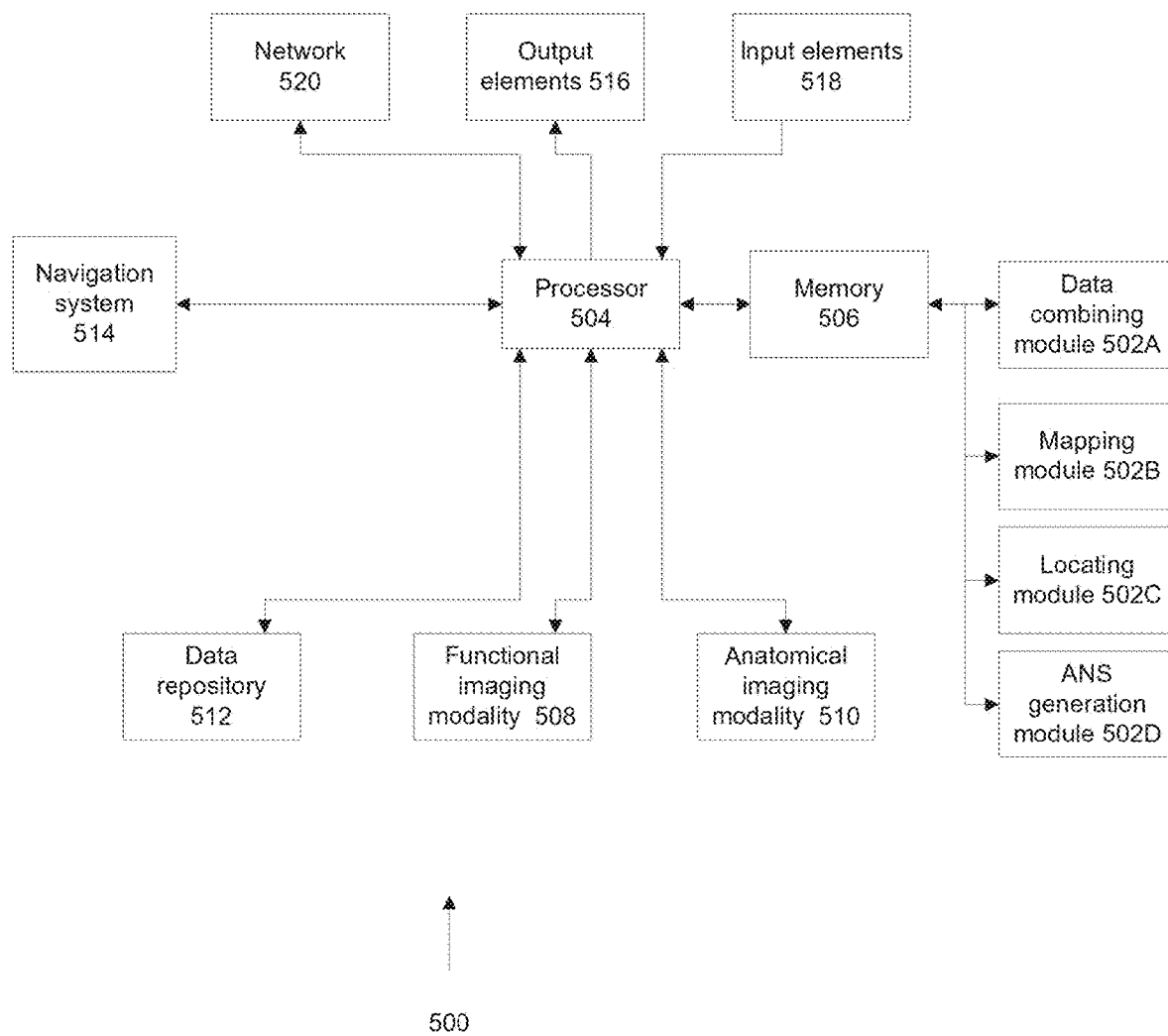

Optionally, method 200 includes a method of treating a patient based on the localized and/or detected nervous tissue. Optionally, at least some blocks of method 200 are computer-implemented. Optionally, at least some blocks are performed manually by an operator. Reference is also made to FIG. 3, which is a system 500 for localizing and/or detecting nervous tissue and/or other ANS components in an intrabody volume by combining functional data and anatomical data, according to some embodiments of the present invention. One or more blocks of the method of FIG. 2A may be performed by system 500 of FIG. 3, for example, one or more modules 502 corresponding to parts of the method. Optionally, system 500 or one or more components of system 500 is an image data processing unit.

Optionally, the method and/or system are integrated with a navigation system, for example, the CARTO® system manufactured by Biosense Webster®, and/or the MediGuide™ System manufactured by St. Jude Medical™. The navigation system may perform one or more of the following functions: map electrical activity in the heart, show where ablation was performed, allow navigation (e.g., of the treatment catheter) to where the map directs to get to in order to ablate, navigate around the point indicated on the mat to further pinpoint the GP. Optionally, one or more blocks of the method of FIG. 2A (e.g., related to the treatment) are driven by the navigation system (e.g., CARTO® system). The treatment may be performed using the navigation system, to ablate nerve structures identified using the systems and/or methods described herein. For example, the coordinates within the CARTO® system space corresponding to the target nerve structures are provided by the system and/or method described herein. Alternatively, navigation is performed under fluoroscopic imaging (or other imaging) and the map that shows function and/or anatomy.

System 500 may include one or more modules 502 having instructions for execution by a processor 504. In some embodiments, one or more modules 502 may be integrated within processor 504. Modules 502 may contain program instructions for execution of one or more blocks of the method of FIGS. 2A-B or other methods described herein. Modules 502 may be stored on a non-transitory computer readable medium such as memory 506.

As used herein, the term "processor" or "module" may include an electric circuit that performs a logic operation on input or inputs. For example, such a processor/module may include one or more integrated circuits, microchips, microcontrollers, microprocessors, all or part of a central processing unit (CPU), graphics processing unit (GPU), digital signal processors (DSP), field-programmable gate array (FPGA) or other circuit suitable for executing instructions or performing logic operations.

The instructions executed by the processor/module may, for example, be pre-loaded into the processor or may be stored in a separate memory unit such as a RAM, a ROM, a hard disk, an optical disk, a magnetic medium, a flash memory, other permanent, fixed, or volatile memory, or any other mechanism capable of storing instructions for the processor/module (e.g., memory 506). The processor(s)/modules may be customized for a particular use, or can be configured for general-purpose use and can perform different functions by executing different software.

If more than one processor is employed, all may be of similar construction, or they may be of differing constructions electrically connected or disconnected from each other. They may be separate circuits or integrated in a single circuit. When more than one processor is used, they may be configured to operate independently or collaboratively. They may be coupled electrically, magnetically, optically, acoustically, mechanically or by other means permitting them to interact.

Optionally, one or more processor(s) 504 are in electrical communication with a functional imaging modality 508. Optionally, processor 504 is in communication with an anatomical imaging modality 510.

Optionally, processor 504 is in electrical communication with a data repository 512, for example, for storing data of the detected nervous tissue, and/or other processing results.

Optionally, processor 504 is in electrical communication with a navigation system 514, for example, for navigating a catheter inside the vasculature of a patient. The operator of navigation system 514 may navigate the catheter based on the detected nervous tissue. Optionally, navigation system 514 is an electrophysiological (EP) navigation system for the heart, or another navigation system for other regions of the body.

Optionally, processor 504 is in electrical communication with one or more output elements 516, for example, a graphical user interface (GUI), a screen for displaying images, a printer, or other output devices.

Optionally, processor 504 is in electrical communication with one or more input elements 518, for example, a keyboard, a mouse, a graphical user interface (GUI), a touchscreen, a microphone for voice recognition, or other input devices. Input elements may be configured to receive inputs from system 500 operator, e.g., a physician.

Optionally, processor 504 is in electrical communication with a network 520, for example, the internet, a local hospital network, a distributed clinical network, or other networks. One or more remote servers may perform some or all of the processing, may store data, may provide upgrades, and/or may be used by remote operators.

Components of system 500 may be sold together and/or in parts. For example, modules 502 may be sold as software for installation on an existing workstation, for example, downloaded from network 520 and/or provided on memory 506. In another example, processor 504, memory 506, and modules 502 are sold together, for example, as a workstation. In another example, the complete system is sold.

In some embodiments, components of system 500 may be provided at different locations and/or as separate devices, e.g., data of the detected nervous tissue may be obtained by module(s) 502, stored on data repository 512 and send to navigation system 514. The data of the detected nervous tissue may be obtained before the treatment starts.

As used herein, the functional data (e.g., SPECT data) may be a SPECT image captured by a suitable SPECT modality, for example, electrocardiogram-gated SPECT (GSPECT) modality, A-SPECT, SPECT-CT, and/or D-SPECT™ of Spectrum Dynamics modality. The specifications of these modalities are incorporated herein by reference.

As used herein, the phrase nervous tissue means Ganglia (i.e., ganglionic plexi, GP), neural fibers, neural synapses, neural sub systems, and/or an organ specific nervous tissue. Examples of neural subsystems include, a peripheral subsystem, and/or an autonomic sub system, such as the sympathetic and the parasympathetic autonomic sub systems. Examples of organ specific nervous tissue may include, a carotid body, aortic arch, pulmonary, renal, splenic, hepatic, inferior mesenteric, superior mesenteric, muscular and/or, penile nervous tissue. It should be noted that the localization or detection may be performed with and/or without reconstruction of an image based on the functional data. For example, localization or detection may be performed by identifying an imaging agent signature, in the functional data without reconstructing the functional data to form a spatial image. Nevertheless, an image reconstructed from the functional data may be analyzed to localize and/or detect the nervous tissue. In such embodiments, the functional data may be processed to identify an imaging agent signature of a target nervous tissue. This target tissue signature may be indicative of the location of the target nervous tissue. The imaging agent signature may include kinetic information, uptake information of one or more imaging agent(s), washout information of one or more imaging agent(s), and/or one or more combination(s) thereof. The target nervous tissue signature may be measured relative to a background in an intrabody volume (e.g., as provided by an image mask) and/or using previously captured functional data of most probable location, number, size, and/or the like.

Referring back to FIG. 2A, optionally, at 202, a patient is selected for disease screening, evaluation and/or treatment based on identification of nervous tissue. Optionally, the patient is selected based on a hypothesis that the patient is suffering from improper activity of the ANS, for example, over activation and/or improper activation. Optionally, the patient is selected based on a hypothesis that the patient may be treated by ablation or injection of a therapy, and/or other therapies of the identified portions of the ANS. For example, the patient may be suffering from atrial fibrillation (AFIB) secondary to improper activity of the ANS innervating the heart. The patient may be selected, for example, manually by a physician and/or automatically by software, for example, software that detects one or more inclusion criteria within the electronic medical record of the patient.

Optionally, at 204, the selected patient is referred to an imaging clinic for obtaining images or other data for detection of the nervous system (e.g., for identifying one or more components of the ANS—such as GPs).

Optionally, at 206, anatomical data which optionally includes anatomical images, for example fluoroscopy images, of an intrabody volume of a patient (e.g., a patient organ) on a patient surface and/or volume may be captured, e.g., by using an anatomical imaging modality (e.g., modality 510), such as a fluoroscopy modality, CT and/or other anatomical imaging modalities. For brevity, the term anatomical data may include locational data of an intra-body treatment probe and/or locational data gathered using an intra-body treatment probe. In such embodiments, the combination of data may be used to guide a treatment in real time.

Optionally, anatomical images are acquired to contain multiple frames during a dynamic cycle, for example, during the cardiac cycle. Optionally, additional synchronization data is collected for correlation with the dynamic cycle, for example, an electrocardiogram (ECG).

Optionally, synchronization data collected for correlation with the dynamic cycle is used to better match intensity readings of the functional data to tissue structures (e.g., to the heart wall). Optionally, the image mask method of FIG. 2B may be used with the synchronization data. Optionally, in the case of a single anatomical image (obtained at some point during the cycle) the model allows migration of the detected intensity points to the relevant tissue points (e.g., nearby heart wall). For example, the heart wall moves during the cardiac cycle. Functional data may appear within the heart chamber, even though the intensity is actually related to GPs in the nearby wall. For example, sestamibi data may be migrated mIBG data that is co-registered with the sestamibi data may be migrated. The migrate may provide for both data registration and image construction.

Optionally, at 208, functional data is collected from the patient by a functional imaging modality, for example, functional imaging modality 508.

The anatomical imaging (block 206) and functional imaging (block 208) may occur at different times or may be performed simultaneously at the same time.

Optionally, functional and/or anatomical images are acquired to contain multiple frames during a dynamic cycle, for example, during the cardiac cycle. Optionally, additional synchronization data is collected for correlation with the dynamic cycle, for example, an electrocardiogram (ECG).

A patient may be injected with an imaging agent, for example a radioactive tracer and/or a combination of radio tracers, such as a radio labeled metaiodobenzylguanidine (mIB G) and/or a combination thereof with one or more other radioactive tracers, such as TC and mIBG and TL and mIBG For example, a cocktail for simultaneous isotope acquisition with I-123 mIBG, I-124 mIBG, and/or Tc-99m Technetium (99mTc) sestamibi (Mibi) tracers. The imaging agent may be engulfed to be taken by a specific target pathologic tissue, for example cancerous cells. Combination of the mIBG with other radioactive tracers may give a localizing or monitoring or imaging information.

A functional modality (e.g., SPECT) having one or more radiation detectors may be used to acquire functional data (e.g., SPECT data), for example a SPECT image, of the intrabody volume. The imaging agent may allow localization of specific sites according to imaged uptake rates. For example, mIBG has an affinity for adrenergic nerves, for example to GPs, see Shankar Vallabhajosula et al., PhD, Radioiodinated Metaiodobenzylguanidine (MIBG): Radiochemistry, Biology, and Pharmacology, Semin Nucl Med 41:324-333, which is incorporated herein by reference.

Optionally, functional data such as SPECT data of the intrabody volume may be acquired using a SPECT modality. The SPECT data may be taken using an exemplary SPECT modality that includes a set of collimators, for example scale division (SD) collimators. Optionally, between 10 and 20 collimators are used, for example 14. Optionally, the SPECT modality scan pattern includes about 360 positions around 360 degrees. Optionally, the used reconstruction algorithm is ordered-subsets expectation maximization (OSEM) and/or depth-dependent resolution recovery (RR). Optionally, the pixel size is between about 2.5 millimeter$^3$ and about 4.9 mm$^3$.

In some embodiments, the functional or anatomical data or image is captured before an invasive medical procedure begins, for example before the patient enters a catheterization laboratory (CathLab) room. For example, aSPECT data or image is introduced to a workstation before the catheterization process.

The functional data and the anatomical data may be acquired during a medical procedure, for example a diagnosis or a treatment procedure, for instance a catheterization process, for example as described here.

Optionally, the functional data provides indicators of one or more of the individual tracer uptake, total tracer uptake, tracer uptake rate, blood flow, fractional flow reserve in a blood vessel, tracer washout, areas which are above a predefined threshold (e.g., static and/or dynamic threshold) such as above surrounding average values, and/or the like. Optionally, the functional data is produced per segment of a few centimeters in dimension.

Optionally, functional data is reconstructed with a certain resolution along the wall, for example, along the inner surface of the chamber. Alternatively or additionally, functional data is reconstructed with a certain resolution along the thickness of the wall. The two resolutions may be similar or different.

Optionally, the functional data is reconstructed at a quality resolution of about 1 cm×1 cm×1 cm or better, for example 7 mm×7 mm×7 mm or better, 5 mm×5 mm×5 mm or better. Optionally, the functional data is reconstructed in a non-cubical voxels structures. Optionally, the functional data is reconstructed in voxels which are aligned with a model of the imaged object (such as the heart's muscle wall geometry), and/or a combination thereof.

Optionally, one or more ROIs are identified in the functional data, for example based on the implied and/or indicated mIBG uptake, a size and/or shape of segments in the functional data, for example based on a match with one or more reference items, for example predefined models of the respective ROI(s) and/or by filtration of known organ(s), such as the ventricle. Additional details of identifying ROIs are described herein, for example, with reference to FIG. 2B. Optionally, one or more ROIs are identified by the anatomical image, e.g., by defining one or more image masks.

Optionally, the uptake rate of the radiotracer (e.g., mIBG) is measured and analyzed with reference to the respective ROI in which a GP is located, for example based on anatomical imaging data, for example as described below. When the ROI is indicative of a location that includes ganglia, the uptake is optionally used as an indication about the physiological condition of the ganglia.

In some embodiments, anatomical segmentation of ROIs in areas of the atria may allow separately analyzing different atrial uptake activities, differentiating between uptake activities of different ROIs in the atria, and not only the uptake activity of the atria as a whole. For example, anatomical input from an anatomical imaging source may be used to associate different segments of a SPECT image with different organs or tissues, for example, one segment of the SPECT image may be associated with the atrial muscle wall (e.g., myometrium), and another segment of the SPECT image may be associated with the atrial epicardium. According to some embodiments of the present invention, the ROI(s) includes one or more ganglia. Optionally, a dynamic behavior of the imaging agents during a monitoring period in the ROIs is analyzed to identify differentiator(s) for separating a target location from surrounding tissues. The dynamic behavior is optionally matched with one or more predefined patterns and/or set of rules to identify a target site for treatment, for example for ablation.

Optionally, at 210, the anatomical data and the functional data may be combined to allow locating or detecting the nervous tissue, for example, by a combination module 502A. Detection of GP is optional. Optionally, GPs are not looked for when imaging the nervous system and/or other structures. For example, anatomical data and the functional data may be combined to obtain a combined anatomical-functional image, e.g., the image may contain two layers—anatomical and functional. The image may be of the entire organ or a part thereof. The combined anatomical-functional image or data may be presented to the operator, e.g., by output element 516. The combined anatomical-functional image or data may be sent to processor 504 for further processing—e.g., to identify one or more ANS components thereof.

Optionally, at 212 ganglions are located, for example, by a locating module 502C. Possible locations may be identified. Functional behavior of ganglions may be extracted. Optionally, an ANS map and/or image of the target organ is generated. The ANS map may include the locations and optionally size and activity levels of one or more ANS components. The identified nervous tissue may be presented on an anatomical image to show possible locations, as the actual location of the GP may be uncertain, instead showing several alternatives and/or a density map. For example, colored on a black and white image. Co-ordinates may be provided with reference to a navigation tool (e.g., catheter). Optionally, selected parts of the nervous tissue are identified and/or located, for example, based on a local size above a predefined threshold, based on local functional activity, and/or other predefined rules. In some embodiments, an image per se is not generated but rather ANS data of the identified nervous tissue may be generated—e.g., file contain identified nervous tissue information such as: location, size and/or activity level.

The number of GPs identified, is for example, 1, 2, 3, 5, 8, 10, or other intermediate or larger numbers, or, 2-6, or 3-8, or 4-10, or other ranges. The size of GPs identified is, for example, about 2 mm×2 mm×2 mm to about 4 mm×4 mm×4 mm, or about 1 mm×1 mm×1 mm to about 3 mm×3 mm×3 mm, or other smaller, intermediate or larger sizes.

The ANS image or data may be of the entire organ or a part thereof. The ANS image or data may be presented (or otherwise provided) to the operator, e.g., by output element 516. The ANS image or data may be sent to navigation system 514 and/or stored on memory 506 for future use.

According to some embodiments of the present invention, functional data may be combined with anatomical data for localizing ganglionic plexi (GPs), for example: in the atria. This may allow guiding a medical procedure, for example to use anatomy to tell where the catheter is located, and use the functional data to identify targets. For example, the localization may allow guiding an operator to operate an ablation unit located at the tip of a catheter.

Figure 2B:
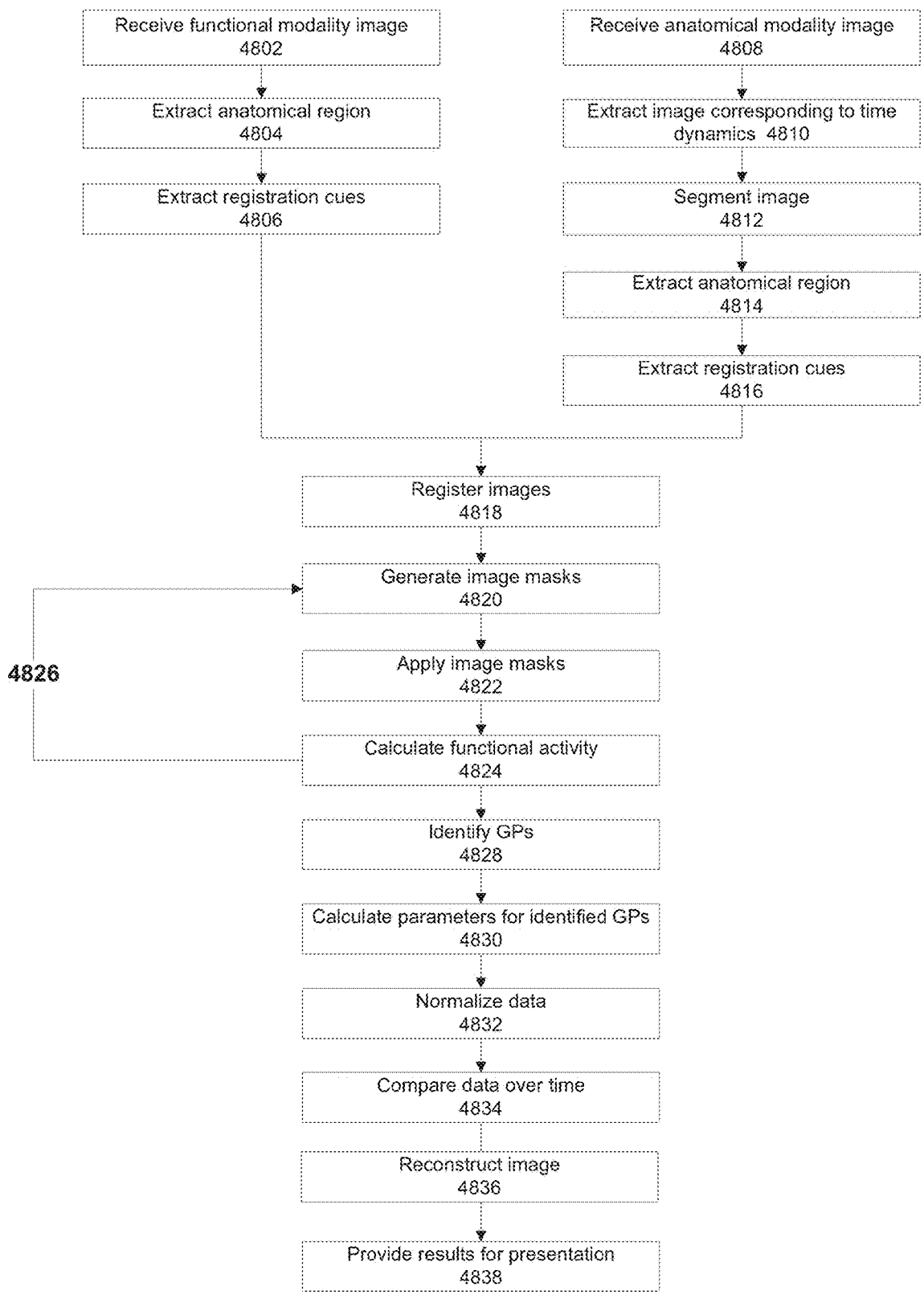

Reference is now made to FIG. 2B which is a flow chart of a method for processing functional images to identify and/or locate one or more ANS components (e.g., ganglions) (may correspond to block 212), in accordance with some embodiments of the present invention. It should be noted that method of FIG. 2B is not limited to identification and/or localization of ANS component(s), for example: it may be used for extracting other information from functional and anatomical images or data based on application of image masks, for example, as will be discussed below.

Optionally, the method may combine the functional and anatomical images (may correspond to block 210). Alternatively, the anatomical image may provide a basis for reconstructing selected parts of the functional image that contain the GPs. The method may be performed, for example, by data combining module 502A and/or processor 504 of FIG. 3, an image data processing unit, or other modules and/or systems. The method may use images from the anatomical imaging modality (which show organ structure, but not GPs in sufficient detail or at all) to reconstruct images from the functional imaging modality (which may show ANS components—e.g., GPs or activity level, but not the organ structure in sufficient detail or at all). Reconstructed functional images may show the GPs overlaid on the organ structure.

Optionally, the method provides (as an output) the general region where GPs are located. Alternatively or additionally, the method provides regions where the GPs are not located. The precise location of GPs may vary anatomically between different patients. The specific location of the GP may be identified during an ablation procedure, for example, using high frequency stimulation (HFS). Alternatively or additionally, the method provides the precise location of the GP, for example, using a coordinate system. In some embodiments, there may be a minor deviation from the GP actual location (e.g., due to noise in image, registration) to the location of the GP which provided by the method which may be corrected by the operator during the ablation procedure.

Optionally, the functional activity (e.g., mIBG activity) is identified in preselected tissue regions. The image masks are defined based on the preselected tissue regions within the anatomical image that correspond to the functional activity that is being detected. For example, in the heart, GPs are located within the heart wall or nearby, and/or in fat pads. Optionally, the fat pad size and/or shape is used to define the search window and/or image mask. Distribution of mIBG within a fat pad may be of interest, with or without GP detection. Image masks are defined for the anatomical image to look for the GPs within the heart wall or nearby. The generated image masks are then applied to the functional data, to identify the GPs based on activity within the mask—e.g., within the heart wall or nearby.

Optionally, the reconstruction is directed to anatomical regions where functional activity (e.g., from GPs) is expected, for example, based on a predefined anatomical atlas, for example, based on the location of GPs in normal anatomies. Such data may be collected from several patients, for example, by imaging and/or autopsy dissection.

Optionally, the image masks are defined to identify some or all activity of nerves, for example, GPs, synapses, axons, nerve bodies, or other nerve structures and/or different types of nerves. Image masks may be different and/or the same.

In this manner, the image masks may serve a guide for directing the identification of the nerve structures to certain regions within the functional image and/or data. There may be many regions of intensity within the functional data, only a small subset of which may be relevant for identifying ANS components location—for example: to be used in ablation. As the rough location of the nerve structures relative to body organs and/or tissues may be known (e.g., by the atlas) but not visualized on the anatomical image, the search for the nerve structures may be directed to the corresponding regions on the functional image. The search may be focused to regions having a large percentage of intensity readings that denote relevant nerve structures. The method may be used to detect different types of GPs, at different locations of the body (tissues, organs), for example, as described herein.

The method may improve system performance, by performing calculations within the region of interest to identify the neural tissue. Calculations may not need to be performed in regions without neural tissue.

The method may reduce radiation exposure to the patient. Additional radiation may be applied to regions containing the neural tissue for imaging to provide higher resolution at the regions. Less radiation may be applied to regions not containing the neural tissue.

The method may improve analysis results and/or images. Neural tissue within selected regions may be analyzed and/or imaged. Neural tissue outside the selected regions may not be analyzed and/or imaged. Interference and/or image complexity from the neural tissue outside the selected regions may be reduced or prevented. In this manner, neural tissue that is not contributing to the medical condition of the patient and/or neural tissue that is not a target for ablation therapy may be excluded from further analysis. Alternatively, the non-targeted neural tissue may be identified separately from neural tissue targeted for ablation.

Optionally, at 4802, functional imaging modality data and/or images are received, for example, a D-SPECT image or other images. The images may be of a body part, for example, a torso, an abdomen, a heart, or other body parts (e.g., based on scanning protocols). The body part includes the nerve tissue to be images and/or the innervated organ, for example, GPs of the heart, intestines or other organs. Optionally, the functional images includes regions of activity that denote nerve tissue (e.g., GP), for example, from uptake of the radiotracer (e.g., mIBG).

Optionally, functional data is collected from a body part that has regions where nerve activity is expected, and regions where nerve activity is not expected. For example, during imaging of the heart, data denoting nerve activity is expected from the heart wall and/or surrounding tissues, and no nerve activity is expected from inside the hollow chambers (containing blood). Noise may be received from areas corresponding to the inside of the heart chamber, even though no activity is expected. Optionally, the noise is removed from the functional data based on the corresponding anatomical image (e.g., after image registration). Optionally, intensity denoting noise within blood (or other fluid) filled chambers and/or vessels is removed. For example, intensity readings of the functional data corresponding to heart chambers and/or surrounding blood vessels are removed, e.g., by applying one or more image mask on functional image.

Optionally, at 4804, an anatomical region is extracted from the image. Optionally, the tissue (which may contain nerve structures) is separated from hollow spaces (which do not contain nerve structures, but may contain fluid). For example, to image the heart, the wall of the left ventricle (LV) may be extracted. Alternatively or additionally, the hollow space within the LV may be extracted. It is noted that the extracted region may be a layer of tissue, such as the tissue layers forming the LV wall, instead of, for example, the LV including the hollow chamber inside the LV. For example to image the kidney, the walls of the renal artery may be extracted and/or the inside of the artery may be extracted. When imaging other organs, dominant portions of the organ may be selected.

Optionally, at 4806, one or more registration cues are extracted from the image. The registration cues may be from the organ of interest, and/or surrounding anatomical structures, for example, LV axis, liver, heart septum, RV, torso. Registration cues may be used to match anatomical images with functional images, and/or to match anatomical images during a physiological cycle (e.g., cardiac cycle).

Optionally, at 4808, anatomical image modality data and/or images are received, for example, from a CT, MRI, 3D US, 2D US, or other modalities. The anatomical image denotes the structure of the tissue and/or organ innervated by the nerve tissue (e.g., GP). The anatomical image denotes the tissue and/or organ structure corresponding to the location of the nerve tissue (e.g., GP). The anatomical images may contain the same nerve tissue to be imaged and/or the same innervated organ.

Alternatively, anatomical data is received that is not personalized to the patient, for example, from a general anatomical model.

Optionally, anatomical data from an anatomical imaging modality is received to reconstruct an anatomical image of a region of a body of a patient. Optionally, the region comprises a portion of at least one internal body part which borders on a target nerve tissue.

The anatomical images and the functional images denote corresponding regions of the body containing the GPs for identification and/or localization. For example, both modalities may take pictures of the heart, kidney, or other organs.

For example, to image GPs of the heart, anatomical and/or functional images of the heart are obtained. For example to image GPs of the kidney, anatomical and/or functional images of the kidney, renal artery and/or aorta are obtained.

Optionally, at 4810, images corresponding to different times during a dynamic cycle are extracted and/or acquired. For example, for the heart, images are extracted along the cardiac cycle, for example, the end diastolic volume (EDV) and/or the end systolic volume (ESV). In another example, for the bladder, images may be extracted for a full bladder and an emptying bladder.

The average image may be computed, for example, (EDV+ESV)/2.

Optionally, at 4812, one or more images are segmented. Segmentation may be fully automatic and/or may require manual user intervention.

Optionally, at 4814, an anatomical region is extracted. Optionally, the anatomical region corresponds to the anatomical region extracted at 4804. Optionally, the anatomical region is extracted from the segmented image of block 4812.

Optionally, at 4816, one or more registration cues are extracted from the image. The registration cues may be from the organ of interest, and/or surrounding anatomical structures, for example, LV axis, liver, heart septum, RV, torso.

Optionally, at 4818, the functional images or data and the anatomical images or data are registered. Optionally, the images are registered based on alignment of the extracted anatomical regions of blocks 4804 and 4814. Registration may be performed manually, automatically and/or semi-automatically.

Optionally, the registration is performed to take into account the dynamics of the organ, for example, movement of the heart. For example, anatomical images during the dynamic cycle may be aligned together, and/or functional data may be corrected for the dynamic movement, for example, intensity readings within the heart chamber may be corrected to the nearby moving heart wall.

Optionally, at 4820, image masks are generated based on the anatomical image and/or data. Optionally, the image masks direct processing and/or visual display of the nerve tissue to specific locations of the image located within the image masks. For example, GPs are displayed and/or processed within the volume of an applied image mask. GPs outside the volume of the image mask may not be processed and/or displayed. GPs outside the volume of the image mask may be processed and/or displayed differently than those GPs inside the image mask.

Optionally, the anatomical images are processed to generate the image mask corresponding to dimensions of at least one internal body part, for example, the walls of the chambers of the heart. For example, dimension of internal body part of the specific patient may be calculated and used to define the mask.

Optionally, the image masks are selected and/or defined for tissue surrounding a hollow chamber, for example, the image masks are defined based on the shape of the heart chamber walls and do not include the hollow region within the chambers, the image masks are based on the shape of the arterial wall and do not include the hollow region within the artery, the image masks are based on the shape of the bladder wall and do not include the hollow region within the bladder. It is noted that the nerve structures may exist within the tissues defined by the image masks, but may not exist within the hollow spaces (which may be filled with fluid such as blood, urine or other fluids). The image masks may include tissue surrounding the organ of interest.

The image masks are defined, for example, based on image segmentation (e.g., according to the ability of the system to segment the image), based on tissue types (e.g., muscle vs. connective tissue), based on organ size, based on sub-structures within the organ (e.g., heart chambers, liver lobes, kidney parts), or other methods.

Different image masks may be generated for different tissue types, and/or for GPs at different locations within the organ. For example, for GPs within the epicardium one set of image masks is generated. For GPs within the myocardium another set of image masks may be generated. Image masks may be generated for fat pads.

The image mask may be a 2D and/or 3D volume with a shape and/or size selected based on tissues and/or organ parts within the anatomical image. The image mask may correspond to anatomical parts believed to contain the neural tissue for imaging (e.g., GPs), for example, corresponding to the walls of the four heart chambers, corresponding to the intestinal wall, bladder wall, renal artery, aortic branch region of the renal artery, kidney, or other structures. In some examples, the image mask may be generated to contain GPs within the epicardial and/or myocardial tissue of the heart. In another example, the image masks may be generated to contain kidney innervating GPs at the aorta-renal artery junction. It is noted that the image masks may be generated based on an estimated location of the GPs (e.g., normal patient anatomy), as the GPs may not be visible on the anatomical image. The image masks may be generated based on an estimated location of the GPs and based on dimension of internal body part as may be inferred from the anatomical image.

Optionally, the generated image masks correspond to the segments of the anatomical image. For example, the heart is segmented into some chamber walls (e.g., having the GPs for ablation), and the generated image masks correspond to the chamber walls of interest.

For example, a first image mask is generated for the walls of each chamber of the heart. It is noted that the thickness of smaller chambers may be difficult to measure in certain images (e.g., CT). In such cases, the thickness of the first image masks for each chamber may be based on a measurable anatomical region such as the LV. Alternatively, the thickness of the chamber is measured using another imaging modality (e.g., US, MRI) and/or estimated. The measurement may be performed using the anatomical image, for example, the thickness for the image mask may be based on the thickness of the LV as measured on the CT image. Exemplary image mask thicknesses for the chambers may then be estimated based on the LV measurement, for example: 0.3 to 0.5×LV thickness for the image masks of the LV, right ventricle (RV), right atrium (RA) and left atrium (LA). Or, for example, the multiplication factor may be, 0.3, 0.7, 1.2, 1.5, 2.0, or other smaller, intermediate or larger values. The zone for searching for GPs may be a function of LV thickness away from the wall, and/or in mm.

Different walls make have different masks. The image mask may be positioned contain the GPs and/or surrounding tissue. The image mask may be centered on the wall, or may be positioned towards one end of the wall. For example, to search for epicardial GPs, the mask may be at the outer edge of the wall. TO search for myocardial GPs, the mask may be at the middle.

Optionally, the image masks are generated and/or applied based on templates. The templates may define: the location of the innervated organ (or tissue) and/or the location of the GPs within and/or in proximity to the innervated organ, outside of the organ. The templates may be generated, for example based on a predefined anatomical atlas that maps nerve structures to tissues and/or organs of the body.

Optionally, the generated image masks are adjacent to one another. Alternatively or additionally, the generated image masks overlap with each other. Alternatively or additionally the generated image masks are spaced apart with respect to one another. The template may define the location of the GPs at a distance of greater than about 1 mm, or about 2 mm, or about 3 mm, or more from the heart wall.

Optionally, the generated image masks are adjacent to one another. For example, to cover a large area in searching for GPs. Alternatively or additionally, the generated image masks overlap with each other, for example, to improve matching of GPs to tissue type, and/or when identifying GPs in a moving organ such as the heart. Alternatively or additionally the generated image masks are spaced apart with respect to one another. For example, when searching for GPs in different areas, for example, to prevent false identifications between the areas.

Optionally, at 4822, the image masks are applied to the functional image. Alternatively or additionally, the image masks are applied to the functional data. Alternatively or additionally, the image masks are applied to combined functional and anatomical images and/or data, for example, overlaid images.

Optionally, the image masks are applied based on the registration process (block 4818). The anatomical information serves as a guide, using the selected image masks, for selective reconstruction of GP related data within the functional image. The image masks may be correlated with the image to contain anatomical structures having the neural tissues. The application may be based on the image registration, for example, applied based on a common coordinate system. The image masks may be applied to a certain type of tissue containing neural tissue. For example, the image masks may be applied to the epicardium of the heart. The image mask may be applied to have its inner surface aligned with the epicardial surface of the chamber wall, such that the image mask contains the epicardial space encompassing the chamber.

Optionally, the generated image mask is correlated with the functional data for guiding the reconstruction of a functional image depicting the target nerve tissue.

Optionally, at 4824, functional activity is calculated within the applied image mask space. Optionally, the average functional activity is calculated. Optionally, the standard deviation of the functional activity is calculated. For the heart example, the functional activity is calculated around each chamber separately, and around the entire heart. Average activity for the chambers may be denoted by A1LV, A1RV, A1LA, A1RA. Average activity for the heart may be denoted by A1H. Standard deviation of the activity may be denoted by SD1LV, SD1RV, SD1LA, SD1RA, SD1H. Optionally, average activity and/or standard deviation may be calculated for the entire functional image or data. Optionally, average activity and/or standard deviation may be pre-set, e.g., based on previous imaging of the same patient, based on "normal" patient activity etc.

Optionally, at 4826, one or more of 4820, 4822 and/or 4824 are repeated. Alternatively, one or more of 4820, 4822, 4824, 4828, 4830, 4832, 4834, 4836 and/or 4838 are repeated. Alternatively, one or more of all blocks in FIG. 2B are repeated. Optionally, additional image masks are generated for different anatomical parts (e.g., for different heart chambers, for different tissue layers), optionally for different tissues types containing neural tissue. Optionally, additional image masks are generated for anatomical tissues and/or anatomical parts that are nearby and/or adjacent to the earlier analyzed anatomical parts. Different image masks may be generated, and then applied together to identify the GPs innervating the organ. For example, different types of GPs may innervate different tissues. Alternatively, different image masks are processed separately, for example, to differentiate between different GPs (e.g., located within different tissues of the organ).

Alternatively or additionally, image masks are generated for different time frames, optionally on each image of the dynamic cycle (e.g., cardiac cycle). The mask may be dynamic. The mask may change over time after temporal registration. Optionally, the mask is a spatiotemporal mask. The dynamic image masks may correlate with the anatomical regions of interest during the cycle. For example, the image masks may move with the heart during the cardiac cycle, but maintaining the same relative position. For example, image masks applied to the LV wall move back and forth (and/or become smaller and larger) as the heart contracts and relaxes, but maintain the relative position against the LV wall.

Alternatively or additionally, image masks are generated for both the anatomical and the functional images. For example, image masks are generated based on the combined and/or registered images, which may form a single image, or two separate (optionally linked images).

Optionally, the anatomical images are obtained during a cyclic physiological process (e.g., cardiac cycle, bladder emptying, intestinal peristalsis). Optionally, different spatiotemporal image masks are selected for different images obtained during the physiological process. Optionally, the different spatiotemporal image masks are synchronized with the physiological process to correspond to the same location of the tissues. In this manner, the location of the tissues may be maintained as the tissues move during the physiological process.

For example, at 4820 (repeated) additional image masks are generated to detect neural tissue within the myocardium. The size and/or shape of the myocardial masks may be different than the size and/or shape of the epicardial masks and may correspond to different regions within the heart. For example, epicardial image masks may be aligned with the epicardial surface of the chamber wall, such that it will contain the epicadial space encompassing the chamber. The myocardial image masks may encompass the walls of each chamber.

Exemplary myocardial image mask thicknesses include: 1.2×LV thickness for the image masks of the LV, 0.7×LV thickness for the RV, 0.4×LV thickness for the RA, 0.4×LV thickness for the LA, or other multiplication factors (for each thickness) for example, 0.4, 0.7, 1.0, 1.2, 1.5, or other smaller, intermediate or larger values.

In another example, neural structures are identified within the septum. Image masks may be created for the septum.

For example, at 4822 (repeated) the image masks are applied to the image to correlate and/or contain myocardium.

For example, at 4824 (repeated) the average and/or standard deviation of the functional activity may be calculated for the myocardium image masks. Average activity for the chambers may be denoted by A2LV, A2RV, A2LA, A2RA. Average activity for the heart may be denoted by A2H. Standard deviation of the activity may be denoted by SD2LV, SD2RV, SD2LA, SD2RA, SD2H.

Optionally, the calculated activity levels are normalized, for example, to a point or volume in the body, to a point or volume within the image mask space, or other methods. The normalization may allow for identification of the GPs for example, within the mediastinum.

Optionally, at 4828, GPs are identified within the applied image mask space. It should be noted that 'GP' term is used for ease of discussion and that the method may be applied for identifying ANS component(s) or for extracting or identifying other information relating to neural activities, or other tissues. Alternatively or additionally, GPs are identified within the organ volume and/or nearby tissues. Optionally, GPs identified within multiple different image masks that are combined into a single image of all the identified GPs, for example, the identified GPs within the organ. Alternatively or additionally, GPs identified within corresponding image masks of multiple frames (e.g., all image masks of the LV myocardium during the cardiac cycle) over time are combined.

Optionally, the GPs are identified by adjusting the position and/or size and/or shape of the image mask. Optionally, the image mask is adjusted based on the corresponding anatomical image. Optionally, the image mask is adjusted to exclude regions that may not physically contain GPs. Optionally, the functional data is adjusted instead of, and/or in addition to, and/or based on the adjusted image mask. For example, functional intensity data obtained from anatomical regions which may not include nerve structures, for example, inside the hollow (e.g., fluid filled) space, such as heart chambers and/or blood vessels. The chamber itself may not contain nerves. When intensity readings are detected in the chamber (e.g., next to the heart wall), the image data and/or image mask may be adjusted to reflect the estimated position of the intensity readings. Mask adjustment may be required, for example, when registration between anatomical image data and functional image data is imprecise and/or incomplete. For example, the anatomical image data and functional image data were obtained at different angles.

Optionally, the GPs within the image mask and/or organ volume are located. The relative position of one GP to another may be calculated, for example, in 2D and/or 3D.

Optionally, the GPs are combined together into an ANS map or ANS data. Optionally, connectivity between GPs is determined Connected GPs may be within the same image mask, within different images masks at different spatial locations, and/or within different image masks at different points in time (but at the same corresponding location). Optionally, the spatial relation between GPs is determined. For example, the relative location between a first GP with respect to the location of a second GP.

Optionally, areas of extreme activity are identified. For example, epicardial GPs (EGP) and/or myocardial GPs (MGP) are identified based on extreme mIBG activity.

Optionally, GPs are identified based on one or more predefined thresholds and/or rules. Optionally, GPs are identified based on size. Alternatively or additionally, GPs are identified based on activity level in reference to average activity and/or surrounding activity. Alternatively or additionally, GPs are identified based on connectivity between GPs.

Optionally, the GP may be identified as an object with a size of at least about 4×4×4 millimeters (mm) (e.g., for an EGP), or about 2×2×2 mm (e.g., for an MGP). Alternatively or additionally, the GP may be identified by comparing calculated activity (e.g., image intensity) of a certain region to surrounding activity in the same image mask. Alternatively or additionally, the GP may be identified by comparing calculated activity (e.g., image intensity) within the image mask to activity in another image mask. For example, the EGP may be identified as satisfying the rule that the total activity of the EGP is a predefined factor times the standard deviation (SD1 and/or SD2), above average activity (A1 and/or A2), and/or the adjacent activity surrounding it is lower than half of the EGP activity (e.g., correlated for volume). Optionally, the user may select and/or modify the predefined factor. For example, the MGP may be identified as satisfying the rule that the total activity of the MGP is another predefined factor times the standard deviation (SD1 and/or SD2), above average activity (A1 and/or A2), and/or the adjacent activity surrounding it is lower than half of the MGP activity (e.g., correlated for volume). Optionally, the user may select and/or modify the predefined factor.

Optionally, identification of GPs is performed per frame, optionally per frame of the dynamic cycle (e.g., cardiac cycle).

Optionally, the identified GP is automatically related to a tissue type. Optionally, the identified GP is related to the tissue type based on the applied image mask. Alternatively or additionally, the identified GP is related to the tissue type based on the characteristics of the intensity readings, for example, large sizes (denoting large GPs) may only be found in certain tissues. Optionally, different types of GPs are related to different tissues. For example, myocardial GPs are related to the myocardium and/or epicardial GPs are related to the epicardium.

Optionally, at 4830, one or more parameters are calculated for the identified GPs (also referred to herein as GP parameters). Examples of parameters include: average size, specific activity (e.g., counts per voxel of GP/average counts in the corresponding image mask volume), power spectra (e.g., power below 1 Hz, power between 1-5 Hz, ratio of high to low frequencies), normalized power spectra, GP connectivity map (e.g., connectivity and interaction between different GPs), number of GPs per predefined area (e.g., GP density number/square centimeter).

For example, for identified EGP, one or more of following parameters may be calculated: EGP size, EGP specific activity, EPG power spectra graph, EGP normalized power spectra (i.e., the difference between the EGP power at different frequencies minus the power of the total counts from the myocardial image mask space), EGP connectivity map.

For example, for identified MGP, one or more of the following parameters may be calculated: MGP number in an area and average size for each predefined area (Marshal ligament, left inferior LA wall, right inferior LA wall, other areas), MGP specific activity, MGP power spectra, MGP normalized power spectra (i.e., the difference between the MGP power at different frequencies minus the power of the total counts from the myocardial image mask space).

Optionally, calculation of GP parameters is performed per frame, optionally per frame of the dynamic cycle (e.g., cardiac cycle).

Optionally, at 4832, the calculated and/or other parameters may be normalized. Normalization may take place at one or more blocks of the method, for example, during and/or after acquiring the functional and/or anatomical images, upon calculation of functional activity, upon identification of GPs, upon calculating parameters for the GP, upon comparison of data over time, or at other blocks.

Examples of one or more normalization techniques include: raw data, raw data divided by the raw data value in a known fixed anatomical location acquired at roughly the same time (for example, the activity of the tracer in the patient's mediastinum), normalization to a normal patient data set, normalization to a value of the activity at the first or the last image acquisition from a sequence of acquisitions, normalization to value acquired at different physiological state (e.g., rest, stress), a combination of some or all of the above, and/or other methods.

Alternatively, the normalization of 4832 is performed instead of and/or in addition to, before a different block in the process, for example, before GPs are identified in block 4828. The normalization may help in identifying the GPs. For example, activity level (e.g., mIBG level) at a local region is compared to an average value and/or standard deviation across the organ volume, within the image mask space and/or relative to a predefined threshold.

Alternatively or additionally, the calculated data (e.g., blocks 4824, 4828, 4830) and/or measured functional intensity are corrected for sensitivity. Optionally, sensitivity correction is performed within each image mask and/or in related image masks. For example, some areas may have relatively higher sensitivity to uptake of the radioagent, and some may have relatively lower sensitivity to the uptake of the radioagent. Optionally, the anatomical data is correlated to the sensitivity. Optionally, the image masks are generated (block 4820) based on different sensitivity levels, for example, one set of image masks for higher sensitivity nerve structures, and another set of image masks for lower sensitivity nerve structures. Optionally, the different sensitivities are normalized to a common baseline.

Alternatively or additionally, measurements of the functional data are normalized, for example, measurements of uptake of the radioagent are normalized to the level of corresponding chemical in the patient. Optionally, intensity measurements are normalized according to the level of activity of GP being identified. Optionally, measurements denoting activity of the GPs are taken. For example, in the case of mIBG, measurements may be normalized to the level of norepinephrine (NE) (and/or adrenaline and/or epinephrine) in the patient. For example, the level of NE is measured in the blood (e.g., by blood sample), urine, or other body fluids. The intensity of mIBG uptaken is normalized based on the measured NE. Additionally or alternatively, mIBG measurements may be normalized to a decay function of mIBG over time (e.g., from the injection of the mIBG). In another example, the level of activity is measured by non-chemical methods. For example, normalization of mIBG is performed based on measurements taken during a cardiac stress test (e.g., based on ECG measurements, heart rate, cardiac output, or other measurements). The measurements may be correlated with levels of activity of the GPs being identified (e.g., by a table, mathematical equation, or other methods).

Optionally, at 4834, data is compared over time. Optionally, changes in GP parameters over time are identified. Optionally, dynamic changes of the calculated parameters between different acquisition times are determined. For example, the changes in GP (e.g., EGP) activity over time may be calculated, from injection till 6 hours post injection, by repeating the image acquisition several times during this time window. The functional images may be acquired at more than one time after the tracer injection. Optionally, at 4836, a functional image is reconstructed based on the mask applied to the functional data and/or image. Alternatively or additionally, an image is reconstructed based on the mask applied to the combined functional and anatomical data and/or images. The reconstructed image may contain the identified GPs, for example, as regions of increased intensity. The reconstructed image may be overlaid on the anatomical image, illustrating the physical location of the GPs.

Alternatively or additionally, the characteristics of the GPs within the functional image are reconstructed. The reconstruction is instructed by the image mask.

Optionally, at 4838, the calculated results (e.g., block 4828, 4830, 4832, 4834) and/or reconstructed images (block 4836) are provided for presentation or otherwise provided to the operator. For example, presented on a monitor to a physician. Additionally or alternatively, the calculated results and/or reconstructed images may be stored in a memory for future use (e.g., diagnosis). The calculated results may help in diagnosing the patient (e.g., as described with reference to block 216) and/or in guiding treatment (e.g., as described with reference to block 228).

Optionally, the results are provided for presentation on a certain frame, for example, the end systolic frame. Alternatively, results are provided for presentation on multiple frames, for example, a video of the cardiac cycle.

Optionally, the reconstructed functional image or combined functional and anatomical image is provided for registration during a treatment procedure. The reconstructed functional image may be overlaid on and/or registered with anatomical images obtained during the treatment procedure. The overlaid and/or registered images may be used by the operator to physically determine locations of the GPs during the treatment.

The method of FIG. 2B has been described with reference to the heart. The method is not limited to the heart, and may be used for other organs, hollow fluid filled organs (e.g., stomach, aorta, bladder) and/or solid organs (e.g., kidney, liver). GPs and/or nerve endings may be identified in the other organs. For example, the aorta may be segmented based on surrounding structure (bones, muscles, branching arteries) and image masks generated accordingly. For example, the liver may be segmented based on anatomical liver lobe divisions.

Referring now back to FIG. 2A, alternatively or additionally, the ganglions are located according to one or more mapping functions which map a reference kinetic behavior and/or an uptake rate for one or more regions of the imaged intrabody volume.

For example, the registration may be performed by a correlation matrix which may be calculated in advance to the specific intrabody volume imaged in the functional data and the anatomical data. In some embodiments, the nervous tissue may be located by identifying one or more unique properties of uptake and/or kinetic information and/or relationship to an uptake and/or kinetic information of surrounding tissues and/or organs. For example, a layered image is formed where functional data is added as an additional layer on top of an anatomical image, such as a fluoroscopy image, optionally forming the ANS map. The combination may be performed by presenting the functional data side-by-side with, registered with and/or overlaid on the anatomical data.

It should be noted that combining the anatomical data and the functional data may increase the SNR of the functional data. Registering the functional data and the anatomical data (e.g., to a single coordinate system) may indicate an anatomical region in which different uptake indications may be shown. This may allow filtering the functional data according to an estimated volume in the anatomical data in which a target nervous tissue is located (for example, by using image masks as discussed with reference to FIG. 2B).

Optionally, the localization and/or imaging and/or identification may begin before and/or simultaneously with the injection of the imaging agent. In another example, the imaging starts immediately after the injection of the imaging agent. In an example, the imaging starts after the injection at a delay of about up to 5 minutes, about 10 minutes, about 30 minutes, about 1 hour, between about 1 and about 10 minutes, between about 5 and about 20 minutes, between about 10 and about 30 minutes, between about 15 and about 60 minutes, between about 30 and about 120 minutes, between about 1 and about 6 hours, or between about 5 and about 48 hours.

Optionally, more than 2 imaging steps may be provided for localization. Optionally, the localization includes acquisition of dynamic physiological processes, such as dynamic perfusion, dynamic tracer uptake, dynamic tracer washout, and the like.

Optionally, at 214, an ANS model for ganglion connectivity is generated, for example, by an ANS generation module 502D. The model may be generated based on the identified and/or located ganglions (block 212), for example, based on ANS map or data. Optionally, the ANS model is the ANS map or ANS data. The model may be generated, for example, as described herein. The model may be generated by linking between identified ganglions. Optionally, the model links between spatially located GPs.

Alternatively or additionally, a map is generated.

The map and/or reconstructed images may contain, for example, GPs, nerve ending density in tissue, tissue functionality, tissue anatomy, tissue surrounding the nerves (e.g., fat pads), anatomical data, other data such as electrical activity, MRI based functionality, CT based physical data, and/or other data.

The image may be, for example, 2D, 3D, 3D with anatomical registration landmarks, image patches, nuclear medicine data, and/or other data.

The generated map may be displayed, may be used for navigation for treatment, may be further analyzed, and/or may be transferred (e.g., using physical media and/or downloaded).

Optionally, the ANS model may comprise of one or more reconstructed images (for example as discussed in reference to 4836). In some examples, the reconstructed image is of a certain tissue region, or a volume or a selected region of interest. In some examples, the reconstruction is based on voxels, segments, or model based or a combination thereof. In some examples, the image reconstruction may provide intensity of uptake of the one or more radiotracers, or the kinetic parameters that correspond to the dynamic behavior of the imaging agent in the innervated tissue, nerve tissue and/or in the blood vessels.

Optionally, at 216, a diagnosis is performed and/or assigned to the patient. Optionally, the diagnosis includes the underlying neural anatomical structures believed to be contributing and/or causing the patient's symptoms and/or disease. Alternatively or additionally, contribution by neural tissue to the patient's condition is ruled out, for example, the imaging analysis may indicate normal neural tissue. The diagnosis may be made manually by the physicians and/or automatically by software. For example, software may compare between the generated distribution of the imaged tissue with one or more sets of expected distributions (e.g., of 'normal' patients and/or previous distribution of the same patient). Abnormal activity may be detected based on the comparison.

Optionally, at 218, the generated ANS model (block 214) is stored, for example, on data repository 512. Optionally, the diagnosis (block 216) is stored. Other data may also be stored, for example, the functional and/or anatomical raw images.

Optionally, at 220, therapy is selected for treating the patient. Optionally, the therapy is selected based on the diagnosis (block 216).

Optionally, localization of ANS component(s) based on the combination of the functional data and the anatomical data may be used for selecting and/or guiding a medical treatment (the instrument guidance may be based on the localization), for example a denervation procedure, such as renal denervation or denervation of ganglia in the atria, a muscle ablation procedure (for example of the atrial and/or ventricular walls), innervations modulation procedure, blood treatment and/or stent placement procedure (in a blood vessel), for example as described herein. For example, the localization may be used for guiding an ablation of ganglia in the atria, for example as a procedure of treating atrial fibrillation (AF), for instance during a catheterization procedure, optionally based on a combination of SPECT data and the anatomical data. Optionally, the guided catheter is an intracardiac echocardiography (ICE) catheter. In such embodiments, the imaging data from the ICE catheter may include anatomical data that may be combined with the SPECT data or image and/or reconstructed image.

Optionally, an estimated prediction of success of an ablation procedure is given, for example, based on the measured uptake where for example an estimation of a failure may indicate a recurrence of an arrhythmia and a successful estimation means an arrhythmia reduction and/or elimination. In such embodiments, there may be a value to the location(s) in which uptake rate is measured. For example, the ROI may be in the left ventricular (LV) and/or in the atria. Optionally, ROIs are obtained by using image masks. It should be noted that for mIBG, the overall atria uptake is far less than in the uptake in the LV. For example, GPs in certain locations may denote a relatively high ablation success rate, whereas GPs in other locations may denote a relatively low ablation success rate. Other examples include prediction based on the map of GPs (ANS map), for example, the success rate for ablation of highly interconnected GPs may be lower than ablation of low interconnected GPs. Optionally, an estimation module automatically calculates the estimated prediction of success.

Optionally, at 222, the ANS model and/or map (e.g., surface of data linked to anatomical landmarks, such as 2D and/or 3D) and/or diagnosis is loaded to a catheter navigation system (e.g., navigation system 314). Optionally, the navigation system is a 3D electrophysiological (EP) system. Optionally, the navigation system is designed for GP ablation guidance. Optionally, navigation system 514 is the CARTO® system. Optionally, the coordinates of the GPs and/or maps of inter-GP links are loaded into the CARTO® system for displaying the location of the GPs and/or map relative to the treatment catheter of the CARTO® system.

Optionally, the model is sent to a server to be merged with the navigation system (e.g., CARTO® system). Optionally, billing is performed per use, for example, based on a pay per use model. Alternatively or additionally, the model is loaded to portable media with the data stored on the media (e.g., memory card, CD), for example, the patient is provided with the model on the CD to take to the next provider.

Optionally, billing is automatically performed for the diagnosis and/or therapy, based on the loaded diagnosis and/or planned treatment. For example, the pay per use method, pay per generated map, or other methods.

Optionally, data is decrypted upon loading to the catheter navigation system. The data may be have been encrypted to help ensure patient privacy. The decrypted data may be displayed, for example, as an image.

The functional data may be acquired before the medical procedure is initiated, for example few hours and/or a day before the treatment procedure (e.g., heart treatment procedure). For example, a SPECT data may be registered with an electro-anatomical map, for example using a CartoMerge™ module (e.g., by data combining module 502A). Loading the ANS model to the catheter navigation system may provide an operator with an accurate guidance during a treatment, such as an ablation procedure. The loading to the catheter navigation system may help the operator plan the treatment before inserting the catheter.

Optionally, at 224, the ANS model is marked-up, for example, manually by a user entering data using input element 518 and/or automatically by software. Optionally, the treatment plan is annotated based on the user entered data and/or automatically generated data. The marking-up and/or the annotation may help the operator plan the treatment plan before inserting the catheter.

Optionally, the maps and/or data is simply overlaid on the CARTO® system, and treated as any other overlay by the system. The physician may understand what the overlaid map means.

Optionally, the treating physician marks the points and/or regions for ablation, based on the GP image. Optionally, CARTO® (or other systems) understand the data and/or map, and track ablations of the GP. Optionally, the navigation system may track, guide and/or remind the operator, for example, tracking which GPs were ablated, reminding to test ablation points before and after ablation, automatically marking treated points, or other functions. Optionally, CARTO® tracks applied contract pressure and parameters to indicate how deep into the tissue the ablation is being applied.

Optionally, the navigation system (e.g., CARTO®) follows current medical practice, for example, reminding and/or tracking ablation around the pulmonary vein (PV), in addition to the GPs themselves.

Optionally, CARTO® may track one or more of the described, to estimate the probability (or provide yes/no) that the operator managed to ablation the GP (which is at a distance from the wall or not). Optionally, CARTO® suggests parameters and/or gate ablation to apply to ablate the GPs, for example, based on the location of the GP, the ablation method, the tissue type, or other factors.

Optionally, CARTO® tracks how deep away from the inner surface of the heart, arteries, and/or other chambers the operator needs to ablate to reach target tissues (e.g., GP).

Optionally, the described CARTO® procedure tracking may be used in other contexts, for example, for ablation of live tissue in the middle of the ventricle wall.

Optionally, electrical data is collected, and the model is marked-up with the electrical data. For example, electrical mapping of the heart. Electrical data may be collected, and/or the marking up performed using the CARTO® system.

Optionally, the treatment is planned based on the reconstructed functional image (e.g., method of FIG. 2B) showing the GPs and/or ANS connectivity map overlaid on the obtained anatomical image. Alternatively or additionally, the treatment is planned based on the reconstructed functional image alone. The overlaying on an anatomical image may be performed in real time during treatment, for example, overlaying the functional image over a fluoroscopic image.

Optionally, the system is set-up for ablation of the located GPs. For example, the treatment catheter may be selected, the power level for the applied treatment may be selected and/or set, or other parameters may be selected and/or set.

When SPECT data is forwarded to a workstation that is part of the navigation system, the workstation may merge a real time electro-anatomical map (obtained before and/or during the treatment) with the SPECT data acquired as described above. For example, the workstation may merge the ANS map (e.g., a CT map with SPECT data showing ANS component(s)) with the electro-anatomical map to mark-up the ANS model. The results may be presented to the operator as an annotation of colored targets on the electro-anatomical map (e.g., on output element 516). For example, for heart treatment, image registration is made by aligning the left ventricle (LV) in images from the different information sources so that the SPECT mIBG spots from a cloud of spots falls in the atrial wall (per the segmented anatomical image).

According to some embodiments of the present invention, different regions of the functional data, for example the SPECT image, are associated with different organs or tissues, for example with a nervous tissue and surrounding tissues mapped according to one or more mapping functions. The mapping functions may be defined in advance, for example by a multivariate analysis of SPECT data, for example Dynamic SPECT data and angiographic data. The map may allow differentiating between different regions of the imaged intrabody volume based on kinetic behavior and/or uptake rate.

Figure 12:
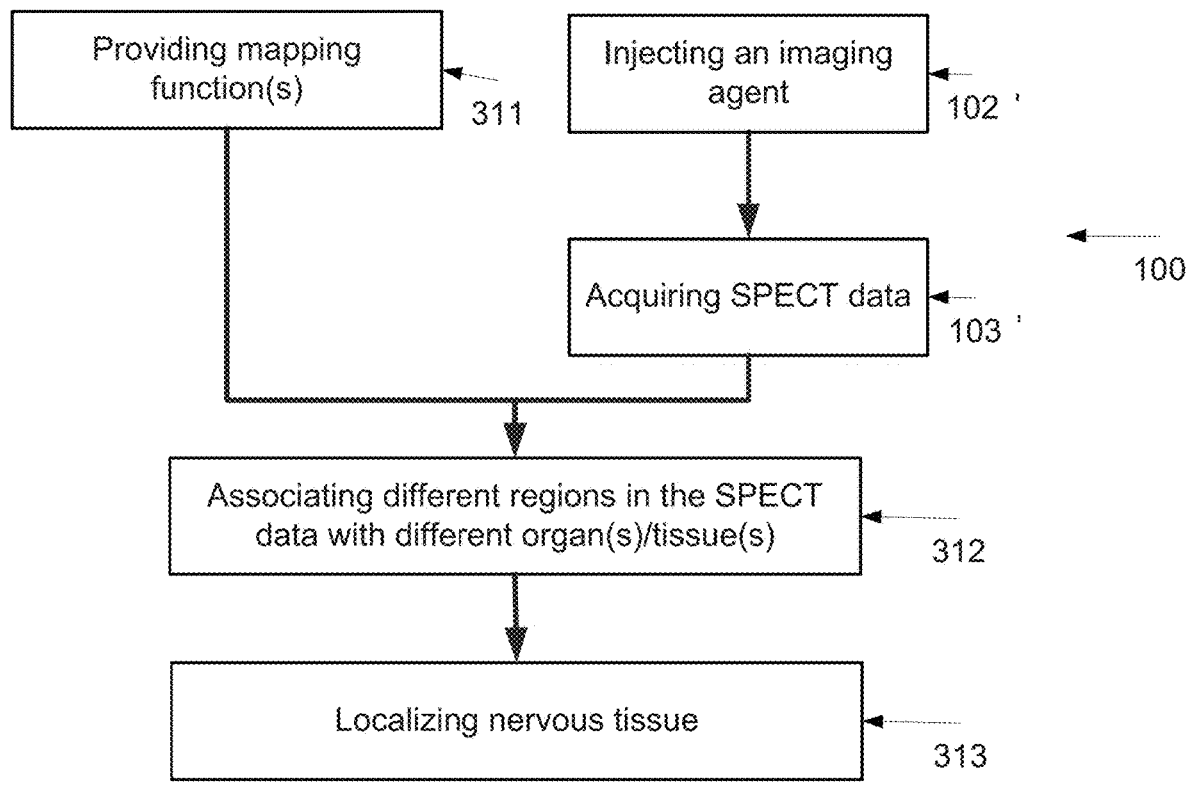

For example, FIG. 12 is a flowchart of a method 100 of localizing a nervous tissue based on an association of different regions in a functional (e.g., SPECT) image or data to different organs and/or tissues based on a mapping function, according to some embodiments of the present invention. 102', 103' are as described above with reference to block 208 of FIG. 2A. In 311, a mapping function may be provided, for example from a memory of a computing device (e.g., a mapping module 502B stored on memory 506). As shown at 312, the mapping function may be used for associating one or more regions in the functional (e.g., SPECT) image to one or more organs and/or tissues. As shown at 313, the mapping may allow localizing a target tissue in relation to surrounding tissues, e.g., for separating a nervous tissue (e.g., ganglia) from a surrounding area.

Referring back to FIG. 2A. Optionally, at 226, a catheter is inserted into the body of the patient. The catheter may be inserted through the vascular (e.g., femoral artery access to the heart). A single catheter may be inserted (e.g., dual functions), or two catheters, for example, one catheter for verifying the treatment points (e.g., electro-stimulation) and/or one catheter for ablation.

Optionally, the ablation treatment catheter is compatible with the CARTO® system, or is provided with the CARTO® system.

Optionally, at 228, the catheter is navigated to the first treatment point based on the annotations, for example, based on the anatomical annotations. For example, the operator is presented with a real-time fluoroscopic image overlaid with the ANS map so that the catheter may be navigated in real time to the correct location (e.g., to a specific GP).

Optionally, the catheter is navigated within the patient based on the CARTO® system. Optionally, the catheter is positioned for ablation towards the GPs displayed using the CARTO® system.

Optionally, the catheter is navigated based on the reconstructed functional image pre-overlaid on the anatomical image, for example, the registered and/or overlaid images have been loaded to the navigation system. Alternatively or additionally, the catheter is navigated based on the reconstructed functional image overlaid on a real-time anatomical image (e.g., fluoroscopic image), for example, the reconstructed functional image loaded to the navigation system, the navigation system obtaining the real-time anatomical image. Alternatively or additionally, the catheter is navigated based on the reconstructed functional image alone, for example, navigation may be based on position sensors.

Optionally, navigation of the catheter is based on position sensors. The position sensors may correlate to the reconstructed functional image and/or ANS map. Alternatively, navigation of the catheter is not based on position sensors. For example, navigation may be based on visual image, such as the reconstructed functional image overlaid on a real-time image of the catheter inside the targeted innervated tissues.

Optionally, the catheter is navigated to the located treatment site. Optionally, the localization may be a real time localization which is based on functional data and/or anatomical data which are captured simultaneously or substantially simultaneously and/or during a treatment period, for example during a medical treatment.

Optionally, at 230, the location of the catheter at the treatment point(s) is functionally verified. Functional verification may be performed manually by the operator and/or automatically by a verification module programmed to perform one or more of the verification process. For example, the operator applies the stimulation and the module analyses the results. In another example, the module automatically both applies the stimulation and analyses the results. In yet another example, the module applies the stimulation and the user analyses the results.

Optionally, the treatment points are functionally verified by the CARTO® system. For example, the point may be confined by applying high frequency stimulation to the points and measuring the response. Optionally, the application of high frequency stimulation is to the points and their surroundings, e.g., to compensate for any minor errors in ANS map (e.g., due to noise or registration).

According to some embodiments of the present invention, one or more nervous tissues may be localized by stimulating a nervous tissue in a certain intrabody area and identifying one or more nervous responses in response to the stimulation. The stimulation may be pharmacological, mechanical, thermal, and/or electrical, for example, high frequency stimulation (HFS). In such embodiments, after a nervous tissue in an intrabody volume of a patient is stimulated to trigger a nervous response which is associated with a certain reference uptake value, a functional data from a functional modality may be acquired, for example as described above. The functional data may be then analyzed to localize the nervous tissue in the intrabody volume according to the reference uptake value.

Optionally, the reconstructed image is used to get to a region. Tests on one or more points are performed in the region, for example, to determine response to HFS, DF, or other testing methods.

Optionally at 232, the identified and/or located treatment point (e.g., GP) is ablated, for example, using the catheter, for example, with an electrical, chemical, cryo, and/or other methods of ablation.

Ablation may be irreversible (e.g., necrosis of tissue) or reversible (e.g., using botox).

The ablation may be performed from nearby tissue, for example, from inside the heart chamber to a GP in the heart wall. The ablation may be performed within the GP itself, or next to the GP, for example, by inserting a needle through the heart wall into the GP itself or nearby. Ablation within the GP itself may spare surrounding tissue.

Optionally, the GPs are ablated using the CARTO® system. For example, energy is delivered and/or controlled using the CARTO® system.

Optionally, GPs are ablated. Optionally, regions containing GPs are ablated. Optionally, regions in the heart wall and/or surrounding vasculature are ablated. Optionally, regions in the pulmonary vein are ablated.

Optionally, the catheter contains an ablation element, for example, at the catheter tip. Optionally, the catheter is designed for a force to be applied to push the ablation element against the target tissue and/or inside target tissue. For example, the ablation element is a needle inserted into the heart wall, or through the wall to reach a fat pad, to inject chemicals such as permanent poisons (e.g., alcohol) or temporary (e.g., botulism toxin) and/or an electrode positioned against the heart wall.

Optionally, the ablation element is positioned and/or directed based on the location of the identified GPs. Optionally a force is applied (e.g., automatically by a robot and/or manually by a user). Optionally, ablation energy is applied. The amount of applied force and/or ablation energy are optionally related and/or measured (e.g, by the catheter tip) to the location of the identified GP that is to be ablated, for example, by a table, a mathematical relationship, or other methods. For example, a GP located 0.5 cm away from the inner surface of the heart chamber may be ablated by the ablation element located at the surface of the inner heart wall applying certain energy. Another GP located 1 cm, or other distances away from the inner wall may be ablated by higher applied energy, and/or by applying a stronger force of the ablation element into the inner wall. In another example, ablation may be performed by high power ultrasound that is focused by the catheter, changing the focus based on the depth. Optionally, at 234, the effects of the ablation are monitored. The effects on the immediate target organ may be monitored. The effects on other organs of the body may be monitored. For example, the effects on the heart and/or the response of the heart to the ablation of the GPs may be monitored.

Optionally, monitoring is performed by repeating at least some of the imaging of the ANS. Alternatively or additionally, monitoring is performed by repeating at least some of the stimulation. The results of the stimulating post-ablation may be compared to the effects of the stimulation pre-ablation. The effects of the ablation may be monitored by the comparison.

Optionally, monitoring is performed clinically and/or using equipment, for example, by clinically observing the patient, by performing measurements (e.g., blood pressure, cardiac output, ECG), and/or other methods.

According to some embodiments of the present invention, functional data (also referred to as SPECT data) may be combined with anatomical data for an ablation procedure, for example for ablation of a nervous tissue in the vicinity of the atria, for instance as described below. For example, reference is now also made to FIG. 4 which is a flow of clinical protocol for neural modulation of one or more GPs in the atria, according to some embodiments of the invention. First, as described above, the patient may be injected with I-123 labeled mIBG, for example in a dose of between about 3 mCi and 8 mCi or between about 2 mCi and 12 mCi, for example about 5mCi. The data or the image of the mIBG tracer with high sensitivity—using high resolution scanner for example D-SPECT may allow localization in a distinguishable manner the location of active GPs, for example in ROIs of the atria. The patient may also be injected with a supporting radiopharmaceutical, such as Tc-99m labeled tracer for cardiac perfusion mapping, for instance based on a tracer such as Sestamibi-Tc-99m, Tetrofosmine-Tc-99m, and Teboroxime-Tc-99m. For example, the dose of the Tc-99m labeled tracer is between about 6 mCi and 12 mCi, between about 3mCi and 10 mCi, or between about 2mCi and 15 mCi, for example about 10 mCi, about 8 mCi and about 5 mCi. In some examples, the GP localization occurs at rest and/or at stress.

The localization may be done on the uptake of the radiotracer (I-123 labeled and Tc-99m labeled) one after the other, for example, first inject I-123 labeled mIBG, then image, then inject Tc-99m labeled tracer then image. In another example, the localization may be done on both radiotracers (I-123 labeled and Tc-99m labeled) simultaneously, thus allowing to obtain fully registered images of the tracers, and in shorter time frame. In some examples, both tracers are injected with the dose ratio of about 2:1 between the Tc-99m labeled tracer and the I-123 labeled tracer. For example, about 10 mCi of Tc-99m (such as sestamibi-Tc99m) simultaneously with about 5 mCi of mIBG-I-123. In other example, ratio of between about 1:1 to 3:1 is used, or ratio of between about 1.5:1 to 2.5:1 is used.

Optionally, functional imaging (e.g., for the GP localization) and/or the simultaneous multiple-tracers localization may include photon acquisition over a period of time of about 10 minutes, about 5 minutes, about 3 minutes, about up to 2 minutes, about 8 minutes, about 2 to 8 minutes, about up to 10 minutes, about up to 15 minutes, and/or about up to 20 minutes.

Optionally, at 236, the effects of the treatment matching the ANS model is confirmed. Treatment may continue upon confirmation, or end if all points have been treated and/or the desired effect (full or partial) has been achieved. Alternatively, the effects do not match the ANS model, in which case, for example, the operator may decide to stop treatment or re-evaluate the next treatment point.

Optionally, the effects of ablation treatment are confirmed using the CARTO® system. Optionally, HFS is applied to the treatment area by the CARTO® system. A negative response may indicate successful ablation of the GP.

Optionally, the effects are determined based on repeating at least some of the imaging of the ANS. Alternatively or additionally, the effects are determined based on repeating at least some of the stimulation. The results of the imaging and/or stimulating post-ablation may be compared to the imaging and/or effects of the stimulation pre-ablation. The effects of the ablation may be monitored by the comparison.

Optionally, at 238, additional locations are ablated based on the treatment plan and/or based on the monitored effects. Alternatively, treatment is continued at the same point.

Optionally, some of the blocks of the method are repeated, optionally, the catheter is moved or rotated to another location (228) or remains in the same location; the point is verified (230) or the same point is maintained; the point is ablated (232), the effects are monitored (234) and/or the effects are confirmed (236).

Optionally, at 240, progression is monitored after the treatment session has been completed. The patient may be monitored on an outpatient basis, for example, by clinical examination, blood tests, ECG, or other methods. The patient may be monitored by repeated functional and/or anatomical image. The patient may be brought in for one or more additional treatment sessions.

Optionally, the localization may be used for monitoring the nervous tissue, for example in a plurality of sessions held during a treatment period, for example: during a treatment period of a day, a week, a month, a year or any intermediate or shorter period.

The methods and/or systems described herein refer to identification and/or treatment of nerve structures in the body of a patient. The methods and/or systems may be used for ablation of other structures in the body. The other structures may not been visible (e.g., too small, resolution not high enough, similar to surrounding tissue) using anatomical imaging modalities, for example, lymph nodes, cancer metastases, or other structures. For example, to detect metastatic thyroid cancer, TSH-stimulated low-dose 1311 whole-body scanning with serum thyroglobulin either by standard LT4 withdrawal or rhTSH stimulation may be used. For example, to detect bone metastases, 99m Tc methylene diphosphonate (MDP) may be used. For example, to image lymph nodes, 18F-FDG may be used. Optionally, the systems and/or methods may be used for identification of objects with an expected size and/or shape and/or activity located within a window relative to anatomical landmarks that may be mapped using the functional modality and/or anatomical modality that may be registered to another image, such as a nuclear medicine image. It is noted that combined CT and nuclear medicine imaging may be performed to obtain anatomic registration, and then apply the method described with reference to FIG. 2B.

One or more of the blocks of method 200 of FIG. 2A are now discussed in additional detail.

Figure 4:
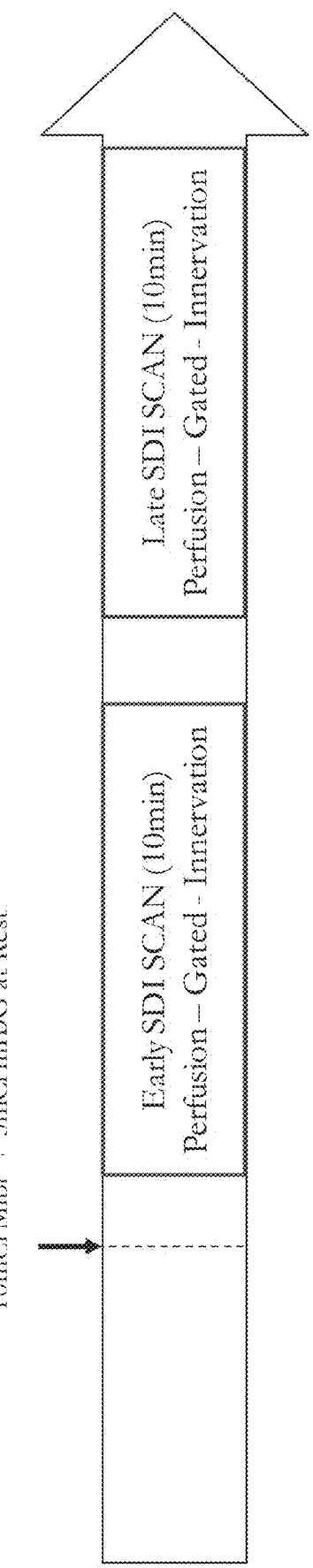
Figure 5:
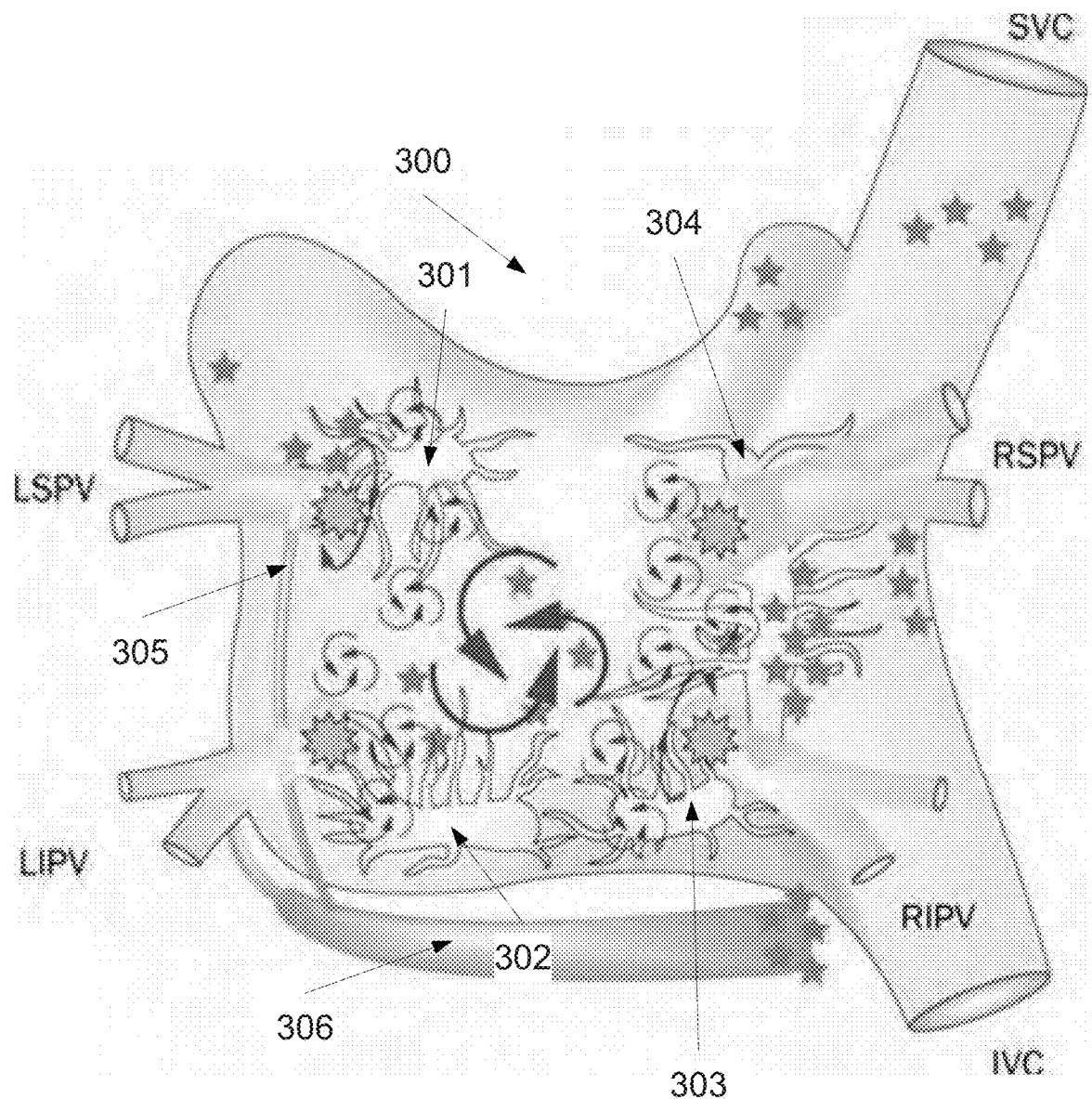

With reference to block 212, optionally, as depicted in FIG. 4, the localization may occur in a number of sessions, for example to provide an early image and a late image (repeating blocks 206, 208 and/or 210). For example, a first localization step of about 10 minutes is followed by a wait period which is further followed by a second imaging step of about 10 minutes. In some examples, the wait period between imaging steps is of about 5, about 10, about 20, about 30, about 45, about 60, about 90, and about 120 minutes or any intermediate or longer periods. For example, the wait period is between about 5 and about 30 minutes, between about 20 and about 60 minutes, between about 30 and about 120 minutes, between about 1 and about 5 hours, or between about 2 and about 48 hours.

With reference to block 228, the operator may navigate a catheter into the heart for treatment. For example, reference is now made to FIG. 5, which is a schematic illustration of a human heart 300 and a set of four ganglionic plexi (GPs) 301-304 and their axons respectively in the superior left GP (SLGP), inferior left GP (ILGP), anterior right GP (ARGP), and inferior right GP (IRGP) of the human heart 300. The image also depicts a coronary sinus 306, which is enveloped by muscular fibers that have connections to the atria, and the vein and ligament of Marshall 305, which travels from the coronary sinus to the region between the left superior pulmonary vein (LSPV) and the left trial appendage (LAA) and includes the Marshall GP. The GPs are located in fat pads. One GP is located at the right pulmonary vein (RPV) fat pad located at the junction of the right atrium and right pulmonary veins and provides a direct vagal inhibition of the Sinoatrial (SA) node. Another GP is located in the inferior vena cava and inferior left atrium (IVC-ILA) fat pad, at the junction of the IVC and ILA, selectively innervates the Atrio Ventricular (AV) nodal region and regulates AV conduction. Another GP is located in the SVC-AO fat pad, between the medial superior vena cava (SVC) and aortic root superior to the right pulmonary artery, a "head station" of vagal fibers projecting to both atria and to the IVC-ILA and PV fat pads.

One or more of the heart neural structures may be displayed for the operator for navigation and/or treatment. The combination between the functional data and the anatomical data may allow guiding the ablation process (e.g., by creating ANS map or data), for example by indicating to the operators where the GPs are located (block 224), allowing the operator to ablate some or all of them by operating the ablation unit as described above (block 232). The ablation unit is optionally used for high-frequency stimulation when guided to proximity with some or all of the above GPs and/or another ganglia area. Optionally, pre acquired segmented images are used, for example anatomical imaging data from a model indicating the location of some or all of the above GPs, for example imported via an image integration module, such as CartoMerge™ module (block 222). Optionally, data pertaining to the treated GP is acquired and used for the imaging and/or the guiding of the treatment process, for example spatial distribution and/or thickness of the epicardial fat in the surrounding area, for example of the fat pad wherein the GP is located. For example, ablation of GP may be an option for treatment of patients with paroxysmal or persistent Atrial Fibrillation (block 220).

Referring to block 210, optionally, the functional data is segmented before the combination thereof with the anatomical data. For example, pulmonary vein (PV) sections, left atrium (LA) sections, and/or GPs are segmented, for example based on a match with a model.

Figure 6:
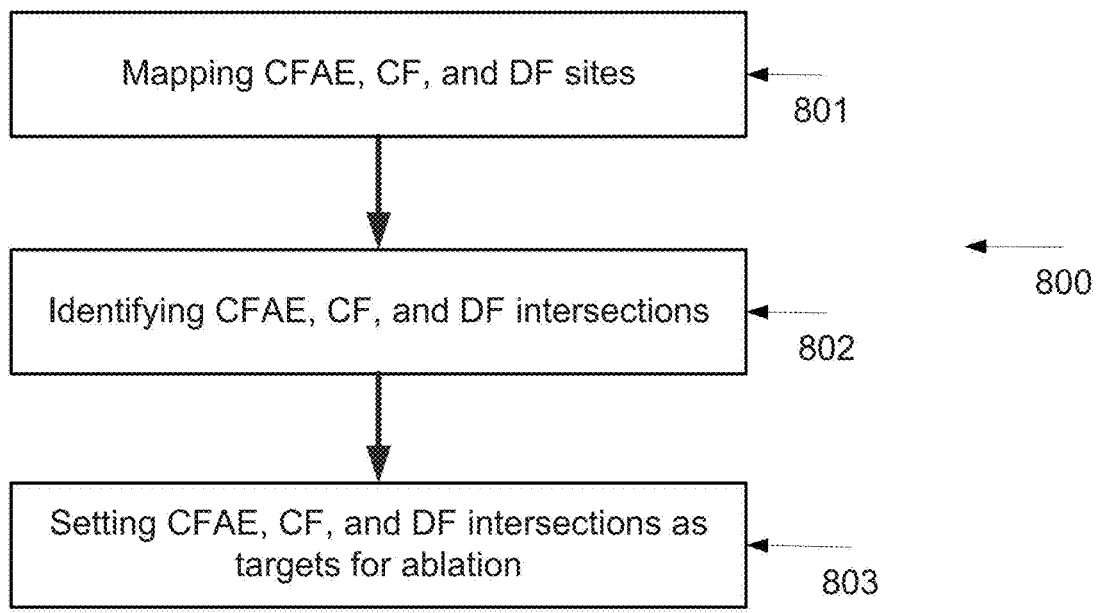
Figure 10A:
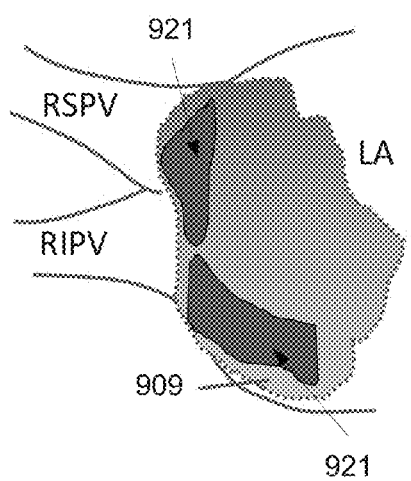
Figure 10B:
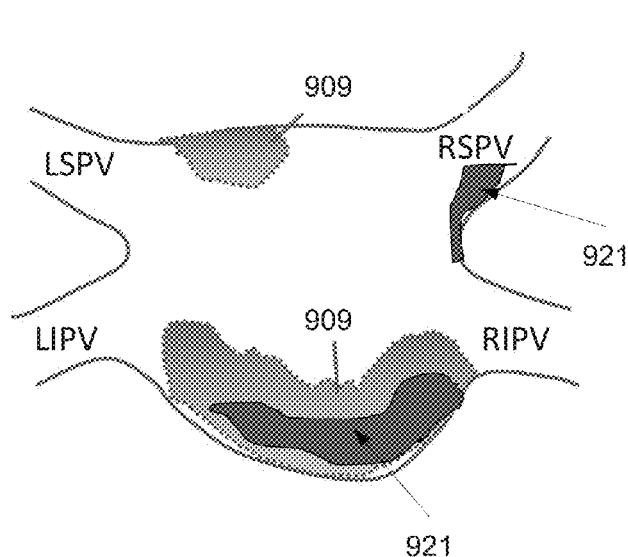
Figure 10C:
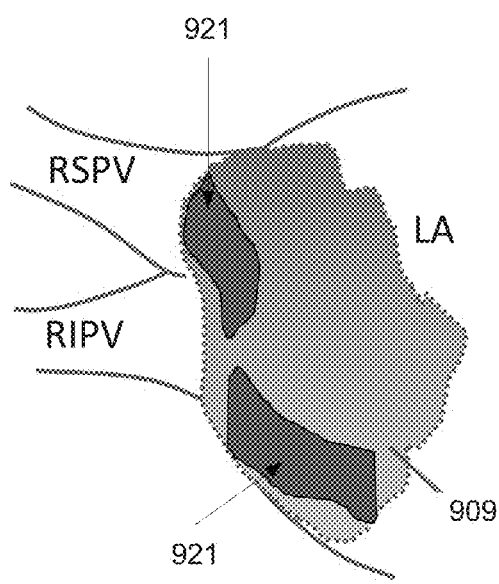
Figure 10D:
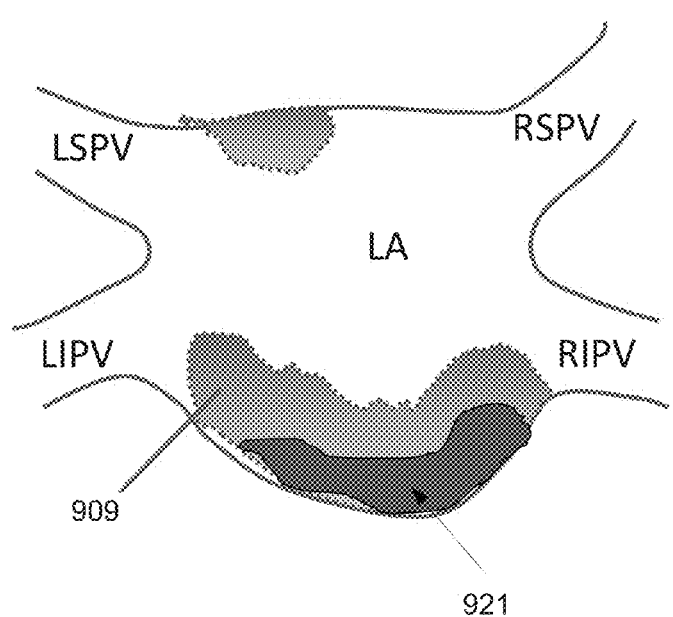
Figure 11A:
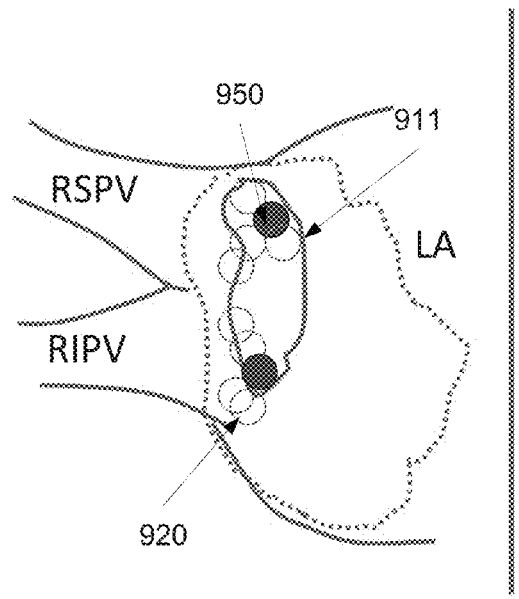
Figure 11B:
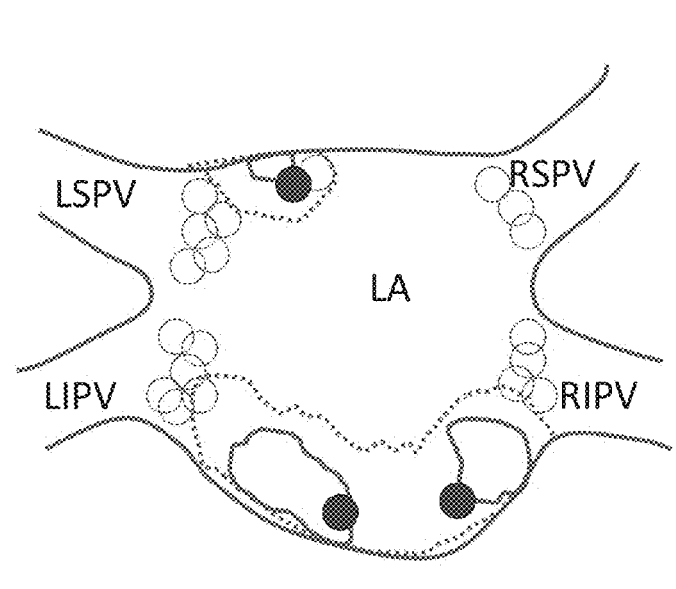
Figure 11C:
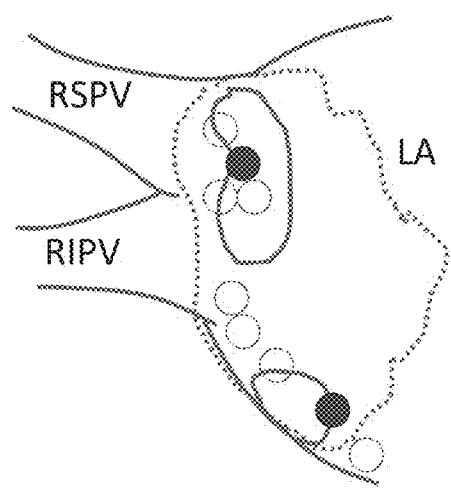
Figure 11D:
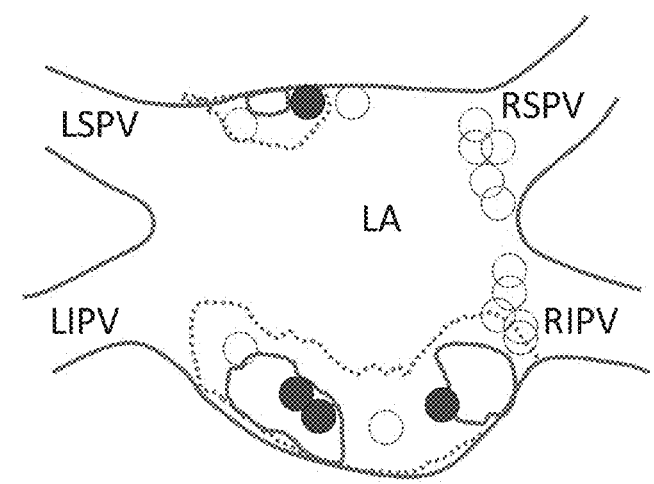

Reference is now made to FIG. 6, which is a flowchart of another method 800 for performing an ablation treatment by mapping complex fractionated atrial electrograms (CFAE) sites, contractile force (CF) sites, and/or dominant frequency (DF) sites in the atria as target areas, according to some embodiments of the present invention. The method of FIG. 2A may be modified according to the method of FIG. 6. First, as shown at 801, CFAE, CF, and DF sites may be mapped, for example, an ANS model may be generated (block 214), and/or the sites may be displayed on the model (block 224). Then, as shown at 802, intersections between the CFAE, CF, and DF and/or CFAE, CF, and DF and GPs may be calculated. The intersections may be with anticipated sites of anatomically known GPs, for example the above described GPs, with pre-acquired localized GPs, for example GPs which are identified in the SPECT data, and/or intersections with GPs located in real time by high-frequency stimulation. Then, as shown at 803, the intersections may be selected as target areas for ablation (e.g., block 224).

For example, reference is now made to FIGS. 7A-7D, FIGS. 8A-8D, FIGS. 9A-9D, FIGS. 10A-10D and FIGS.

11A-11D. Each set of figures having a common numeral includes CFAE, CF, and/or DF sites and/or intersections of CFAE, CF, and/or DF sites in four views (clockwise): right anterior oblique (RAO). Posterior-anterior (PA) view, a right lateral view (left side) and a posterior view (right side), which may be identified, for example, using the method described in FIG. 6, according to some embodiments of the present invention. FIGS. 7A-7D depict a mapping of CFAE areas 707. FIGS. 8A-8D depict a mapping of CFAE areas 909 and the intersections thereof with ARGP 911, SLGP 912, ILBP 913, and IRGP 914. FIGS. 9A-9D depict a mapping of CFAE areas 909 and intersections thereof with both ARGP 911, SLGP 912, ILBP 913, and IRGP 914 and with DF sites, for example site 920. FIGS. 10A-10D depicts a mapping of CFAE areas 909 and intersections thereof with CF sites 921. Optionally, an intersection between a CFAE area, a DF site, and a GP is identified as a target location for ablation, for example see the full dots depicted in FIGS. 11A-11D which are RAO, PA, a right lateral, and a posterior views, for example the full dot 950. Optionally, a full intersection is preferred over a partial intersection.

In addition to, or instead of GP detecting per se, the nervous tissue is typically composed of neurons, axons and synapses and typically contains a high fat composition and/or located within and/or in proximity to fat tissue. As a result, structural imaging of nervous tissue is challenging, at least. Methods for detecting or locating ganglions of the nervous tissue are described above. In some exemplary embodiments of the invention, such methods are extended and/or supplemented to detect synapses and/or other nervous tissue which innervates a target tissue such as the heart, GI tract, or other tissues and/or end organs as described herein.

In some embodiments of the invention, a functional imager (e.g., SPECT or PET) may use a tissue specific tracer (mIBG for example or another tracer) with affinity to one of the functions related to the autonomic nervous system (e.g., Nor Epinephrine production, secretion or processing, Acetylcholine production, secretion or processing and/or Dopamine production secretion or processing).

Additional details of suitable tracers may be found, for example, with reference to PCT application titled "NERVE IMAGING AND TREATMENT", co-filed with the present application.

In some embodiments of the invention, the specific tracer is selectively taken up by the target nervous tissue and functional information may be acquired (e.g., as radiation counts). In some cases, the acquisition is timed to a stimulation or other modulation of the nervous system, for example, drug provision, electrical stimulation, mechanical stimulations, body interaction (e.g., cold water on hand or face) and/or exercise, so that the acquired data can reflect not only a steady state of the body but also, or instead, reaction to a stimulus.

Various methods are known in the art to inject these tracers to receive images of intra body uptake thereof. However, the signal to noise of these tracers, coupled to the low resolution and sensitivity of the imaging machines was considered (to the extent the possibility was raised, which is not clear) a barrier to identify and localize small targets, for example, tissue denervation and/or ganglions. In some exemplary embodiments of the invention, for example, as described herein, nervous tissues with a maximal extent smaller than, for example, 20 mm, 10 mm, 5 mm, 3 mm and/or 2 mm are identified. Optionally or alternatively, innervated tissue is identified, for example, with surface sizes of less than, for example, 10 cm sq, 5 cm sq, 4 cm sq or smaller.

In some exemplary embodiments of the invention, activity of the autonomic nervous system (ANS) is identified and/or localized, for example, with a resolution good enough to identify ganglions (e.g., <10 mm, <5 mm) and/or synapses, for example, the distribution of intra-tissue synapses of the ANS.

In some exemplary embodiments of the invention, the functional data may be segmented using an anatomical model (e.g., structural or anatomical imager—for example: an X-ray CT image). In some embodiments of the invention, a reconstruction of the functional data is performed using the structural model provided by the structural imager (e.g., CT). In some embodiments of the invention, functional data is assigned to tissue according to the segmentation. In some embodiments of the invention, activity tissue within the organ is analyzed according to an assumption re innervation. For example, processing is optimized for sensitivity, at the expense of resolution. Tissue outside the organ is optionally processed with an emphasis on resolution, for example, to detect objects of a size, shape and/or location which match anatomical expectations of ganglions. In some embodiments of the invention, the locations are relative to anatomical landmarks on the organ and/or as a function of distance from the organ boundary.

In some examples of a heart, anatomical data, such as from a CT imager may be combined with functional data (e.g., mIBG data and/or data from cardiac tracers) and various algorithms (e.g., for example algorithms described in U.S. Pat. No. 8,000,773 and related applications) may be used to detect the boundaries of the myocardium of the 4 chambers and/or related structures of the heart. Then the registration of the different images from the different modalities may be performed and used to distinguish the relevant mIBG activity within the corresponding volume of the myocardium.

In some embodiments of the invention, ANS component(s) (e.g., ganglions) are identified or detected or localized using methods as described above, for example, using the method of FIG. 2B. Optionally or alternatively, the following method may be used. The general (e.g., average) activity of mIBG may be measured in a region (reapplied with various sizes) and compared to a threshold which may be a function of variation of the mIBG activity in the region (e.g., 2, 3, 4, or intermediate standard deviations of the regional activity). Optionally or alternatively, bodies of the size of, for example, 1, 2, 3, 4, 5, 6, 7, 8, 9 mm or more or intermediate sizes that appear in multiple (e.g., 2, 3, or more runs (e.g., with various region sizes and/or locations) may be identified as ganglia.

In some embodiments of the invention, at least two finds of a same body location in a region of size that is larger in volume by a factor of at least 2, 4, 6, 8, 10, 20 or intermediate amounts, than the found suspected ganglion, are required.

In some embodiments of the invention, sympathetic and parasympathetic ganglia and synapses may be distinguished by stimulating with a stimulus which affects only one and detecting which ganglia and/or synapses are affected. For example, such stimulation may be provided simultaneously with injection of a tracer and uptake of the tracer compared to standard speed.

In some embodiments of the invention, afferent and efferent nerve conduits may be distinguished by selectively stimulating at one point and comparing effects upstream and/or downstream and/or determining the order of activation or other effect at two points along the conduit. For example, in efferent conduits, activity is expected to show first and/or more strongly in ganglions. Blocking the ganglions, for example, using a suitable electrical and/or pharmaceutical stimuli may prevent and/or reduce synapse activity. In parasympathetic nervous tissue the opposite effects are expected.

Figure 13:
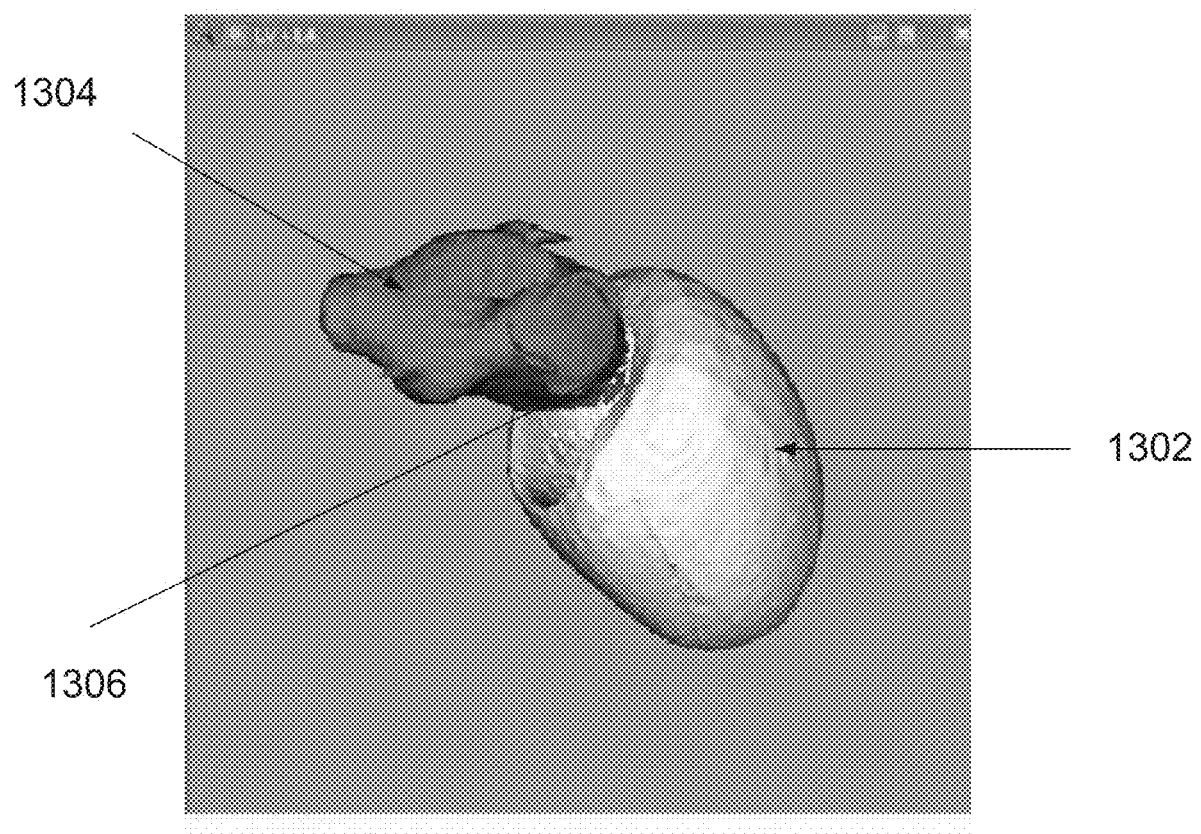
Figure 14:
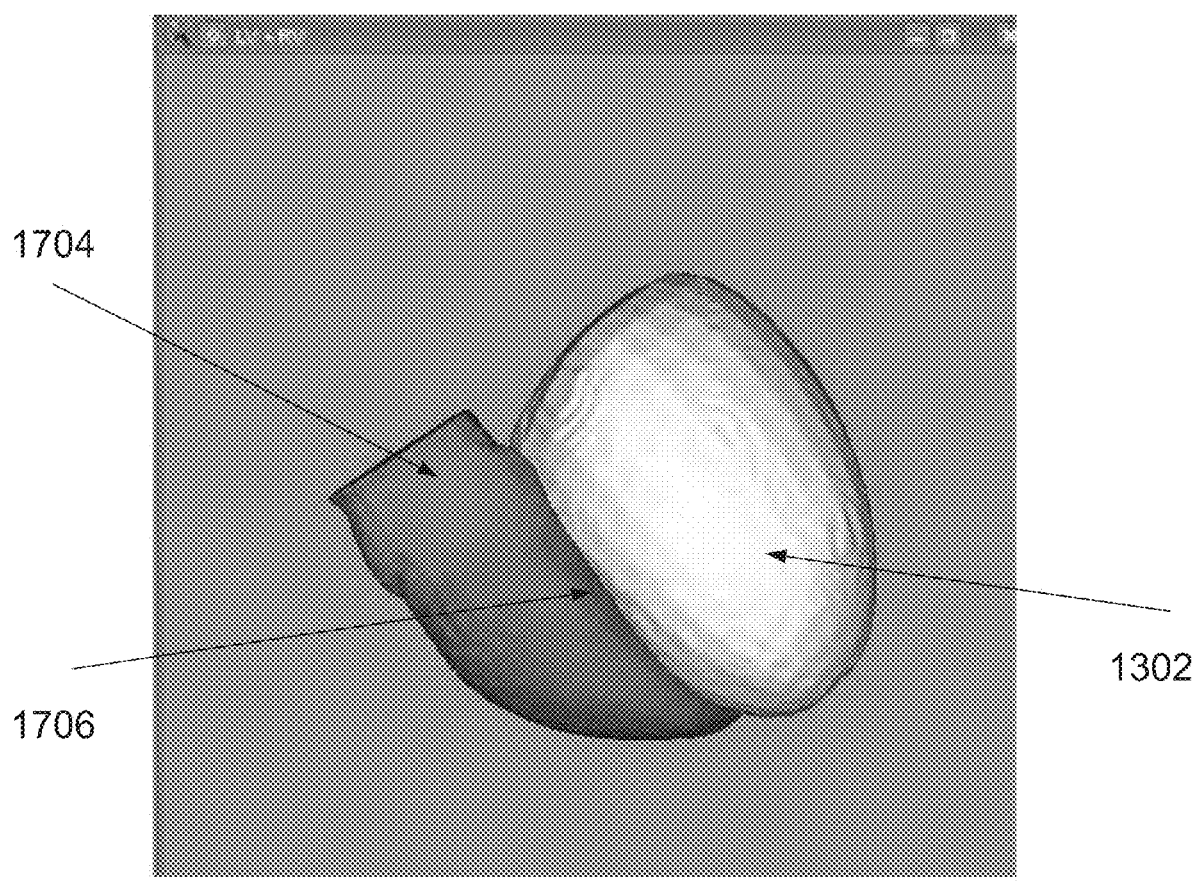

FIGS. 13-15 show the distribution of the sympathetic synapses on the heart as imaged on a human patient, whose heart was segmented using x-ray CT images, in accordance with exemplary embodiments of the invention.

In general, in these images, the colors are calibrated according to relative mIBG activity, with red being high activity and green being low activity. Ganglia are not shown in these images.

FIG. 13 shows an image of the left atrium 1304 and left ventricle 1302, in which the left atrium is colored in accordance with mIBG activity according to an exemplary embodiment of the invention, showing a maximal activity level in the left inferior pulmonary vein 1306;

FIG. 14 shows an image of the right ventricle 1704 and left ventricle 1302, in which the right ventricle is colored in accordance with mIBG activity according to an exemplary embodiment of the invention, showing a maximal activity level in the intra ventricular septum 1706, which is an intra-septal hot spot. Ablation at 1706 may treat Hypertrophic cardiomyopathy (HCM) and/or hypertrophic obstructive cardiomyopathy (HOCM); and FIG. 15 shows an image of the left atrium 1304 colored 1906 in accordance with mIBG activity, according to an exemplary embodiment of the invention. Of particular interest is a hot spot of activity near the inter-ventricular speta, which has apparently not been known in the art and not used for planning treatment and/or diagnosis. In some embodiment of the invention, the resolution of the areas of activation is between 1 and 10 mm in linear resolution (e.g. 3 mm, 5 mm, 7 mm or intermediate resolutions), for separating between locations in different decades of percentiles in a histogram of mIBG activity, as measured by counts.

It is also noted that while there may be some correlation between fat pad location and synapse locations and this may be used to guide image reconstruction, for example, to preferentially assign mIBG counts to those regions, the fat pads do not necessarily indicate the exact pattern of densities of synapses.

Reference is now made to a set imaging sessions and ablations performed to image and to treat target areas, cardiac sites with ganglionic plexuses, according to some embodiments of the present invention.

The target areas have been identified according to the above methods, for example according the method of localizing nervous tissue based on a combination of anatomical data and functional data—e.g., SPECT data, of an intrabody volume depicted in FIGS. 2A-B and/or using the system depicted in FIG. 3. In some embodiments of the invention, the following procedure may be used: a CT anatomical image of the heart and its surroundings and a mIBG nuclear medicine (NM) image of the heart and its surrounding may be acquired.

Optionally, the shape of the heart identified in the CT image is used for reconstructing an NM image. In some embodiments of the invention, hot regions outside of the heart may be identified as Ganglions. The reconstructed combined image, with indications of the ganglions may be used with an image navigation system, such as the Carto system by Biosense Webster®, which allows navigation of a catheter in the heart and overlaying of the catheter location on a previously acquired image. Such a system is optionally used to guide an ablation catheter to parts of the heart (e.g., the atria) adjacent ganglions. To confirm the presence of ganglions, high frequency stimulation (HFS) stimulation (or other type of stimulation) may be used. Once confirmed, or possibly without HFS stimulation, which results below suggest may be redundant, ablation at or adjacent an identified ganglion may be carried out. Optionally, the use of precise navigation allows the use of a lower power and/or lower number of ablations. For example, fewer than 20, 10, 5 or intermediate numbers of ablations per heart and/or ganglions may be applied. Optionally, lower power, such as 40 watts (e.g., for RF ablation), 30 W, 20 W, 10 W, 5 W or intermediate or smaller power levels are used. Optionally or alternatively, shorter periods of time are used, for example, 60 seconds, 50 seconds, 30 seconds, 20 seconds, 10 seconds or intermediate number or fewer per ablation.

In a first example, a 60 years old Male having a BMI 22 (176 cm/69 kg) and a medical history of Ventricular arrhythmias, chest discomfort, Low EF (LVEF 35%) and non-ischemic cardiomyopathy, was localized, namely performed a CT scan and having a set of cardiac sites, referred to herein as GP1, GP2, and GP3 identified according to the method and/or system described above with reference to FIGS. 2-3. GP1, GP2, and GP3 are depicted in FIGS. 21A, 21B, and 21C where each one of these figures includes, from left to right, a transverse cut image, a coronal cut image, and sagittal cut image. GP1, GP2, and GP3 are localized also in FIGS. 22A and 22B after estimated locations have been correlated with a map of typical anatomical GP locations in the heart. GP1, GP2, and GP3 are localized also in FIG. 22C when overlaid on sympathetic synapse density maps. The red dots represent the major GP (relatively larger size) and the red areas on myocardium represent minor GP sites (relatively smaller size).

In a second example, a 47 years old Male having a medical history of paroxysmal atrial fibrillation catheter ablation for PVI and CVI and normal LV contraction, LVEF=60%, LDDd=47, and LAD (dimension of lt.atrium)=36 is localized, namely performed a CT scan and having a set of cardiac sites, referred to herein as GP1, GP2, GP3, and GP4 identified according to the method and/or systems described above with reference to FIGS. 2-3. GP1, GP2, GP3, and GP4 are depicted in FIGS. 23A23B, 23B, 23C and 23D where each one of the figures includes, from left to right, a transverse cut image, a coronal cut image, and sagittal cut image. The images in FIGS. 23A, 23B, 23C and 23D are images that combine the images captured according the method and/or system described above with reference to FIGS. 2-3 and a respective CT image. The location of the localized GP sites was integrated into a Carto system for ablation guidance, for example as shown at FIG. 24. The figure shows the location of GP sites on a rendered anatomical image. An operator may navigate a catheter for ablation of the GP sites based on the rendered anatomical image.

Reference is now made to a set of presentations imaging cardiac GP sites on a 3D simulation of the heart of a patient. The GP site was verified by measuring the reaction of the target site, for example having a volume with a diameter of less than 10 millimeters (mm), for instance 5 mm, for instance 3 mm, to a HFS at each one of the mapped GP sites where the ablation itself is performed by a low power of up to 30 watt (W), for example up to 20 W, for instance 10 W, for instance 5 sessions, and for instance 3 sessions, for about 20-30 seconds in less than 20 applications, for example about 3 repeated applications. In this procedure, fragmentation changes and termination of the atrial fibrillation are monitored. FIG. 25 depicts HFS application site (marked with a circle having a dashed pattern) on a 3D simulation of the heart of a patient. The application site is a non GP site. A negative response to this appliance is demonstrated in FIG. 26. FIGS. 27A and 27B depict HFS application site (marked with a circle having a dashed pattern) on a 3D simulation of the heart of a patient. The application site is the RIPV GP Site. A positive response to this appliance is demonstrated in FIG. 28. FIGS. 29 and 30 depict repeating the HFS application at the RIPV GP Site. The positive response to this repetition is demonstrated in FIG. 31.

FIGS. 32 and 33 depict HFS application site (marked with a circle having a dashed pattern) on a 3D simulation of the heart of a patient. The application site is the LIPV GP Site. This site was ablated by applying a five sessions of low power applications (up to 20 W), using a catheter as described above. A positive response to this appliance is demonstrated in FIG. 34. The outcome of an ablation at the LIPV GP Site, localized in FIGS. 35 and 36, is demonstrated by FIGS. 37 and 38 which depict the negative HFS response in a post ablation measurement. This response is indicative of the success of the ablation process, even though the target area was treated with limited power in a limited number of ablation sessions. The outcome of an ablation at the RIPV GP Site, localized in FIG. 39, is demonstrated by FIGS. 40 and 41 which depict the negative HFS response in a post ablation measurement. This site was ablated by applying a three sessions of applying low power (up to 20 W), using a catheter as described above. The RSPV GP Site (marked with a circle having a dashed pattern) in FIGS. 42 and 43 was also ablated. This site was ablated by applying a three sessions of applying low power (up to 20 W), using a catheter as described above.

In a third example, a 72 years old Male having a medical history of Paroxysmal atrial fibrillation/Hypertension/Dyslipidemia, LV contraction is almost normal, LVEF=66%, LVDd=40 mm, and LAD (dimension of lt.atrium)=42 mm is localized, namely performed a CT scan and having a set of cardiac sites, referred to herein as GP1, GP2, GP3, and GP4 identified according to the method and/or system described above with reference to FIGS. 2-3. The imaging was performed prior to ablation. GP1, GP2, GP3, and GP4 are depicted in FIGS. 44A, 44B, 44C and 44D where each one of the figures includes, from left to right, a transverse cut image, a coronal cut image, and sagittal cut image. The images in FIGS. 44A, 44B, 44C and 44D are images that combine the images captured according the method and/or system described above with reference to FIGS. 2-3 and a respective CT image. The location of the GP sites was integrated into a Carto system for ablation guidance, for example as shown at FIG. 45.

In a fourth example, a 72 years old Male having a medical history of Paroxysmal atrial fibrillation/Hypertension, LV contraction is normal, LVEF=58%, LDDd=37, and LAD (dimension of lt.atrium)=37 is localized, namely performed a CT scan and having a set of cardiac sites, referred to herein as GP1, GP2, and GP3 identified according to the method and/or system described above with reference to FIGS. 2-3. The imaging was performed prior to an electrophysiology (EP) study, which may help in evaluating the patient's condition, for example, to determine if the patient is suitable for treatment using the methods and/or systems described herein. GP1, GP2, and GP3 are depicted in FIGS. 46A, 46B, and 46C where each one of the figures includes, from left to right, a transverse cut image, a coronal cut image, and sagittal cut image. The images in FIGS. 46A, 46B, and 46C are images that combine the images captured according to the method and/or system described above with reference to FIGS. 2-3 and a respective CT image. The location of the localized GP site (marked with a circle having a dashed pattern) was integrated into a Carto system for ablation guidance, for example as shown at FIG. 47.

In the above experiments, we received, in response to applying a limited number of sessions of HFS at the GP sites, 100% positive response. Moreover, we learned that applying the same HFS, even multiple times, for instance more than 50 times, at non GP sites—outside of the identified GP sites achieves a negative response.

In yet another example, a patient with persistent atrial fibrillation (AF) is treated based on the method and/or system described with reference to FIGS. 2-3. FIGS. 16-20 are images generated during the various points of the method, in accordance with some embodiments of the present invention. The patient underwent 123ImiBG D-SPECT imaging before catheter ablation. FIG. 16 illustrates the uptake of mIBG in the left atrium (LA) before high frequency stimulation (HFS). 5 epicardial GP locations are identified. FIG. 17 illustrates a saturated stated of the image of FIG. 16, before HFS. FIG. 18 illustrates locations of positive HFS before the ablation procedure. The positive HFS confirms the epicardial GP locations. FIG. 19 shows location of the ablations. The ablations were performed at locations that correspond to the GP locations. FIG. 20 illustrates a negative response to repeated HFS at the GP ablated sites. The negative response denotes that the GPs have been treated. Atrial fibrillation may be controlled and/or prevented.

It should be noted that the above description mostly focuses on a localization of nervous tissue; however, the above protocols, methods, and systems may be used for a localization of endocrine secreting organ(s) and/or exocrine secreting organ(s) or other information.

It is expected that during the life of a patent maturing from this application many relevant methods and systems will be developed and the scope of the terms an ablation unit, imaging system and methods, a catheter and a modality is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of guiding a cardiac treatment using a functional imaging modality, comprising:
   providing functional imaging modality data from a nuclear medicine imaging modality which images an intrabody volume of a patient containing a heart, the patient having been injected with a radioactive imaging agent having a nervous tissue uptake by an autonomic nervous system (ANS) of the heart, the ANS comprising at least one ganglionic plexus (GP);
   receiving at least one image mask corresponding to location of a fat pad at a predefined anatomical region identified on an anatomical image acquired by an anatomical imaging modality, wherein said at least one GP is not identifiable on said anatomical image;
   applying the at least one image mask to the functional imaging modality data to the location corresponding to the fat pad at the predefined anatomical region;
   locating the at least one GP innervating the heart within the at least one image mask applied on the functional imaging modality data, by differentiating the at least one GP from the fat pad based on at least one predefined rule, said rule relying on a calculated activity of a radio labeled tracer within a spot in said respective image mask being indicative of the at least one GP, said activity being larger than activity of an area surrounding the spot within the respective image mask indicative of the fat pad, by more than a predefined threshold; and
   guiding an ablation cardiac treatment to the located at least one GP within the fat pad for treating cardiac disease.

2. The method of claim 1, wherein said functional imaging modality is a member of a group consisting of: single-photon emission computed tomography (SPECT), electrocardiogram-gated SPECT (GSPECT), SPECT-CT, D-SPECT, A-SPECT and functional magnetic resonance imaging (fMRI).

3. The method of claim 1, wherein said locating is based on analyzing said functional imaging modality data at multiple resolutions and identifying as ganglia objects which appear in multiple sizes of filters.

4. The method of claim 1, wherein said locating includes enhancing a resolution of the functional imaging by focusing the functional imaging on regions of interest (ROIs).

5. The method of claim 1, wherein said locating is based on a plurality of predefined rules derived from anatomical information.

6. The method of claim 1, wherein said locating the at least one GP innervating the heart based on the functional imaging modality data is according to an analysis of synapse distribution and activity identified in the functional imaging modality data.

7. The method of claim 1, further comprising:
   receiving an anatomical image of heart structures innervated by the ANS;
   selecting the at least one image mask by processing the anatomical image, the at least one image mask is selected to correspond in dimensions to regions of the intrabody volume containing nerve tissues.

8. The method of claim 1, wherein the predefined threshold is based on a predefined factor times a calculated standard deviation of activity within the image mask above a calculated average activity within the image mask, and a calculated adjacent activity surrounding an active region is lower than half of the activity of the active region.

9. The method of claim 1, wherein the radio labeled tracer is metaiodobenzylguanidine (mIBG).

10. The method of claim 1, wherein the rule comprises comparing activity level of the radio labeled tracer to surrounding activity within the image mask.

11. The method of claim 1, wherein the rule comprises a size of an active spot of activity of the radio labeled tracer being larger than a threshold.

12. The method of claim 1, wherein the at least one GP innervating the heart is located within the at least one image mask applied on the functional imaging modality data according to an analysis of synapse distribution or activity identified in the functional imaging modality data corresponding to the applied at least one image mask.

13. A system for identifying ANS tissue within an image of a heart of a patient and providing cardiac treatment, the system comprising:
- a non-transitory computer readable medium storing program instructions;
- at least one hardware processor in communication with said non-transitory computer readable medium, that when said instructions are executed by said at least one hardware processor, the execution causes said at least one hardware processor to:
  - receive functional imaging modality data from a nuclear medicine imaging modality which images an intrabody volume of a patient containing a heart, the patient having been injected with a radioactive imaging agent having a nervous tissue uptake by an autonomic nervous system (ANS) of the heart, the ANS comprising at least one ganglionic plexus (GP);
  - receive anatomical imaging modality data from an anatomical imaging modality which images an intrabody volume of a patient containing the heart;
  - receive at least one image mask corresponding to location of a fat pad at a predefined anatomical region identified on an anatomical image reconstructed from said anatomical imaging modality data, wherein said at least one GP is not identifiable on said anatomical image;
  - apply the at least one image mask to the functional imaging modality data to the location corresponding to the fat pad at the predefined anatomical region;
  - locate the at least one GP innervating the heart within the at least one image mask applied on the functional imaging modality data, by differentiating the at least one GP from the fat pad based on at least one predefined rule, said rule relying on a calculated activity of a radio labeled tracer within a spot in said respective image mask being indicative of the at least one GP, said activity being larger than activity of an area surrounding the spot within the respective image mask indicative of the fat pad, by more than a predefined threshold;
  - position the located at least one GP within the fat pad on the anatomical imaging data; and
  - generate and output to display a combined image from said anatomical imaging modality data and said functional imaging modality data of the positioned at least one GP.

14. The system of claim 13, wherein the ANS comprises at least one GP comprising one or more of: superior left GP (SLGP), inferior left GP (ILGP), anterior right GP (ARGP), inferior right GP (IRGP), and Marshall GP.

15. The system of claim 13, wherein the ANS comprises two, three or more GPs from two or three or more of: superior left GP (SLGP), inferior left GP (ILGP), anterior right GP (ARGP), inferior right GP (IRGP), and Marshall GP.

16. The system of claim 13, wherein the anatomical imaging modality data is received before and/or during a treatment procedure.

17. The system of claim 13, further comprising an intrabody treatment probe for ablation of the nervous tissue within the heart.

18. The system of claim 17, wherein the intra-body treatment probe is at least one of a radiofrequency (RF) treatment probe, a cryosurgery treatment probe, and a probe that injects a toxin or medication.

19. The system of claim 13, wherein said program instructions include instructions that when executed by said at least one hardware processor cause said at least one hardware processor to compare a distribution of the imaged nervous tissue with one or more sets of expected distributions, and to detect abnormal synaptic distribution and/or activity based on the comparison.

20. The system of claim 13, wherein said program instructions include instructions that when executed by said at least one hardware processor cause said at least one hardware processor to track changes in the distribution of the imaged nervous tissue over time.

21. The system of claim 13, further comprising a memory for storing at least one of generated ANS models and diagnosis.

22. The system of claim 13, wherein said program instructions include instructions that when executed by said at least one hardware processor cause said at least one hardware processor to estimate the prediction of success of an ablation procedure based on measured uptake of the functional image.

23. The system of claim 13, further comprising a user input device for receiving manual input from a user, wherein said program instructions include instructions that when executed by said at least one hardware processor cause said at least one hardware processor to annotate the located nervous tissue based on the received manual input, said user input device is a member of a group consisting of at least a keyboard, a mouse and a touch screen.

24. The system of claim 13, wherein said program instructions are organized in a plurality of distributed software modules.

25. The system of claim 13, wherein when the instructions are executed by the at least one hardware processor, the execution causes the at least one hardware processor to locate the at least one GP innervating the heart based on the functional imaging modality data according to an analysis of synapse distribution and activity identified in the functional imaging modality data.

26. A system for identifying ANS components within an image of a heart of a patient and providing cardiac treatment, the system comprising:
- a non-transitory computer readable medium storing program instructions;
- at least one hardware processor in communication with said non-transitory computer readable medium, that when said instructions are executed by said at least one hardware processor, the execution causes said at least one hardware processor to:
  - receive functional imaging modality data from a nuclear medicine imaging modality which images an intrabody volume of a patient containing a heart, the patient having been injected with a radioactive imaging agent having a nervous tissue uptake by an autonomic nervous system (ANS) of the heart, the ANS comprising at least one GP comprising one or more of: superior left GP (SLGP), inferior left GP (ILGP), anterior right GP (ARGP), inferior right GP (IRGP), and Marshall GP;
  - receive anatomical imaging modality data from an anatomical imaging modality which images an intrabody volume of a patient containing the heart;
  - receive at least one image mask corresponding to location of a fat pad at a predefined anatomical region identified on an anatomical image reconstructed from said anatomical imaging modality data, wherein said at least one GP is not identifiable on said anatomical image;

apply the at least one image mask to the functional imaging modality data to the location corresponding to the fat pad at the predefined anatomical region;

locate the at least one GP in the intrabody volume of the heart within the at least one image mask applied on the functional imaging modality data and anatomical imaging modality data, by differentiating the at least one GP from the fat pad based on at least one predefined rule relying on calculated activity of a radio labeled tracer within an activity spot above a predefined threshold in comparison to surrounding activity within the at least one image mask being indicative of the at least one GP, said activity being; and generate and output to display a combined image from said anatomical imaging modality data and said functional imaging modality data of the positioned at least one GP within a fat pad.

27. The system of claim 26,
wherein said functional imaging modality is a member of a group consisting of: single-photon emission computed tomography (SPECT), electrocardiogram-gated SPECT (GSPECT), SPECT-CT, D-SPECT, A-SPECT and functional magnetic resonance imaging (fMRI); and
wherein said anatomical imaging modality is a member of a group consisting of: X-rays, ultrasound (US), computed tomography (CT) and magnetic resonance imaging (MRI).

28. The system of claim 26, wherein when the instructions are executed by the at least one hardware processor, the execution causes the at least one hardware processor to locate the at least one GP in the intrabody volume of the heart based on the functional imaging modality data and anatomical imaging modality data, according to an analysis of synapse distribution and activity identified in the functional imaging modality data.

* * * * *